US007309576B2

(12) United States Patent
O'Dowd et al.

(10) Patent No.: US 7,309,576 B2
(45) Date of Patent: Dec. 18, 2007

(54) METHOD OF IDENTIFYING TRANSMEMBRANE PROTEIN-INTERACTING COMPOUNDS

(76) Inventors: Brian F. O'Dowd, 229 Catalina Drive, Scarborough, Ontario (CA) M1E 1B8; Susan R. George, 29 Old English Lane, Thornhill, Ontario (CA) L3T 2V2

( * ) Notice: Subject to any disclaimer, the term of this patent is extended or adjusted under 35 U.S.C. 154(b) by 0 days.

(21) Appl. No.: 10/509,787

(22) PCT Filed: Apr. 11, 2003

(86) PCT No.: PCT/CA03/00542

§ 371 (c)(1),
(2), (4) Date: May 23, 2005

(87) PCT Pub. No.: WO03/087836

PCT Pub. Date: Oct. 23, 2003

(65) Prior Publication Data

US 2005/0287602 A1    Dec. 29, 2005

Related U.S. Application Data

(60) Provisional application No. 60/442,556, filed on Jan. 27, 2003, provisional application No. 60/422,891, filed on Nov. 1, 2002, provisional application No. 60/387,570, filed on Jun. 12, 2002, provisional application No. 60/379,419, filed on May 13, 2002, provisional application No. 60/371,704, filed on Apr. 12, 2002.

(51) Int. Cl.
*G01N 33/566* (2006.01)
(52) U.S. Cl. ............... 435/7.1; 435/7.2; 435/7.21; 436/501
(58) Field of Classification Search ............... None
See application file for complete search history.

(56) References Cited

FOREIGN PATENT DOCUMENTS

| WO | WO 97/48820 | 12/1997 |
| WO | WO 99/05177 | 2/1999 |
| WO | WO 02/14475 A2 | 2/2002 |

OTHER PUBLICATIONS

Bailey et al.; "Patent Status of the therapeutically important G-protein-coupled receptors", *Expert Opin. Ther. Patents* 11: 1861-1887 (2001).
Barak et al.; "A β-Arrestin/Green Fluorescent Protein Biosensor for Detecting G Protein-coupled Receptor Activation", *The Journal of Biological Chemistry* 272: 44 27497-27500 (1997).
Bertin et al.; "Cellular signaling by an agonist-activated receptor/$G_S$ α fusion protein", *Proc. Natl. Acad. Sci.* 91: 8827-8831 (1994).
Chen et al.; "A functional angiotensin II receptor-GFP fusion protein: evidence fro agonist-dependent nuclear translocation", *Am J Physical Renal Physiol* 279: F440-F448 (2000).

Conway et al.; "Quantitative analysis of Agonist-dependent parathyroid hormone receptor trafficking in whole cells using a functional green fluorescent protein conjugate", *J of Celular Phyisiol* 189: 341-355 (2001).
Coward et al.; "Chimeric G proteins allow a high-throughput signaling assay of $G_i$-Coupled receptors" *Analytical Biochemistry* 270: 242-248 (1999).
George et al.; "Oligomerization of μ and δ-Opioid receptors", *J of Biological Chemistry* 275:34 26128-26135 (2000).
George et al.; "G-protein coupled receptor oligomerization and its potential for drug discovery", *Nature* 1: 808-820 (2002).
Görlich et al.; "Nucleocytoplasmic transport", *Science* 271: 1513-1518 (1996).
Grötzinger; "Molecular mechanisms of cytokine receptor activation", *Biochimica et Biophysica Acta* 1592: 215-223 (2002).
Hailey et al.; "Fluorescence resonance energy transfer using color variants of green fluorescent protein", *Methods in Enzymology* 351: 34-49 (2002).
Hanahan et al.; "Patterns and emerging mechanisms of the angiogenic switch during tumorigenesis", *Cell* 86: 353-364 (1996).
Howard et al.; "Orphan G-protein-coupled receptors and natural ligand discovery", *Trends in Pharmacological Sciences* 22:3 132-140 (2001).
Howell et al.; "Live-cell nucleocytoplasmic protein shuttle assay utilizing laser confocal microscopy and FRAP", *BioTechniques* 32: 80-87 (2002).
Jans et al.; "Nuclear targeting signal recognition: a key control point in nuclear transport?", *BioEssays* 22: 532-544 (2000).
Lee et al.; "Novel G-protein-coupled receptor genes expressed in the brain: continued discovery of important therapeutic targets", *Expert Opin. Ther. Targets* 6: 2 185-202 (2002).
Lee et al.; "Oligomerization of dopamine and serotonin receptors", *Neuropsychopharmacology* 23: S32-S40 (2000).
Lu et al.; "Angiotensin II-Induced nuclear targeting of the Angiotenin Type 1 ($AT_1$) receptor in brain neurons", *Endocrinology* 139:1 365-375 (1998).
Masson et al.; "Neurotransmitter transporters in the central nervous system", *Pharmacological Reviews* 51:3 439-464 (1999).
Matz et al.; "Fluorescent proteins from nonbioluminescent anthozoa species", *Nature Biotechnology* 17: 969-973 (1999).
Nakae et al.; "Distinct and overlapping functions of insulin and IGF-l receptors", *Endrocrine Reviews* 22: 6 818-835 (2001).
Nicholson et al.; "EGFR and cancer prognosis", *European Journal of Cancer* 37: S9-S15 (2001).
O'Dowd et al.; "Short Communication: Discovery of three novel G-protein-coupled receptor genes", *Genomics* 47: 310-313 (1997).
Prasher et al.; "Primary structure of the Aequorea Victoria green-fluorescent protein", *Gene* 111: 229-233 (1992).

(Continued)

*Primary Examiner*—John Ulm
(74) *Attorney, Agent, or Firm*—Bereskin & Parr; Patricia Folkins

(57) ABSTRACT

A method for screening compounds for their ability to interact with transmembrane proteins is provided. Also provided is a method for determining whether proteins such as transmembrane proteins are able to oligomerize.

24 Claims, 5 Drawing Sheets

OTHER PUBLICATIONS

Schlenstedt; "Protein import into the nucleus", *Fed. Of Europ. Biocehm. Soc.* 389: 75-79 (1996).

Shawver et al.; "Smart drugs: tyrosine kinase inhibitors in cancer therapy", *Cancer Cell* 1: 117-123 (2002).

Smith; "Screening for drug discovery: the leading question", *Nature* 418: 452-459 (2002)

Strickland et al.; "Diverse roles for the LDL receptor family", *Trends in Endocrinology & Metabolism* 13: 2 (66-73).

Watson et al.; "Nuclear localization of the type 1 parathyroid hormone/parathyroid hormone-related peptide receptor in MC3T3-E1 cells: association with serum0induced cell proliferation", *Bone* 26:3 221-225 (2000).

Weis; "Importins and exportins: how to get in and out of the nucleus", *TIBS* 23: 185-189 (1998).

White et al.; "Heterodimerization is required for the formation of a functional $GABA_B$ receptor" *Nature* 396: 679-682 (1998).

METHOD OF IDENTIFYING TRANSMEMBRANE PROTEIN-INTERACTING COMPOUNDS

RELATED APPLICATION INFORMATION

The present application is a 35 U.S.C. § 371 National Phase Application of International Application Serial No. PCT/CA03/00542, filed on Apr. 11, 2003 and published in English as PCT Publication No. WO 03/087836, which claims priority from U.S. Provisional Application Ser. No. 60/371,704, filed Apr. 12, 2002, U.S. Provisional Application Ser. No. 60/379,419, filed May 13, 2002, U.S. Provisional Application Ser. No. 60/387,570, filed Jun. 12, 2002, Ser. No. 60/422,891, filed Nov. 1, 2002, and U.S. Provisional Application Ser. No. 60/442,556, filed Jan. 27, 2003, the disclosures of each of which are incorporated herein by reference in their entireties.

FIELD OF THE INVENTION

This invention relates to methods for screening compounds for their ability to interact with transmembrane proteins. The invention further relates to methods for screening transmembrane proteins for their ability to dimerise or oligomerise into groups of two or more proteins.

BACKGROUND OF THE INVENTION

In the description which follows, references are made to certain literature citations which are listed at the end of the specification and all of which are incorporated herein by reference.

Transmembrane proteins have been classified in several major classes, including G protein coupled receptors, transporters, tyrosine kinase receptors, cytokine receptors and LDL receptors. G protein coupled receptors (GPCRs) can be grouped on the basis of structure and sequence homology into several families. Family 1 (also referred to as family A or the rhodopsin-like family) is by far the largest subgroup and contains receptors for small molecules such as the catecholamines, dopamine and noradrenaline, peptides such as the opioids, somatostatin and vasopressin, glycoprotein hormones such as thyrotropin stimulating hormone and the entire class of odorant molecules (George et al, 2002). Family 2 or family B contains the receptors such as for glucagon, parathyroid hormone and secretin. These GPCRs are characterised by a long amino terminus that contains several cysteines, which may form disulphide bridges. Family 3 or family C contains receptors such as the metabotropic glutamate, the Ca2+-sensing and the gamma-amino butyric acid (GABA)B receptors. These receptors are also characterised by a complex amino terminus. Although all GPCRs share the seven membrane-spanning helices, the various GPCR families show no sequence homology to one another.

GPCRs are the largest known group of cell-surface mediators of signal transduction and are present in every cell in the body. GPCR action regulates the entire spectrum of physiological functions, such as those involving the brain, heart, kidney, lung, immune and endocrine systems. Extensive efforts during the past decade has identified a large number of novel GPCRs, including multiple receptor subtypes for previously known ligands, and numerous receptors for which the endogenous ligands are as yet unidentified, termed 'orphan' receptors or oGPCRs (Lee et al., 2001; Lee et al., 2002; Bailey et al., 2001).

GPCRs have been the successful targets of numerous drugs for diverse disorders in clinical use today, with an estimated 50% of the current drug market targeting these molecules. Among the known GPCRs, ~335 receptors are potential drug development targets, of which 195 have known ligands, and the remaining 140 being oGPCRs, awaiting identification of their ligands. Although various methodological advances have accelerated the pace of novel receptor discovery, the pace of ligand and drug discovery lags far behind. Conventional, small-scale pharmacological screening assay methods were initially used to discover the ligands and drugs for many of the GPCRs, but newer assay procedures are continually being sought.

Since GPCRs form over 80% of cell surface receptors, they represent a substantial resource and constitute a highly relevant group of protein targets for novel drug discovery. Drugs interacting with GPCRs have the potential to be highly selective, as the interactions will be confined to the cell surface and to tissues bearing the receptors exclusively. The convergence of the discovery of GPCRs with the realisation that they are important drug targets, has led to intense pharmaceutical interest in devising better ways to detect and screen for compounds interacting with GPCRs. Therefore, creating improved assay methods is an urgent requirement towards the goal of more rapid drug screening and discovery. There is a need to optimise the ability to detect an interaction between test compounds and the receptors, which is the fundamental initial step in the process of drug development.

Improved ligand-identification strategies to accelerate the characterisation of all GPCRs will define their physiological functions and realise their potential in discovering novel drugs. Even with the identified GPCRs, there is a paucity of highly selective subtype specific drugs being discovered and pharmaceutical houses are experiencing a dearth of promising lead compounds, in spite of the wealth of drug targets defined. The list of new drug product approvals by the top 20 pharmaceutical companies has declined considerably over the period 1999-2001, compared to the preceding three year period (Smith, 2002). Thus there is a real need to have improved, versatile assay systems, where not just endogenous ligands, but novel compounds interacting with receptors can be tested and identified in a quick and efficient manner that is amenable to automation.

As the signal transduction pathway required to activate an oGPCR cannot be predicted, an assay system for interacting compounds which is independent of prior predictions of which effector system (such as adenylyl cyclase, PLC, cGMP, phosphodiesterase activity) is employed by the receptor is required. Assigning ligands to GPCRs and oGPCRs is an important task; however the diversity of both GPCR ligands and effector systems can limit the utility of some existing ligand-identification assays, requiring novel approaches to drug discovery.

Recently, several methods utilising refined assay systems testing tissue extracts, large ligand libraries and specific ligands of interest have successfully discovered the endogenous ligands for a number of these oGPCRs. Such methods have been collectively referred to as "Reverse Pharmacology" (Howard et al., 2001). Various methods have been used to assay induced cell activity in response to an agonist compound, including the Fluorescence Imaging Plate Reader assay (FLIPR, Molecular Devices Corp., Sunnyvale, Calif.) and Barak et al., (1997), and U.S. Pat. Nos. 5,891,646 and 6,110,693 which disclose the use of a β-arrestin-green fluorescent fusion protein for imaging arrestin translocation to the cell surface upon stimulation of a GPCR.

The potential disadvantages of such methods are as follows: 1) visualisation is not of the receptor; 2) the protein translocation requires complex computerised analytical technologies; 3) prior identification of agonist is necessary to screen for antagonists; and 4) specific G protein coupling is necessary to generate a signal.

Mechanisms of ligand binding and signal transduction by GPCRs traditionally have been modelled on the assumption that monomeric receptors participate in the process, and a monomeric model for GPCRs has been generally accepted. Since the mid-1990s, however, numerous reports have demonstrated oligomerisation of many GPCRs (reviewed by George et al., 2002), and it is now realised that oligomerisation is an inherent aspect of GPCR structure and biology. Also certain receptor subtypes formed hetero-oligomers, and these receptors have functional characteristics that differ from homogeneous receptor populations. At present, studies of GPCR oligomerisation do not make a distinction between dimers and larger complexes, and the term dimer is used interchangeably with the terms oligomer and multimer. There are no conclusive data to indicate how large the oligomers of functional GPCRs are. Importantly, generation of new properties through hetero-oligomerisation suggested a mechanism for generating diversity of function among GPCRs. Homooligomerisation of GPCRs is accepted as a universal occurrence and a number of GPCRs are known to assemble as heterooligomeric receptor complexes (George et al., 2002). For example, the GABA-B1 and GABA-B2 receptors are not functional individually and only form a functional receptor when co-expressed (White et al., 1998). The assembly of heterooligomer receptor complexes can result in novel receptor-ligand binding, signalling or intracellular trafficking properties. For example, co-transfection of the mu and delta opioid receptors resulted in the formation of oligomers with functional properties that were distinct from each of the receptors individually (George et al., (2000). The interaction of mu and delta opioid receptors to form oligomers generated novel pharmacological and G protein coupling properties. When mu and delta opioid receptors were co-expressed, the highly selective agonists (DAMGO, DPDPE, and morphine) had reduced potency and altered rank order, whereas certain endogenous ligands endomorphin-1 and Leu-enkephalin had enhanced affinity, suggesting the formation of a novel ligand binding pocket (George et al., 2000). In contrast to the individually expressed mu and delta receptors, the coexpressed receptors showed pertussis toxin insensitive signal transduction, likely due to interaction with a different subtype of G protein. It would therefore be very useful, from the point of view of identification of potential drug targets, to have a means of determining whether a particular pair of GPCRs are able to form heterooligomers.

In many reports, heterooligomers have been tentatively identified by the ability to co-immunoprecipitate. When two GPCRs are shown to co-immunoprecipitate, however, there are two possible interpretations; either the receptors are directly physically interacting, or both are interacting through contact with a common third protein (or proteins). An alternative approach to detecting receptor oligomers has been the development of energy transfer assays using bioluminescent resonance energy transfer (BRET) or fluorescence resonance energy transfer (FRET). Although these methods detect energy transfer between two receptor molecules labelled by fluorophores at proximities of less than 100 angstroms, it is unclear whether receptor conformational changes can be reliably distinguished from de novo oligomerisation.

Transporters are protein pumps that move molecules, ions and other chemicals in and out of cells and exist in virtually all cells. The transporters can be grouped into families on the basis of structure, sequence homology and the molecules they transport. Separate transporters exist for monoamine neurotransmitters such as dopamine, serotonin, norepinephrine and GABA, for amino acids such as glycine, taurine, proline and glutamate, for vesicular monoamines, acetylcholine and GABA/glycine, for sugars such as glucose and disaccharides, for organic cations and organic anions, for oligopeptides and peptides, for fatty acids, bile acids, nucleosides, for water and for creatine. Pumps that export large molecules such as drugs, toxins and antibiotics from the cell are exemplified by the P-glycoprotein (multidrug resistance protein) family. There are also several related transporters the function of which remains unknown (Masson et al., 1999). These transporters are membrane proteins consisting of a polypeptide generally with 12 transmembrane domains. The glutamate and aspartate transporters belong to a separate family whose members have 6 to 10 TM domains and share no homology to the other transporters (Masson et al., 1999). Both the amino and carboxyl termini are located on the intracellular side of the membrane.

A large number of neurological and psychiatric disorders including depression, Parkinson's disease, schizophrenia, drug addiction, Tourette's syndrome, and attention deficit disorders are considered to involve the monoamine transporters. The dopamine transporter (DAT) is the major target for psychostimulants such as cocaine and methylphenidate. The transporters have been the successful targets of numerous drugs for diverse disorders in clinical use today, particularly antidepressant drugs, including fluoxetine, sertraline and the other related serotonin selective reuptake inhibitors (SSRIs). Although methodological molecular advances have identified the known transporters, the pace of ligand and drug discovery lags behind. Conventional, pharmacological screening assay methods were used to discover the ligands and drugs for some of the transporters, but newer assay procedures are urgently being sought. Improved ligand-identification strategies to accelerate the characterisation of all the transporters will further define their physiological functions and realise their potential in discovering novel drugs. Even with the identified transporters, there is a paucity of highly selective specific drugs being discovered.

The tyrosine kinase receptor family members are characterised by their structural similarity, with an extracellular ligand binding domain, a single transmembrane domain and an intracellular domain with tyrosine kinase activity for signal transduction. There are many subfamilies of receptor tyrosine kinases, exemplified by the epidermal growth factor (EGF) receptor (also called HER1 or erbB1), which is one of four members of such a subfamily, which also includes HER2, HER3 and HER4. The principal EGF-R ligands are EGF, TGF-α, heparin binding EGF, amphiregulin, betacellulin and epiregulin (Shawver et al., 2002). Activation of the EGF-R causes the receptor to dimerise with either another EGF-R monomer or another member of the HER subfamily. Marked diversity of ligand binding and signalling is generated by the formation of heterodimers among family members (Yarden and Sliwkowski, 2001). The EGF-R is widely expressed in a variety of tissues and mediates important functions such as cell growth and tissue repair. Overexpression of EGF-R occurs in many types of cancer, such as head and neck, lung, laryngeal, esophageal, gastric, pancreatic, colon, renal, bladder, breast, ovarian, cervical, prostate, thyroid, melanoma and glioma, and correlates with a poor outcome (Nicholson et al., 2001). Therefore there is great interest and need for developing drugs targeting the EGF-R and for methods which assist in identifying such drugs.

Other subfamilies of receptor tyrosine kinases are exemplified by the receptors for vascular endothelial factor (four members) and fibroblast growth factor (four members). These have important roles in angiogenesis and also have significant roles in the uncontrolled proliferation of vessels characterizing carcinogenesis (Hanahan and Folkman. 1996).

The cytokine receptors are proteins spanning the membrane with an extracellular ligand binding domain and an intracellular domain with intrinsic kinase activity or adapter regions able to interact with intracellular kinases. The receptors are divided into subclasses based on their structural complexity. The 'simple' receptors are those including receptors for growth hormone, erythropoietin and interleukins, and the 'complex' receptors include the tumour necrosis factor receptor family, the 4-helical cytokine receptor family, the insulin/insulin-like receptor family and granulocyte colony stimulating receptor (Grotzinger, 2002).

The insulin and insulin-like growth factor (IGF) receptor family controls metabolism, reproduction and growth (Nakae et al., 2001). There are nine different insulin-like peptides known and there are three known receptors that interact with them, IR, IGF-1R and IGF-2R, and an orphan member IR-related receptor. Each receptor exists as homodimers on the cell surface or heterodimers. The IR subfamily is also related to the EGF-R family.

IR, produced from a single mRNA, undergoes cleavage and dimerisation and translocation to the plasma membrane. Each monomer component contains a single transmembrane domain; the complete receptor comprised two α and two β subunits, linked by disulphide bridges. The β subunit contains the single TM and the intracellular region. This receptor is a tyrosine kinase that catalyzes the phosphorylation of several intracellular substrates.

The low density lipoprotein (LDL)-receptor family act as cargo tranporters, regulating the levels of lipoproteins and proteases (Strickland et al., 2002). There are nine recognised members of the family, all of which share structural similarity, including an extracellular region, a single transmembrane domain region and a cytoplasmic tail. The LDL receptor plays a major role in the clearance of lipoproteins, and genetic defects in the LDL receptor can result in the accumulation of LDL in the bloodstream.

The first characterised motif shown to be able to direct protein nuclear importation was exemplified by the amino acid sequence (PKKKRKV:SEQ ID NO: 129) contained in the SV40 large T antigen protein. The nuclear localisation sequence (NLS) motifs are recognised by the importin α-β receptor complex, which binds the NLS (Gorlich et al., 1996). These are cytosolic proteins, which recognise NLS containing proteins and transport these proteins to dock at the nuclear pore. The entire complex subsequently docks at the nuclear pore complex (Weis et al., 1998, Schlenstedt et al., 1996), contained at the nuclear envelope. The nuclear envelope is a boundary containing pores that mediate the nuclear transport process (Weis et al., 1998).

There have been very few and rare reports of GPCRs localising in the nucleus. One such example is the GPCR angiotensin type 1 (AT$_1$) receptor, which contains an endogenous NLS which serves to direct the GPCR into the nucleus (Lu et al., 1998), providing evidence that this NLS sequence was involved in the nuclear targeting of the AT1 receptor. These authors and Chen et al., (2000) reported that AT1 receptors increased in the nucleus in response to agonist. The nuclear localisation of the parathyroid hormone receptor has been reported (Watson et al, 2000). However very few of the superfamily of GPCRs contain an endogenous NLS mediating translocation of the receptor to the nucleus.

There therefore remains a need for new, more convenient methods for identifying compounds which interact with transmembrane proteins such as GPCRs, transporters, etc. There also remains a need for improved, less ambiguous methods for detecting oligomerisation of transmembrane proteins.

SUMMARY OF THE INVENTION

The inventors have shown that the incorporation of a nuclear localisation sequence (NLS) into a transmembrane protein (not containing an endogenous functional NLS) routes the protein from the cell surface into the nucleus of a cell in a time-dependent and ligand-independent manner. In order to visualise this trafficking of transmembrane proteins from the cell surface, they carry a detectable moiety for visualisation by a variety of means. It has been demonstrated that membrane proteins from diverse protein families containing a synthetically incorporated NLS are redistributed under basal conditions from the cell surface to and towards the nucleus.

This process can be exploited to identify compounds which interact with transmembrane proteins by determining whether candidate compounds are able to modulate this ligand-independent transfer of a transmembrane protein away from the cell membrane.

It is also now possible, using methods based on this process, to determine whether protein molecules are able to oligomerise.

In accordance with one embodiment, the invention provides a method for screening a candidate compound for its ability to interact with at least one transmembrane protein comprising:

transfecting a cell with at least one nucleotide sequence encoding a protein comprising a transmembrane protein containing at least one nuclear localisation sequence (NLS) and a detectable moiety and permitting expression of the encoded protein in the cell;

contacting the cell with a candidate compound; and determining the distribution of the expressed protein in the cell by detecting the distribution of the detectable moiety in the cell;

wherein detection of an altered distribution of the detectable moiety in the cell relative to the distribution of the detectable moiety in a control cell not contacted with the candidate compound indicates that the compound interacts with the transmembrane protein.

In accordance with a further embodiment of this method, the cell is contacted with a compound known to interact with the at least one transmembrane protein prior to contacting the cell with the candidate compound and wherein detection of an altered distribution of the detectable moiety in the cell relative to the distribution of the detectable moiety in a control cell contacted with the compound known to interact with the transmembrane protein but not contacted with the candidate compound indicates that the candidate compound interacts with the transmembrane protein.

In accordance with a further embodiment, the invention provides a method for screening a candidate compound for its ability to interact with at least one transmembrane protein comprising:

transfecting a cell with at least one nucleotide sequence encoding an NLS-containing transmembrane protein and permitting expression of the encoded protein in the cell;

contacting the cell with a candidate compound; and determining the level of NLS-containing transmembrane protein remaining at the cell membrane by isolating the cell membrane fraction of the cell, contacting the fraction with a labelled ligand of the transmembrane protein and determining the level of binding of the ligand to the fraction;

wherein detection of an altered level of the transmembrane protein at the cell membrane relative to the level at the cell membrane in a control cell not contacted with the candidate compound indicates that the compound interacts with the transmembrane protein.

In accordance with a further embodiment, the invention provides an isolated cell transfected with at least one nucleotide sequence encoding a protein comprising a transmembrane protein containing at least one NLS and a detectable moiety.

In accordance with a further embodiment, the invention provides a method for determining whether a first protein and a second protein are able to oligomerise comprising:

transfecting a cell with a first nucleotide sequence encoding a first protein containing an NLS and a second nucleotide sequence encoding a second protein comprising a detectable moiety and permitting expression of the encoded first and second proteins in the cell; and determining the distribution of the detectable moiety in the cell;

wherein detection of the detectable moiety in or adjacent to the nucleus of the cell or detection of a reduced level of the detectable moiety at the cell surface, relative to a control cell, indicates that the first and second proteins interact.

SUMMARY OF THE DRAWINGS

Certain embodiments of the invention are described, reference being made to the accompanying drawings, wherein.

DETAILED DESCRIPTION OF THE INVENTION

Figure 1:
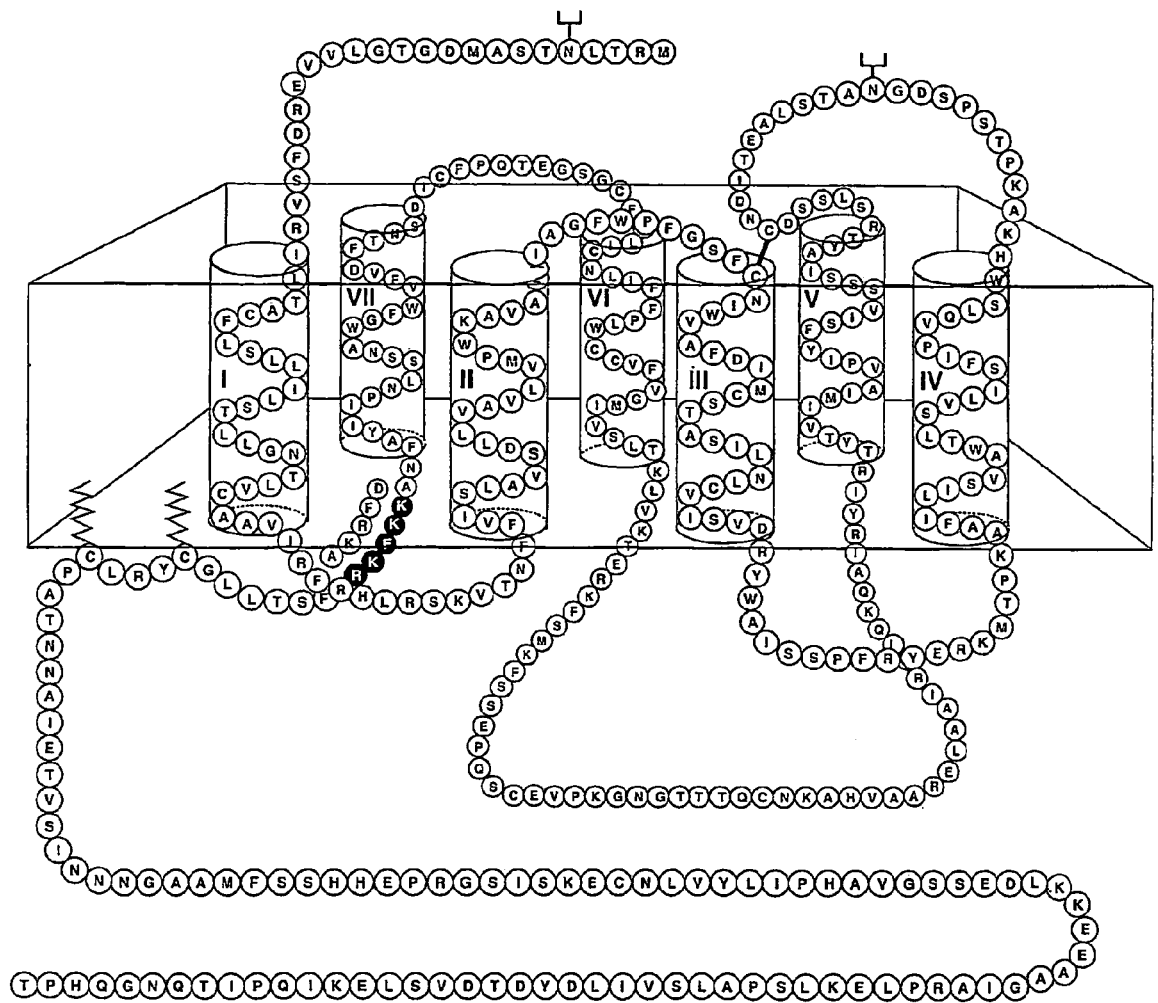
FIG. 1 shows in diagrammatic form the structure of a typical GPCR, the dopamine D1 receptor [SEQ ID NO: 159], modified to contain an NLS.

The invention provides, in one embodiment, a new and convenient method for screening candidate compounds for their ability to interact with a transmembrane protein.

As used herein, when a candidate compound and a transmembrane protein "interact", this means that the compound is a ligand of the transmembrane protein and binds to the protein or is able to modulate the trafficking of the transmembrane protein away from the cell membrane described herein.

Identification of compounds which interact with a transmembrane protein is the first important step in the process of identifying lead compounds for drug development.

Working initially with GPCRs, the inventors have found that when a nucleated eukaryotic cell is transfected with a nucleotide sequence which encodes a GPCR containing a synthetically incorporated NLS, or a naturally occurring NLS, and the cell is permitted to express the nucleotide sequence, the expressed GPCR travels first to the cell membrane and then is transferred to the cell nucleus. This process is independent of ligand activation and takes from about 6 to about 72 hours, depending on the transmembrane protein involved, with an average of 24 to 48 hours. This is in contrast to the situation when a GPCR not containing an NLS is expressed in a cell, when the expressed GPCR remains predominantly at the cell surface, with small amounts occurring in the cytoplasm but no detectable amounts in the nucleus.

The inventors have also found that the transfer or trafficking of the expressed NLS-containing GPCR from the cell membrane to or towards the nucleus can be modulated by treating the transfected cell with a compound which interacts with the GPCR. Screening of candidate compounds for their ability to interact with a GPCR can therefore be carried out by detecting this modulation of transfer of the expressed GPCR from the cell membrane to the nucleus.

The inventors have further found that these observations are widely applicable to transmembrane proteins generally, and are not limited to GPCRs.

"Transmembrane protein" as used herein means a single chain protein found in the cell membrane and having at least one domain that spans the cell membrane.

The inventors have shown that a wide variety of transmembrane proteins from several families of the GPCR group, from the transporter group, from the cytokine receptor group, from the tyrosine kinase group and from the low density lipoprotein receptor group, if expressed in a nucleated cell so that they contain an NLS group, all show initial accumulation of the expressed protein at the cell membrane, followed by ligand activation-independent transfer of the expressed protein away from the cell membrane and into the cell nucleus.

The wide applicability of the methods of the invention is indicated by the immense variety of transmembrane protein structures represented by the exemplified transmembrane proteins used in the method; NLS insertion into a transmembrane protein resulting in translocation of the protein off the cell surface and to the nucleus has been shown to be effective with membrane proteins having one transmembrane (TM) domain, seven TM domains and twelve TM domains and sharing little or no sequence homology.

It has been found that the method of the invention is widely applicable to identifying compounds which interact with transmembrane proteins.

Compounds which interact with transmembrane proteins have been found to modulate their transfer from cell membrane to nucleus in different ways, including inhibition of the transfer, acceleration of the transfer and interference with the modulation produced by other compounds. Any interacting compound is of interest as a potential drug candidate.

Modulation of the transfer of expressed transmembrane protein is determined by comparing the distribution of the transmembrane protein within the cell in control cells and cells treated with a candidate compound.

In one embodiment, the method provides a convenient tool for screening candidate compounds for their ability to interact with a GPCR and modulate its trafficking. Compounds that specifically interact with the GPCR may inhibit or prevent transfer of the GPCR from the cell surface to the nucleus and may be antagonists to the GPCR, whereas other compounds can accelerate the transfer of GPCR to the nucleus, relative to a control cell and may be agonists to the GPCR.

To allow determination of the distribution of the expressed transmembrane protein within the cell, with and without exposure to a test compound, the expressed transmembrane protein must carry a detectable moiety, which can be detected in the cell. The detectable moiety may be any moiety which will remain associated with transmembrane protein throughout its expression and trafficking within the cell and can be directly or indirectly detected to determine its distribution within the cell and to determine an altered distribution resulting from exposure to a candidate compound.

In a first embodiment, the cell is transfected with a nucleotide sequence encoding a fusion protein comprising a transmembrane protein containing at least one NLS linked to a detectable moiety comprising a detectable peptide or polypeptide. As used herein, a peptide means a sequence of two to 20 amino acid residues, preferably a sequence of about 5 to about 15 amino acid residues, and a polypeptide means a sequence of more than 20 amino acid residues, including full proteins of any length. The detectable peptide or polypeptide may be directly detectable or may be reactable to give a detectable signal. The detectable peptide may be, for example, an antigenic peptide or epitope which is expressed, for example, at the amino terminus of the transmembrane protein. The distribution of the transmembrane protein within the cell is detected by detection of the epitope using a detectable antibody specific for the epitope. A number of suitable epitope antibody systems are available commercially. Examples are the HA (Roche Diagnostics), FLAG (Sigma Chemical Co.), c-myc (Santa Cruz), Histidine hexamer (BD Biosciences Clontech), GST (ABR Affinity BioReagents), V5 (Abcam) and Xpress (Invitrogen) epitope/antibody systems.

Nucleotide sequences encoding these epitopes can be purchased, as well as antibodies specific for the epitopes. These antibodies may carry a detectable label (e.g. fluorescein isothiocyanate (FITC)) or may themselves be detected by use of a second antibody carrying a detectable label, as will be understood by those of skill in the art. This embodiment of the invention is particularly adaptable to an automated or semi-automated method, for example by examining antibody-treated plates of cells in an automated plate reader, allowing for high through put screening.

The detectable polypeptide may be an optically detectable polypeptide such as green fluorescent protein (GFP), red fluorescent protein (RFP), yellow fluorescent protein (YFP) and or cyan fluorescent protein (CFP), or any of the modified variants of these proteins, which are commercially available. The detectable polypeptide may also be an enzyme such as luciferase or β-galactosidase, which can be reacted to give a detectable end point such as light emission or colour change. Nucleotide sequences encoding such polypeptides are readily available, for example from Clontech, and are linked to the nucleotide sequence encoding the NLS-containing transmembrane protein, preferably at the C-terminal end of that protein.

In a further embodiment, the detectable moiety is an antigenic peptide comprising a portion of the amino acid sequence of the transmembrane protein itself, preferably a portion of an extracellular region of the protein. As described above, the distribution of the transmembrane protein within the cell is determined using a detectable antibody specific for the epitope. Suitable antibodies are available commercially, e.g. anti-D1 antibody directed to amino terminal amino acids 9-21 of the human D1 dopamine receptor, or may be prepared by conventional methods.

In a further embodiment, applicable to transmembrane proteins with known ligands, the cell is transfected with a nucleotide sequence encoding a transmembrane protein containing at least one NLS. The cells are contacted with a candidate compound and incubated as described above. The cells are then harvested and the cell membrane fraction is isolated and contacted with a detectably labelled ligand of the transmembrane protein, for example a radio-labelled ligand. Determination of the amount of labelled ligand bound to the membrane fraction of treated cells, relative to the amount bound to the membrane fraction of control cells not contacted with the candidate compound, can be used to quantitate the transmembrane protein remaining at the cell surface and indicate interaction of the candidate compound with the transmembrane protein.

Transmembrane protein-encoding nucleotide sequences can be obtained from public databases such as Genbank or from commercial databases. Suitable constructs may be synthesised by conventional methods, as described in the examples herein, or obtained commercially.

"An NLS-containing transmembrane protein" includes a transmembrane protein which contains an NLS in its wild type sequence and a transmembrane protein whose amino acid sequence has been modified to contain an NLS.

Conventional NLSs are short peptide sequences that facilitate nuclear localisation of the proteins containing them (see for example, Table 1 which lists NLSs and Jans et al., 2000). There are three major classes of NLSs; two of these classes consist of basic amino acid residues, the monopartite NLSs, exemplified by the SV40 large tumor antigen, PKKKRKV (SEQ ID NO: 129), consisting of a single stretch of basic amino acids, and the bipartite NLSs which contain two stretches of basic amino acids separated by 10 to 22 (sometimes up to hundreds) amino acids. Other types of NLSs are exemplified by those of the yeast protein Mata2 NLS where charged/polar residues are contained within the stretch of non-polar residues, or the protooncogene c-myc NLS, where proline and aspartic acid residues flanking the basic residues are required (PAAKRVKLD: SEQ ID NO: 135) for nuclear targeting. All classes of NLS are recognized specifically by the α-β-importins.

Any NLS may be employed in the methods of the invention. Nucleotide sequences encoding a selected NLS may be derived from the amino acid sequence of the NLS and are synthesised and incorporated into the nucleotide sequence encoding the transmembrane protein by conventional methods, as described herein. Many different locations within any of the intracellular loops or intracellular termini of the transmembrane protein are suitable for insertion of the NLS. Insertion of the NLS within an intracellular domain of the protein is preferred. For example, in a GPCR, the NLS could be placed in any of the intracellular loops or intracellular carboxyl tail. In a 12 TM transporter, the NLS could be placed in the intracellular amino or carboxyl termini or any of the intracellular loops.

When an NLS is inserted into a transmembrane protein for use in the methods of the invention, the efficacy of the insertion can be screened by confirming that the NLS-containing transmembrane protein is substantially translocated from the cell membrane to the cell nucleus within 24 to 48 hours and that ligands of the transmembrane protein interfere with the translocation.

Nucleotide sequences encoding NLS-containing transmembrane proteins are linked to sequences encoding detectable peptides or polypeptides by conventional methods.

A nucleotide sequence encoding a selected NLS-containing transmembrane protein containing or linked to a detectable moiety, is transfected into a nucleated cell by cloning the sequence into a vector system containing a suitable promoter, using conventional techniques as described in the scientific literature, for example in Current Protocols in Molecular Biology, (1987). Suitable vectors include the pEGF-N1 (Clontech) which contains the human cytomegalovirus (CMV) promoter, and the vector pcDNA.

Any cell may be used which is capable of expressing the transfected nucleotide sequences and in which an NLS facilitates transfer of a transmembrane protein away from the cell membrane. Suitable cells include prokaryotic cells, including bacterial cells, and eukaryotic cells. Suitable eukaryotic cells include isolated mammalian cells, yeast cells, plant cells, insect cells, nematode cells and fungal cells. Suitable mammalian cells include human cell lines, rodent cell lines, hamster cell lines, non-human primate cell lines.

In one embodiment, the cell is transfected with a number of nucleotide sequences, each encoding a different NLS-containing transmembrane protein and a different detectable moiety. Interference with trafficking of the transmembrane protein away from the cell membrane by a test compound can be related to interaction of the compound with a particular transmembrane protein by the identity of the detectable moiety whose movement from the cell surface is interrupted.

In a further embodiment, for higher throughput initial screening, the cell is transfected with a greater number of nucleotide sequences, each encoding a different NLS-containing transmembrane protein and a detectable moiety, some of the detectable moieties being common to more than one transmembrane protein. If initial screening indicates that a candidate compound is interacting with one or more of the transmembrane proteins, the compound is rescreened using a cell expressing fewer transmembrane proteins, or only one, until the specific interacting transmembrane protein is identified.

In cells transfected with more than one transmembrane protein, there may be oligomerisation between pairs of proteins as discussed herein, and this may affect the interpretation of the effect of a candidate compound. Subsequent rescreening of the compound using cells transfected with only one transmembrane protein allows clarification of the interaction of the compound with a particular protein.

Alternatively, for multiply transfected cells, transmembrane proteins may be selected which have been shown not to oligomerise with each other.

Identification of Interacting Compounds

In one embodiment of the invention, nucleated cells are transfected with a nucleotide sequence encoding a protein comprising a transmembrane protein containing an NLS and a detectable moiety and incubated for a suitable period of time to allow expression of the NLS-transmembrane protein and commencement of its accumulation at the cell membrane. For GPCRs and transporters, for example, a time period of about 6 to 24 hours is suitable. One of skill in the art can readily determine a suitable incubation time for other transmembrane proteins by observation of the accumulation of the protein at the cell membrane. All of the expressed transmembrane protein need not have reached the cell membrane when the candidate compound is added. Test cells are then contacted with a candidate compound which is to be tested for interaction with the transmembrane protein for a period of time which is sufficient to allow translocation of a substantial portion of the NLS-transmembrane protein, preferably at least 20%, more preferably at least 50%, and still more preferably at least 90%, away from the cell membrane and into or towards the nucleus in a control cell not treated with compound.

Depending on the transmembrane protein, this period of time may be from about 6 hours to about 72 hours; a time period of about 24 to about 48 hours is suitable for most transmembrane proteins examined. One of skill in the art can readily determine a suitable time by observation of control cells.

Test compounds are initially tested generally at a concentration of about 1 to 10 micromolar.

Test and control cells are then examined to determine the distribution of the detectable moiety and thereby the distribution of the NLS-transmembrane protein. The distribution of the detectable moiety may be determined by various methods. For example, when the detectable moiety is an optically detectable protein, the cells may be examined by direct microscopy and the amount of protein in the nucleus compared between test and control cells. In another embodiment, the amounts of detectable protein or peptide remaining in the membrane of control and test cells are compared. In several microscopic fields (5-10), each containing 30-100 cells, the location of the detectable moiety in these cells is determined and counted for each location. The percentage of cells having cell surface, or nuclear labelling and the sum of all the fields is then calculated for the treated and control cells.

In a further example, when the detectable moiety is an antigenic epitope, the cells are contacted with a detectable antibody system containing an antibody specific for the epitope, as described above. For example, a first antibody specific for the epitope may be used, followed by a fluorescently labelled second antibody specific for the first antibody, the fluorescent signal being quantified by fluorometer.

Where control cells show a substantial portion, preferably at least 50%, of the transmembrane protein translocated away from the cell membrane and test cells show retention of the transmembrane protein at the cell membrane, relative to control cells, this indicates interaction of the test compound with the transmembrane protein. In a preferred embodiment, interaction is indicated when the level of protein at the cell membrane is higher in the test cells by at least 10%, preferably by at least 15%, and more preferably by at least 20%.

The proportion of the detectable moiety remaining at the cell membrane on exposure to the interacting compound is related to the concentration and potency of the compound. For example, the use of a known potent GPCR antagonist in micromolar concentration typically resulted in about 50 to 100% of the protein remaining at the cell surface, 0 to 15% in the nucleus and the remainder in the cytoplasm. Lower nanomolar concentrations of the same antagonist resulted in retention of 20 to 40% of the protein at the cell surface, with the rest of the protein in the cytoplasm and nucleus. In the untreated control cells, 0-15% of the protein was detectable at the cell surface, with the remainder in the cytoplasm and nucleus.

In a variant of this method, used where the transmembrane protein has known ligands, an expressed NLS-containing transmembrane protein without a detectable moiety is used and distribution of the protein in the cell after treatment with a test compound is determined by isolation of the cell membrane fraction and determination of its transmembrane protein component using detectably labelled ligand, as discussed above.

In a further embodiment of the invention, a similar method is used to identify compounds which interact with an NLS-transmembrane protein to promote its translocation away from the cell surface and into or towards the nucleus. Cells are transfected and incubated to permit expression of the NLS-transmembrane protein and its accumulation at the cell surface. Preferably, the cells are incubated until at least about 70 to 90% of the expressed transmembrane protein has accumulated at the cell surface. For many transmembrane proteins, a time period of about 12 to about 24 hours from transfection is suitable.

Test cells are then contacted with a candidate compound, and individual test and control cells are immediately observed in real time for up to 4 hours to observe the distribution of the detectable moiety. An increased accumulation of detectable moiety in the nucleus of test cells compared with control cells indicates that the test compound has promoted translocation of the transmembrane protein. In a preferred embodiment, interaction is indicated when test cells show nuclear accumulation increased by at least 5%, preferably by at least 10%, and more preferably by at least 20%.

A further embodiment of the invention is a method for identifying compounds which, although they do not themselves prevent translocation of an NLS-containing transmembrane protein away from the cell membrane, nevertheless can interfere with the interaction of the transmembrane protein with an interacting compound.

Compounds which have proved negative in the first screening method described above may be tested by this further method for their ability to compete with a known interacting compound.

In this method, cells are transfected as described above and incubated for a suitable period of time to allow expression and accumulation of the transmembrane protein at the cell surface, for example for about 24 to about 48 hours.

Test cells and control cells are then contacted with a compound known to interact with the transmembrane protein, either a known ligand or an interacting compound identified by the method described above, for about 24 to about 48 hours. Test cells are then contacted with a candidate compound and test cells and control cells are observed after 1 hour, at one or more time points, up to 24 hours, to determine distribution of the NLS-transmembrane protein within the cells as described above. In control cells, the known interacting compound causes the transmembrane protein to be retained at the cell membrane. If the candidate compound competes with the interacting compound, test cells show a reduction of transmembrane protein at the cell surface and increased translocation of the protein away from the cell surface. In a preferred embodiment, interaction is indicated when test cells show a reduction of at least 10%, preferably 15%, and more preferably 20%.

In a further embodiment, a cell which endogenously expresses an NLS-containing transmembrane protein may be employed, in conjunction with a first compound which has been demonstrated to interact with the protein and inhibit its transfer from the cell membrane, thus retaining the protein at the cell membrane. When such a system is contacted with a candidate compound, if that compound interacts with the transmembrane protein and competes with the first compound, an increased transfer of the protein away from the cell membrane is observed.

Identifying Transmembrane Protein Interactions with Other Proteins

A number of transmembrane proteins, including GPCRs, transporters, tyrosine kinase receptors, the cytokine receptors for insulin, insulin-like growth factors, the epidermal growth factor and vascular endothelial growth factor, are capable of both homo- and heterooligomerisation (see, for example, review of GPCRs in George et al., 2002). As used herein, "oligomerisation" of a protein means association of two or more molecules of the protein.

For hypothetical receptors A and B, the cell surface may contain dimers AA, BB and AB and it is believed that these may represent three different functional complexes and therefore three different drug targets. It is therefore important to identify which transmembrane proteins can interact with each other or with other proteins by oligomerisation.

In further embodiments, the invention provides methods for determining whether two transmembrane proteins are capable of oligomerisation or whether a transmembrane protein and a non-transmembrane protein are capable of oligomerisation.

In one embodiment, a nucleated cell is co-transfected with a first nucleotide sequence encoding a first transmembrane protein containing an NLS and a second nucleotide sequence encoding a second transmembrane protein lacking an NLS but carrying or linked to a detectable moiety. Creation of these nucleotide sequences is as described above. After a suitable time interval to allow for expression of the encoded proteins, accumulation at the cell membrane and subsequent translocation of the NLS-containing protein away from the cell membrane to or towards the nucleus, the distribution of the detectable moiety in the cell is determined, for example by determining an increase of detectable moiety in the nucleus or by a decrease of detectable moiety at the cell surface.

It has been found that when cells are doubly transfected, and the first and second transmembrane protein are the same, except that one transmembrane protein contains an inserted NLS and the other does not, there is a slowing of the transfer of the NLS-containing transmembrane protein to the cell nucleus compared with transfer in a cell transfected only with the NLS-containing protein. The process of protein translocation to the nucleus now may take about 24 to 48 hours. In this method, therefore, the cells are incubated for about 24 to 48 hours before examination of the distribution of protein in the cell.

Translocation of the detectable moiety from the cell surface to or towards the nucleus indicates that the first transmembrane protein has carried the second transmembrane protein away from the cell surface, indicating oligomerisation of the first and second proteins. Retention of the detectable moiety at the cell surface indicates a lack of interaction between the proteins.

When the first and second transmembrane proteins are the same protein, the method allows the identification of the ability of the protein to homodimerise. When the first and second transmembrane proteins are different, the method allows the identification of the ability of two different proteins to heterodimerise and permits the determination of the specificity of interaction between two transmembrane proteins.

The method may be carried out either in the absence of ligand activation or in the presence of a ligand of either protein.

Using this method, oligomerisation has been demonstrated both within and between different classes of GPCRs and within and between other classes of transmembrane proteins.

In addition, interactions have been detected between GPCRs and non-GPCR transmembrane proteins, for example between the D5 dopamine receptor and the GABA-A receptor, and between transmembrane proteins and non-transmembrane proteins.

The invention therefore generally provides a method for detecting oligomerisation between two proteins by the method described above, where a cell is co-transfected with one of the proteins containing an NLS and the other protein carrying a detectable signal.

Co-transfection of a cell with a first transmembrane protein containing an NLS and a second detectably labelled protein, such as a transmembrane protein from a different group, which has been shown by the method of the invention to oligomerise with the first protein, provides a cell which can be used to screen candidate compounds for interaction with either the first or second protein. A compound which interacts with either protein will influence oligomerisation or translocation of the oligomerised proteins away from the cell membrane. Compounds which interact with one member of the protein pair or with the oligomer to cause retention of the detectable protein at the cell surface or to cause accelerated translocation of the detectable protein away from the cell surface may be identified by this method.

In a further embodiment, a cell which endogenously expresses an NLS-containing transmembrane protein is transfected with a nucleotide sequence encoding a second transmembrane protein carrying a detectable moiety but lacking an NLS. Oligomerisation of the two proteins is indicated by trafficking of the detectable moiety away from the cell membrane and into or towards the nucleus.

In a further embodiment, a membrane protein containing an NLS may be used to identify novel interacting proteins. In this method, an NLS-containing transmembrane protein is expressed in a cell and is allowed to translocate to the nucleus. The nuclei are then harvested and assayed for newly appeared protein bands by Coomassie staining or silver staining and then identification by mass spectroscopy. The control will be nuclei from cells expressing the membrane protein without a NLS.

Use of FRET for Detection of Nuclear Translocation.

In a further aspect of the invention, involving fluorescence resonance energy transfer (FRET) (Hailey et al., 2002), a nucleated cell is co-transfected with a first nucleotide sequence encoding a first NLS-containing transmembrane protein linked to a first optically detectable protein and a second nucleotide sequence encoding a second non-NLS-containing transmembrane protein linked to a second optically detectable protein, whose fluorescence can be activated by the emission of the first optically detectable protein when these are in close proximity. For example, the first protein may be linked to GFP and the second any other optically detectable moiety that can be activated by the laser activated emission spectrum of GFP. This second optically detectable moiety, after activation by the GFP, emits at a different wavelength. Where oligomers are formed between the two transmembrane proteins, the two labels are in close proximity to each other and their FRET interaction can be detected. The physical interaction is detected by selective fluorescence activation of the donor and detection of emission by the acceptor, using the FRET method or its variants such as photobleaching FRET, FRAP or FLIM. Lack of a FRET interaction indicates lack of oligomerisation.

Confocal microscopy with FRET between two fluorescent molecules may be performed (e.g. the spectral pairs GFP and DsRed2, or CFP and YFP) to obtain a quantifiable signal indicating translocation to the nucleus. FRET requires an overlap between the emission and excitation spectra of donor and acceptor molecules and a proximity of under 100 angstroms (10-100), making FRET a highly suitable system to assay for specific close protein-protein interactions in cells. The fluorescent proteins listed above are excellent spectral partners. A resident fluorophore in the nucleus would enable FRET to occur when a transmembrane protein tagged with second fluorophore is translocated to the nucleus. This will facilitate an easy readout, using a FRET plate reader. This method is useful for detecting interactions between two transmembrane proteins or between a transmembrane protein and another protein and provides a signal readout more amenable to automation.

This method can also be used in GPCR agonist and antagonist screening procedures. In the antagonist screening method, a reduction of a FRET signal between a GPCR-NLS-GFP trafficked to the nucleus with a fluorophore in the nucleus of treated cells compared to non treated cells would indicate an antagonist effect. In the agonist screening method, the increase in the FRET signal between a GPCR-NLS-GFP trafficked to the nucleus with a fluorophore in the nucleus of treated cells compared to non treated cells would indicate an agonist effect. In a further embodiment, the doubly transfected cells may be treated with an agonist before examination for evidence of oligomerisation, since this may be enhanced in the presence of agonist. In the measurement of receptor:receptor interactions, a GPCR-NLS-GFP is co-expressed with a second GPCR-DsRED. If these receptors interact with each other and traffic together to the nucleus a nuclear FRET signal will be detected. If the receptors do not interact then no FRET signal will be obtained in the nucleus. FRET may also be measured between two fluorophore-conjugated antibodies recognising incorporated ot native epitopes on the GPCRs.

EXAMPLES

The examples are described for the purposes of illustration and are not intended to limit the scope of the invention.

Methods of chemistry, molecular biology, protein and peptide biochemistry and immunology referred to but not explicitly described in this disclosure and examples are reported in the scientific literature and are well known to those skilled in the art.

Materials and Methods

Green fluorescent protein: a DNA sequence encoding the *Aequoria victoria* green fluorescent protein (Prasher et al., 1992) was obtained from Clontech, U.S.A.

Red fluorescent protein: a DNA sequence encoding the red fluorescent proteins (Matz et al., 1999) pDsRed2 and pDsRed2-nuc were obtained from Clontech, U.S.A. This construct encodes a protein derived from *Discosoma* sp.

COS cells and HEK cells were obtained from American Type Culture Collection, Washington, D.C. The cell culture media were prepared by laboratory services at the University of Toronto.

Antagonist and agonist compounds were obtained from various commercial sources such as Sigma Chemical Company U.S.A.

Antibodies used for immunodetection of epitope tags were obtained from the following sources: Anti-HA monoclonal antibody was obtained from Roche Diagnostics, U.S.A. Anti-FLAG monoclonal antibody was obtained from Sigma Chemical Company, U.S.A. Anti-c-myc monoclonal antibody was obtained from Santa Cruz, U.S.A.

Radioligand $^3$H-SCH 23390 used in the receptor binding assay was obtained from NEN Perkin Elmer, U.S.A.

Creation of DNA Constructs

Nucleotide sequences encoding GPCR's or transporters were obtained from the Genbank (http://www.ncbi.nlm.nih.gov:80/entrez) web site, established by the National Library of Science. A nucleotide sequence encoding a selected transmembrane protein was attached to a nucleotide sequence encoding a selected detectable signal protein. The constructs were cloned into the vector system, pEGFP (Clontech) or the pDsRed2-N1 vector or the vector pcDNA3.

1a. Construction of the Human D1 Dopamine Receptor with a NLS in the Proximal Carboxyl Tail (Helix 8) and Fused to GFP (D1-GFP and D1-NLS-GFP).

Using the PCR method with the following experimental conditions, DNA encoding the human D1 dopamine receptor in the vector pcDNA3, was subjected to PCR. The reaction mixture contained water (32 microlitres), 10×Pfu buffer (Stratagene) (5 microlitres), dNTP (2'-deoxynucleoside 5'-triphosphate, 10 mM) (5 microlitres), DMSO (5 microlitres), oligonucleotide primers (100 ng) (1 microlitre each), DNA template (100 ng), Pfu enzyme (5 units). Total volume was 50 microlitres. The following PCR conditions were used, one cycle at 94° C. for 2 mins, 30-35 cycles at 94° C. for 30 secs, 55° C. for 30 secs, 72° C. for 1 min, per cycle, and then one cycle at 72° C. for 5 mins.

Primer set for amplification of the DNA encoding the D1-dopamine receptor:

HD1-P1:                                      (SEQ ID NO:1)
5' GAGGACTCTGAACACCGAATTCGCCGCCATGGACGGGACTGGGCTGGT
G 3'

HD1-P2:                                      (SEQ ID NO:2)
5' GTGTGGCAGGATTCATCTGGGTACCGCGGTTGGGTGCTGACCGTT 3'

The restriction site EcoR1 was incorporated in the primer HD1-P1, and restriction site Kpn1 was incorporated into the primer HD1-P2. The PCR product, which contained no stop codon was unidirectionally subcloned into vector pEGFP (from Clontech) at EcoR1 and Kpn1 and inframe with the start codon of the GFP protein.

The NLS sequence, KKFKR (SEQ ID NO: 157) from the human AT1 receptor was inserted into DNA encoding the base of TM7 (helix 8) of the D1 dopamine receptor by PCR, replacing the natural sequence coding for DFRKA.

The primer set for the construction of DNA encoding D1-NLS:

HD1-NLSF:                                    (SEQ ID NO:3)
5' CCTAAGAGGGTTGAAAATCTTTTAAATTTTTTAGCATTAAAGGCATAA
ATG 3'

HD1-NLSR:                                    (SEQ ID NO:4)
5' GCCTTTAATGCTAAAAAATTTAAAAGATTTTCAACCCTCTTAGGATG
C 3'

Using the DNA encoding D1-GFP as template, PCR with the primers HD1-P1 and HD1-NLSF resulted in a product of 1000 bp (PCR#1). Using DNA encoding D1-GFP PCR with primers HD1-P2 and HD1-NLSR resulted in a product of 300 bp (PCR#2). A subsequent PCR carried out with HD1-P1 and HD1-P2 primers resulted in a product of 1300 bp using the product from PCR#1 and the product from PCR#2 as templates. The resulting DNA encoding D1-NLS was subcloned into vector PEGFP at EcoR1 and Kpn1 restriction sites.

All the additional constructs described below were made using the same PCR method and experimental conditions as described above for the D1 dopamine receptor, but with specific primers as described below.

1b. Constructing the Human Dopamine D1 Receptor Containing a NLS and Fused to RFP (D1-NLS-RFP)

The NLS sequence K K F K R was inserted into the helix 8 segment of the intracellular carboxyl tail of the human D1 receptor by PCR method as follows. Using the DNA encoding the human D1 in pcDNA3 vector as template, the first PCR was carried out with HD1-P1 and HD1-NLSR primers resulting in a 1 kb product. A second PCR was done using HD1-P2 and HD1-NLSF primers resulting in a 300 bp product. Using PCR#1 and PCR#2 products as templates, the final PCR was done with HD1-P1 and HD1-P2 primers which generated a 1.3 kp product.

D1NLS was subcloned into vector pDsRed (Clontech) at EcoRI and KpnI and fused to RFP.

Primer Sequences:

HD1-P1:                                      (SEQ ID NO:1)
5' GAGGACTCTGAACACCGAATTCGCCGCCATGGACGGGACTGGGCTG
GTG 3'

HD1-P2:                                      (SEQ ID NO:2)
5' GTGTGGCAGGATTCATCTGGGTACCGCGGTTGGGTGCTGACCGTT 3'

HD1-NLSF:                                    (SEQ ID NO:4)
5' GCCTTTAATGCTAAAAAATTTAAAAGATTTTCAACCCTCTTAGGATG
C 3'

HD1-NLSR:                                    (SEQ ID NO:3)
5' CCTAAGAGGGTTGAAAATCTTTTAAATTTTTTAGCATTAAAGGCATAA
ATG 3'

D1-wildtype:                                 (SEQ ID NO:5)
N P I I Y A F N A D F R K A F S T L L D1NLS-Helix8:                                (SEQ ID NO:6)
N P I I Y A F N A K K F K R F S T L L 1c. Construction of the Dopamine D1 Receptor with a Hemagglutinin (HA) Epitope Tag in the Amino Terminus The HA-Tag is as follows:

Nucleotide sequence:                         (SEQ ID NO:7)
TACCCTTACGACGTGCCGGATTACGCC HA amino acid sequence:                      (SEQ ID NO:8)
Y P Y D V P D Y A The HA epitope tag was inserted into the amino terminal of the human D1 receptor using D1-pcDNA3 as template with the following primers:

P1HA-BamH:                                   (SEQ ID NO:9)
5' ggatccactagtaacggccgccagaccaccATGGGATACCCGTACGACG
TCCCCGACTACGCAAGGACTCTGAACACCTCTGCC 3'

P2-NotI:                                     (SEQ ID NO:10)
5' ggccgccagctgcgagTTCAGGTTGGGTGCTGACCG 3'

The resulting amplified cDNA (1.3 kb) was subcloned into pcDNA3 vector at BamH I and Not I.

```
D1 wildtype:                              (SEQ ID NO:11)
M R T L N T S A M D G T G L V V D1-HA tag:                                (SEQ ID NO:12)
M G Y P Y D V P D Y A R T L N T S A M D G T G L V V
```

1d. Construction of the Human Dopamine D1 Receptor with a HA Epitope and NLS in the Proximal Carboxyl Tail (Helix 8) (D1 HA-NLS)

Primer set for the PCR amplification of DNA encoding D1-NLS (helix 8), using DNA encoding D1-HA as template. Using DNA D1-HA as template with primers T7 and HD1-NLSR primers the resulting amplified DNA was 1000 bp (PCR#1). Using DNA D1-HA as template with primers Sp6 and HD1-NLSR primers the resulting DNA was 300 bp, (PCR#2). Using primers T7 and Sp6 primers and the product of PCR#1 and PCR#2 as templates the resulting DNA was 1300 bp (PCR#3).

```
HD1-NLSR:                                 (SEQ ID NO:3)
5' CCTAAGAGGGTTGAAAATCTTTTAAATTTTTTAGCATTAAAGGCAT
AAATG 3'

HD1-NLSF:                                 (SEQ ID NO:4)
5' GCCTTTAATGCTAAAAAATTTAAAAGATTTTCAACCCTCTTAGGAT
GC 3'
```

The result D1 HA-NLS (helix 8) PCR was blunt-ended into pcDNA3 at EcorV. The correct orientation clone was sequenced.

```
D1-HA wildtype:                           (SEQ ID NO:5)
N P I I Y A F N A D F R K A F S T L L D1HA-NLS (helix 8):                       (SEQ ID NO:6)
N P I I Y A F N A K K F K R F S T L L
```

1e. Construction the Dopamine D1 Receptor with a NLS in Intracellular Loop 3, Fused to GFP (D1-NLS-IC3-GFP)

Primer set for the construction of D1-NLS-IC3-GFP:

```
D1NLSF-IC3:                               (SEQ ID NO:13)
5' GGAAAGTTCTTTTAAGAAGAAGTTCAAAAGAGAAAC 3'

D1-NLSR-IC3:                              (SEQ ID NO:14)
5' GTTTCTCTTTTGAACTTCTTCTTAAAAGAACTTTCC 3'
```

Using D1 pcDNA3 template:

PCR#1: HD1-P1 and D1NLSR-IC3 primers

PCR#2: HD1-P2 and D1NLSF-IC3 primers (500 bp)

PCR#3: HD1-P1 and HD1-P2 primers using PCR#1 and PCR#2 as templates (1.3 kb)

The resulting DNA fragment encoding D1-NLS-IC3 was subcloned into vector pEGFP at EcoR1 and Kpn1.

```
D1-wildtype:                              (SEQ ID NO:15)
Q P E S S F K M S F K R E T K V L D1-NLS-IC3:                               (SEQ ID NO:16)
Q P E S S F K K K F K R E T K V L
```

The NLS sequence KKFKR was inserted into the IC loop 3 segment of the D1 receptor replacing the sequence MFSKR, using D1 pcDNA3 as template.

Using the DNA encoding D1 in pcDNA3 as template, PCR was carried out with the following primers HD1-P1 and D1-NLSR-IC3 resulting in a product of 800 bp (PCR#1). Using DNA encoding D1 in pcDNA3 with primers HD1-P2 and HD1-NLSF-IC3 resulted in a product of 500 bp (PCR#2). A subsequent PCR carried out with HD1-P1 and HD1-P2 primers resulted in a product of 1300 bp using the product from PCR#1 and the product from PCR#2 as templates. The resulting construct encoding D1-NLS was subcloned into vector pEGFP at EcoR1 and Kpn1 restriction sites.

1f. Construction of Human D1 Dopamine Receptor with a NLS in Intracellular Loop 2 fused with GFP (D1-NLS-IC2-GFP)

The primer set for the construction of DNA encoding D1NLS-IC2

```
D1NLSF-IC2:                               (SEQ ID NO:17)
5' CCGGTATGAGAAAAAGTTTAAACGCAAGGCAGCCTTC 3'

D1-NLSR-IC2:                              (SEQ ID NO:18)
5' GGCTGCCTTGCGTTTAAACTTTTTCTCATACCGGAAAGG 3'
```

Using DNA encoding D1 dopamine receptor in pcDNA3 as template, PCR with the primers HD1-P1 and D1NLSR-IC2 (PCR#1), resulted in a product of 500 bp. Using DNA encoding D1 dopamine receptor in pcDNA3 as a template with primers HD1-P2 and D1NLSF-IC2 (PCR#2) resulted in a product of 800 bp. A subsequent PCR carried out with primers HD1-P1 and HD1-P2 using PCR#1 and PCR#2 as templates resulted in a product of 1300 bp.

The resulting DNA encoding D1NLS-IC2 PCR was subcloned into vector EGFP at EcoR1 and Kpn1.

```
D1-wildtype:                              (SEQ ID NO:19)
N P F R Y E R K M T P K A A F I L I D1-NLS-IC2:                               (SEQ ID NO:20)
N P F R Y E K K F K R K A A F I L I
```

1g. Construction of the Human D1 Dopamine Receptor with a NLS in Intracellular Loop 1 Fused with GFP (D1-NLS-IC1-GFP)

The primer set for the construction of DNA encoding D1-NLS-IC1.

```
D1-NLSF-IC1:                              (SEQ ID NO:21)
5' GTGCTGCCGTTAAAAAGTTCAAACGCCTGCGGTCCAAGG 3'

D1-NLSR-IC1:                              (SEQ ID NO:22)
5' GGACCGCAGGCGTTTGAACTTTTTAACGGCAGCACAGACC 3'
```

Using the DNA encoding D1 dopamine receptor in pcDNA3 as template, PCR with the primers HD1-P1 and D1-NLSR-IC1 (PCR#1), resulted in a product of 300 bp. Using DNA encoding D1 dopamine receptor in pcDNA3 as template PCR with primers HD1-P2 and D1NLSF-IC1 resulted in a product of 1000 bp (PCR#2). A subsequent PCR carried out with primers HD1-P1 and HD1-P2 using PCR#1 and PCR#2 as templates resulted in a product of 1300 bp.

The resulting DNA encoding D1-NLS-IC1 was subcloned into vector PEGFP at EcoR1 and Kpn1.

```
D1-wildtype:                              (SEQ ID NO:23)
L V C A A V I R F R H L R S K V T N D1-NLS-IC1:                               (SEQ ID NO:24)
L V C A A V K K F K R L R S K V T N
```

1h. Construction of Human Dopamine D1 Receptor with an Alternate NLS in the Proximal Carboxyl Tail and Fused to GFP (D1-NLS2-GFP)

The PCR method was used to introduce the NLS sequence PKKKRKV (SEQ ID NO: 129) in replacement of the natural sequence ADFRKAF in the D1 receptor. The DNA encoding the D1 dopamine receptor in pcDNA3 was subjected to PCR with the primers HD1-P1 and HD1-NLS2R, resulting in a product of 1 kb (PCR#1). Another PCR using D1 in pcDNA3 with primers HD1-P2 and HD1-NLS2F resulted in a product of 300 bp (PCR#2). The third PCR using PCR#1 and PCR#2 as templates HD1-P1 and HD1-P2 primers resulted in a product of 1.3 kb, and was subcloned into vector PEGFP at EcoR1 and Kpn1.

```
HD1-NLS2F:                                   (SEQ ID NO:25)
5' GCCTTTAATCCTAAAAAAAAAAGAAAGGTTTCAACCCTCTTAGG 3'

HD1-NLS2R:                                   (SEQ ID NO:26)
5' CCTAAGAGGGTTGAAACCTTTCTTTTTTTTTTAGGATTAAAGGC 3'

D1-wildtype:                                 (SEQ ID NO:27)
N P I I Y A F N A D F R K A F S T L L D1-NLS2:                                     (SEQ ID NO:28)
N P I I Y A F N P K K K R K V S T L L
```

2. Construction the Dopamine D2 and D2-NLS Dopamine Receptors Fused to GFP (D2-GFP and D2-NLS-GFP)

Primer set for amplification of the DNA in pcDNA3 encoding the D2-dopamine receptor.

```
HD2-P1:                                      (SEQ ID NO:29)
5' GGCCGTGGCTCCACCGAATTCGCCGCCATGGATCCACTGAATCTG 3'

HD2-P2:                                      (SEQ ID NO:30)
5' CTGTGCGGGCAGGCAGGGTACCGCGCAGTGGAGGATCTTCAGG 3'
```

The restriction site EcoR1 was incorporated into primer HD2-P1, and the restriction site Kpn1 was incorporated into primer HD2-P2. The D2-PCR product, which contained no stop codon, was unidirectionally subcloned into vector pEGFP (Clontech) at EcoR1 and Kpn1 and inframe with the start codon of the GFP protein.

Primer set for the construction of D2-NLS-GFP

```
HD2-NLSF:                                    (SEQ ID NO:31)
5' CACCACCTTCAACAAAAAATTCAAAAGAGCCTTCCTGAAGATCC 3'

HD2-NLSR:                                    (SEQ ID NO:32)
5' GGATCTTCAGGAAGGCTCTTTTGAATTTTTTGTTGAAGGTGGTG 3'
```

The NLS sequence KKFKR was inserted into the base of TM7 segment of the D2 receptor replacing the sequence IEFRK, using D2-GFP DNA construct as template.

Using the DNA encoding D2-GFP as template, PCR was carried out with the following primers HD2-P1 and HD2-NLSR resulting in a product of 1300 bp (PCR#1). Using DNA encoding D2-GFP PCR with primers HD2-P2 and HD1-NLSF resulted in a product of 100 bp (PCR#2). A subsequent PCR carried out with HD2-P1 and HD2-P2 primers resulted in a product of 1400 bp using the product from PCR#1 and the product from PCR#2 as templates. The resulting construct encoding D2-NLS was subcloned into vector pEGFP at EcoR1 and Kpn1 restriction sites.

3. Construction of DNA Encoding the D3 and D5 Dopamine Receptors Fused to GFP (D3-GFP and D5-GFP)

Primer set for amplification of the DNA in pcDNA3 encoding the D3-dopamine receptor.

```
HD3-Hind:                                    (SEQ ID NO:33)
5' GGCATCACGCACCTCAAGCTTGCCGCCATGGCATCTCTGAGTCAGC 3'

HD3-Kpn:                                     (SEQ ID NO:34)
5' GAGTGTTCCCTCTTCTGCGGTACCGCGCAAGACAGGATCTTGAGG 3'
```

The restriction site HindIII was incorporated into primer HD3-Hind, and the restriction site KpnI and was incorporated into primer HD3-Kpn. The D3-PCR product, which contained no stop codon, was unidirectionally subcloned into vector pEGFP at HindIII and KpnI and inframe with the start codon of the GFP protein.

Primer set for amplification of the DNA in pcDNA3 encoding the D5 dopamine receptor.

```
T7:                                          (SEQ ID NO:35)
5' AATACGACTCACTATAG 3'

HD5-Kpn:                                     (SEQ ID NO:36)
5' CGCCAGTGTGATGGATAATGGTACCGCATGGAATCCATTCGGGGTG 3'
```

The restriction site KpnI and was incorporated into primer HD5-Kpn. The D5-PCR product, which contained no stop codon, was unidirectionally subcloned into vector pEGFP at EcoRI and KpnI and inframe with the start codon of the GFP protein.

4. Construction of the Histamine1 and Histamine1-NLS Receptors Fused to GFP (H1-GFP and H1-NLS-GFP)

Primer set for amplification of the DNA, from human genomic DNA, encoding the encoding the H1 histamine receptor.

```
H1-MET:                                      (SEQ ID NO:37)
5' GCGCCAATGAGCCTCCCCAATTCC 3'

H1-STOP:                                     (SEQ ID NO:38)
5' GAGCCTCCCTTAGGAGCGAATATGC 3'
```

This H1-PCR product was used as a template for the subsequent PCR experiment.

Primer set for amplification of the DNA encoding the H1-GFP construct.

```
H1-PST:                                      (SEQ ID NO:39)
5' CGCCTGCAGGCCGCCATGAGCCTCCCCAATTCCTCC 3'

H1-APA:                                      (SEQ ID NO:40)
5' CCGGTGGATCCCGGGCCCCGGAGCGAATATGCAG 3'
```

The restriction site PstI was incorporated into primer H1-PST, and the restriction site ApaI was incorporated into primer H1-APA. This H1-PCR product, which contained no stop codon, was unidirectionally subcloned into vector PEGFP at PstI and ApaI and inframe with the start codon of the GFP protein.

Primer set for amplification of the DNA encoding the H1-NLS-GFP

```
H1-NLSR:                                     (SEQ ID NO:41)
5' GGGCCCCGGAGCGAATATGCAGAATTCTCTTGAATGTCCTCTTGAATT
TTTTATTGCACAAGG 3'
```

The NLS sequence: KKFKR was inserted into the DNA encoding the TM7 segment of the H1 receptor by the PCR method, using the H1-GFP template, replacing the sequence ENFKK. PCR with H1-PST and H1-NLSR primers gave a product of 1500 bp. The resulting fragment encoding H1-NLS was subcloned into vector PEGFP at PstI and ApaI restriction sites.

5. Construction the Cysteinyl Leukotriene Receptor 1 and CysLT1-NLS Fused to GFP (CysLT1-GFP and CysLT1-NLS-GFP).

Primer set for amplification of the DNA in pcDNA3 encoding the CysLT1 receptor.

LT1-EcorI:                                  (SEQ ID NO:42)
5' AAGAATTCGCCACCATGGATGAAACAGGAAATCTG 3'

LT1-KpnI:                                   (SEQ ID NO:43)
5' GGGTACCGCTACTTTACATATTTCTTCTCC 3'

The restriction site EcoR1 was incorporated into primer LT1-EcoRI and the restriction site Kpn1 was incorporated into primer LT1-KpnI. The CysLT1-PCR DNA product, which contained no stop codon, was unidirectionally subcloned into vector PGFP at EcoR1 and Kpn1 and inframe with the start codon of the GFP protein.

Primer set for amplification of the DNA encoding the CysLT1-NLS-GFP

LT1-NLSF:                                   (SEQ ID NO:44)
5' TTCTTTTCTGGGAAAAAATTTAAGAGAAGGCTGTCTAC 3'

LT1-NLSR:                                   (SEQ ID NO:45)
5' TGTAGACAGCCTTCTCTTAAATTTTTTCCCAGAAAAG 3'

The NLS sequence KKFKR was inserted into the DNA encoding the TM7 segment of the CysLT1 by PCR, using DNA encoding the CysLT1-GFP as template, replacing the sequence GNFRK. Using the DNA encoding CysLT1-GFP as template, PCR with the following primers LT1-EcoRI and LT1-NLSR resulted in a fragment of 900 bp (PCR#1). Using DNA encoding CysLT1-GFP PCR with primers LT1-KpnI and LT1-NLSF resulted in a fragment of 100 bp (PCR#2). A subsequent PCR carried out with LT1-EcoRI and LT1-KpnI primers resulted in a product of 1000 bp using the product from PCR#1 and the product from PCR#2 as templates. The resulting DNA encoding CysLT1-NLS was subcloned into vector PEGFP at EcoR1 and Kpn1 restriction sites.

6. Construction of the Cysteinyl Leukotriene Receptor CysLT2 and CysLT2-NLS Fused to GFP (CysLT2-GFP and CysLT2-NLS-GFP)

Primer set for amplification of the DNA in pcDNA3 encoding the CysLT2 receptor.

LT2-EcoRI:                                  (SEQ ID NO:46)
5' CTTTTTGTGTCTGTTTCTGAATTCGCCACCATGGAGAGAAAATTTATG 3'

LT2-KpnI:                                   (SEQ ID NO:47)
5' GAACAGGTCTCATCTAAGAGGTACCGCTACTCTTGTTTCCTTTCTC 3'

The restriction site EcoR1 was incorporated into primer LT2-EcoRI, and the restriction site Kpn1 was incorporated into primer LT2-KpnI. The CysLT2 product, which contained no stop codon, was unidirectionally subcloned into vector pEGFP at EcoR1 and Kpn1 and inframe with the start codon of the GFP protein.

Primer set for the amplification of the CysLT2-NLS-GFP

LT2-NLSF:                                   (SEQ ID NO:48)
5' GCTGGGAAAAAATTTAAAAGAAGACTAAAGTCTGCAC 3'

LT2-NLSR:                                   (SEQ ID NO:49)
5' GTCTTCTTTTAAATTTTTTCCCAGCAAAGTAATAGAGC 3'

The NLS sequence KKFKR was inserted into the TM7 segment of the CysLT2 by PCR method replacing the sequence ENFKD. Using the DNA encoding CysLT2-EGFP as template, a PCR with the following primers LT2-EcoR1 and LT2-NLSR primers resulted in a fragment of 900 bp (PCR#1). Using DNA encoding LT2-KpnI and LT2-NLSF primers a PCR resulted in a fragment of 200 bp (PCR#2). A subsequent PCR carried out with LT2-EcoR1 and LT2-KpnI primers using the product of PCR#1 and the product of PCR#2 as templates resulted in a product of 1100 bp. The resulting DNA encoding CysLT2-NLS was subcloned into vector pEGFP at EcoR1 and Kpn1 restriction sites.

7. Construction of the M1 Muscarinic Receptor and the Muscarinic NLS Receptor Fused to GFP (M1-GFP and M1-NLS-GFP)

Primer set for amplification of the DNA encoding the muscarinic receptor (M1) from human genomic DNA.

M1-MET:                                     (SEQ ID NO:50)
5' CCCCACCTAGCCACCATGAACACTTC 3'

M1-STOP:                                    (SEQ ID NO:51)
5' GGGGACTATCAGCATTGGCGGGAGG 3'

Primer set for MR1-EGFP

M1-PST:                                     (SEQ ID NO:52)
5' CCCCACCTGCAGCCACCATGAACACTTCAGCC 3'

M1-BAMH:                                    (SEQ ID NO:53)
5' GGGGAGGATCCGCGCATTGGCGGGAGGGAGTGC 3'

The restriction site PstI was incorporated into primer M1-PST, and the restriction site BamHI was incorporated into primer M1-BAMH. The M1 PCR product, which contained no stop codon, was unidirectionally subcloned into vector PEGFP at PstI and BamHI and inframe with the start codon of the EGFP protein.

Primer set for M1-NLS EGFP

M1-NLSF:                                    (SEQ ID NO:54)
5' CGCACTCTGCAACAAAAAATTCAAACGCACCTTTCGCC 3'

M1-NLSR:                                    (SEQ ID NO:55)
5' GGCGAAAGGTGCGTTTGAATTTTTTGTTGCAGAGTGCG 3'

The NLS sequence KKFKR was inserted into the TM7 segment of the M1 by PCR, using the MR1 template, replacing the sequence KAFRD. Using the DNA encoding MR1 as template, PCR with the following primers using M1-PST and M1-NLSR resulted in a product of 1200 bp (PCR#1). Using DNA encoding MR1 a PCR with primers reaction using M1-BAMH and M1-NLSF primers resulted in a product of 100 bp (PCR#2). A subsequent PCR carried out with M1-PST and ML-BAMH primers resulted in a product of 1300 bp using the product from PCR#1 and the product from PCR#2 as templates. This fragment encoding MR1-NLS was subcloned into vector PEGFP at PstI and BamHI restriction sites.

8. Construction of the Serotonin (5HT1B) and the Serotonin NLS Receptors Fused to GFP (5HT1B-GFP and 5HT1B-NLS-GFP)

Primer set for amplification of the DNA encoding the 5HT1B receptor from the plasmid pcDNA3 encoding the 5HT1B receptor.

```
5HT1B-E1:                                       (SEQ ID NO:56)
5' GGGGCGAATTCGCCGCCATGGAGGAACCGGGTGC 3'

5HT1B-KPN:                                      (SEQ ID NO:57)
5' GCAAACGGTACCGCACTTGTGCACTTAAAACGTA 3'
```

The restriction site EcoR1 was incorporated into primer 5HT1B-E1 and the restriction site Kpn1 was incorporated into primer 5HT1B-KPN. The 5HT1B-PCR product, which contained no stop codon, was unidirectionally subcloned into vector PEGFP at EcoR1 and Kpn1 and inframe with the start codon of the GFP protein.

Primer set for 5HT1B-NLS EGFP

```
5HT1B-NLSF:                                     (SEQ ID NO:58)
5' ATGTCCAATAAAAAATTTAAAAGAGCATTCCATAAACTG 3'

5HT1B-NLSR:                                     (SEQ ID NO:59)
5' GGAATGCTCTTTTAAATTTTTTATTGGACATGGTATAG 3'
```

The NLS sequence: KKFKR was inserted into the TM7 segment of the 5HT1B by PCR using 5HT1B-EGFP template, replacing the sequence EDFKQ. Using the DNA encoding 5HT1B-EGFP as template, a PCR with the following primers with 5HT1B-E1and HD1-NLSF primers gave a product of 1100 bp (PCR#1). Using DNA encoding 5HT1B-EGFP with 5HT1B-KPN and HD1-NLSR primers resulted in a product of 100 bp (PCR#2). A subsequent PCR carried out with 5HT1B-E1 and 5HT1B-KPN primers resulted in a product of 1200 bp using the product from PCR#1 and the product from PCR#2 as templates. The resulting DNA encoding 5HT1B-NLS was subcloned into vector PEGFP at EcoR1 and Kpn1 restriction sites.

9. Construction of the beta2-adrenergic (beta2-AR) and the beta2-AR-NLS1 Receptors Fused to GFP (beta2-AR-GFP and beta2AR-NLS1-GFP)

Primer set for amplification of the DNA encoding the beta2-AR receptor from pcDNA3.

```
T7:                                             (SEQ ID NO:60)
5' AATACGACTCACTATAG 3'

Beta2-Kpn:                                      (SEQ ID NO:61)
5' GCCGCCAGTGTGATGGATACTGGTACCGCTAGCAGTGAGTCATTT
GTAC 3'
```

The restriction site Kpn1 was incorporated into primer beta2-Kpn. The beta 2-AR product, which contained no stop codon, was unidirectionally subcloned into vector pEGFP at EcoR1 and Kpn1 and inframe with the start codon of the GFP protein.

The NLS sequence KKFKR was inserted into the TM7 segment of the beta2-AR by PCR using beta2-AR-EGFP template, replacing the sequence PDFRI. Using the DNA encoding beta2-AR-EGFP as template, a PCR with the following primers with T7 and B2-NLSR primers resulted in a product of 1100 bp (PCR#1). Using DNA encoding beta2-AR-EGFP with beta2-Kpn and B2-NLSF primers resulted in a product of 300 bp (PCR#2). A subsequent PCR carried out with primers T7 and beta2-Kpn resulted in a product of 1300 bp using the product from PCR#1 and the product from PCR#2 as templates. The resulting DNA encoding beta2-NLS was subcloned into vector pEGFP at EcoR1 and Kpn1 restriction sites.

10. Construction of the beta 2-adrenergic Receptor with an Alternate NLS and Fused to GFP (beta2-NLS2-GFP)

Primer set for amplification of the DNA encoding the beta2-NLS2 receptor from pcDNA3.

```
B2D1NLSF:                                       (SEQ ID NO:62)
5' CCCCTTATCTACGCCTTTAGCGCAAAGAAGTTCAAGCGC 3'

B2D1NLSR:                                       (SEQ ID NO:63)
5' GCGCTTGAACTTCTTTGCGCTAAAGGCGTAGATAAGGGG 3'
```

Using the DNA encoding beta2-AR-GFP as template, a PCR with the following primers with T7 and B2D1NLSR primers resulted in a product of 1000 bp (PCR#1). Using DNA encoding beta2-AR-GFP with beta2-Kpn and B2D1NLSF primers resulted in a product of 300 bp (PCR#2). A subsequent PCR carried out with primers T7 and beta2-Kpn primers using PCR#1 and PCR#2 as templates resulted in a product of 1300 bp. The resulting DNA encoding beta2-NLS2 was subcloned into vector pEGFP at EcoR1 and Kpn1 restriction sites.

The NLS sequence AFSAKKFKR (SEQ ID NO: 158) was inserted into the TM7 segment of the beta2-AR by PCR using beta2-GFP template, replacing the sequence CRSPDFRIA.

The resulting DNA encoding beta2-NLS2 was subcloned into vector pEGFP at EcoR1 and Kpn1 restriction sites.

11. Construction of the beta 2-adrenergic Receptor with an Alternate NLS and Fused to GFP (beta2-NLS3-GFP)

The NLS sequence K K F K R (SEQ ID NO: 129) was inserted into another location of the proximal segment of the carboxyl tail of the beta2-AR. Using the DNA encoding the beta2AR in pcDNA3 vector as template, PCR was carried out with T7 and r B2-NLS3R primers resulting a 1000 bp product. PCR using primers Beta2-Kpn and B2-NLS3F resulted in a 300 bp product. Using PCR#1 and PCR#2 products as templates PCR with T7 and Beta2-Kpn primers generated a 1300 bp product (beta2AR-NLS3) which was subcloned into vector PEGFP at EcoR1 and Kpn1.

Primer set for Beta2-NLS3-GFP

```
B2-NLS3F:                                       (SEQ ID NO:64)
5' CTGCCGGAGCAAAAAATTCAAAAGAGCCTTCCAGGAGC 3'

B2-NLS3R:                                       (SEQ ID NO:65)
5' CCTGGAAGGCTCTTTTGAATTTTTTGCTCCGGCAGTAG 3'

Wildtype Beta2:                                 (SEQ ID NO:66)
N P L I Y C R S P D F I R A F Q E L L Beta2AR-NLS3:                                   (SEQ ID NO:67)
N P L I Y C R S K K F K R A F Q E L L
```

12. Construction of the Dopamine Transporter Fused to GFP (DAT-GFP)

The full length cDNA encoding the human dopamine transporter (hDAT) was amplified using DAT in pcDNA3 as template by PCR with primer T7 and primer DT-1 (5' CGTCTCTGCTCCCTGGTACCGCCACCT-TGAGCCAGTGG 3': SEQ ID NO: 68). This PCR product contained no stop codon and was unidirectionally subcloned into vector pEGFP (from Clontech) at the EcoR1 and Kpn1 restriction sites and inframe with the start codon of the GFP protein.

13a. Construction of the Human Dopamine Transporter Containing a NLS and Fused to RFP (DAT-NLS-RFP)

The cDNA encoding the human dopamine transporter (hDAT) was amplified by PCR with 1718 and hDAT-NLSF primers, producing a fragment of 100 bp. The cDNA encoding the human dopamine transporter (hDAT) was also amplified by PCR with T7 and hDAT-NLSR primers, producing a fragment of 1.7 kB. These two PCR fragments were used as templates with T7 and 1718 primers, resulting in a fragment of 1.8 kB.

```
Primer T7:                              (SEQ ID NO:69)
5' TAATACGACTCACTATAGGG 3'

Primer 1718:                            (SEQ ID NO:70)
5' CGTCTCTGCTCCCTGGTACCGCCACCTTGAGCCAGTGG 3' hDAT-NLSF:                              (SEQ ID NO:71)
5' CTATGCGGCCAAAAAGTTCAAAAGACTGCCTGGGTCC 3' hDAT-NLSR:                              (SEQ ID NO:72)
5' CAGGCAGTCTTTTGAACTTTTTGGCCGCATAGATGGGC 3'
```

This PCR product was unidirectionally subcloned into vector pRFP at EcoR1 and Kpn1 and inframe with the start codon of the RFP protein.

The resulting PCR fragment encoded the NLS sequence K K F K R after TM12 as follows:

```
DAT-wild type:                          (SEQ ID NO:73)
S S M A M V P I Y A A Y K F C S L P G S F R E K DAT-NLS:                                (SEQ ID NO:74)
S S M A M V P I Y A A K K F K R L P G S F R E K
```

13b. Construction of the Human Dopamine Transporter with a NLS and Fused to GFP (DAT-NLS-GFP)

The NLS sequence K K F K R was inserted into the proximal carboxyl tail following the transmembrane 12 segment of the human DAT. Using the DNA encoding the human DAT-cDNA in pcDNA3, as template, the first PCR was carried out with T7 and hDAT-NLSR primers resulting a 1.7 kb product. A second PCR was done using 1718 and hDAT-NLSF primers resulting in a 100 bp product, then using PCR#1 and PCR#2 products as templates the final PCR was done with T7 and 1718 primers which generated a 1.8 kp product (DAT-NLS) which was subcloned into vector pEGFP (Clontech) at EcoR1 and Kpn1 and fused GFP.

Sequences of the Primers:

```
hDAT-NLSF:                              (SEQ ID NO:75)
5' CTATGCGGCCAAAAAGTTCAAAAGACTGCCTGGGTCC 3' hDAT-NLSR:                              (SEQ ID NO:76)
5' CAGGCAGTCTTTTGAACTTTTTGGCCGCATAGATGGGC 3'

Human DAT wildtype:                     (SEQ ID NO:77)
S S M A M V P I Y A A Y K F C S L P G S F R E K Human DAT-NLS:                          (SEQ ID NO:78)
S S M A M V P I Y A A K K F K R L P G S F R E K
```

14. Construction of the Human Serotonin Transporter Fused to GFP (SERT-GFP)

The full length human SERT cDNA was isolated by PCR from pcDNA3 containing the SERT cDNA, using the two following primers:

```
SERT-HIND:                              (SEQ ID NO:79)
5' GTCATTTACTAAGCTTGCCACCATGGAGACGACGCCCTTG 3'

SERT-KPN:                               (SEQ ID NO:80)
5' CCTCTCGGTGAGTGGTACCGCCACAGCATTCAAGCGG 3'
```

This PCR product contained no stop codon and was unidirectionally subcloned into vector pEGFP (Clontech) at HindIII and KpnI and inframe with the start codon of the GFP protein.

15. Construction of the Human Low Density Lipoprotein Receptor Fused to GFP (LDL-R-GFP)

The full length cDNA encoding LDL was subjected to PCR with LDLR-HIND and LDLR-KPN primers:

```
LDLR-HIND:                              (SEQ ID NO:81)
5' GGACACTGCCTGGCAAAGCTTGCGAGCATGGGGCCCTGG 3'

LDLR-KPN:                               (SEQ ID NO:82)
5' GGCGGGACTCCAGGCAGGTACCGCCGCCACGTCATCCTCC 3'
```

This PCR product (2600 bp) contained no stop codon and was unidirectionally subcloned into vector pEGFP (Clontech) at HindIII and KpnI and inframe with the start codon of the GFP protein.

16. Construction of the Human Low Density Lipoprotein Receptor with a NLS and Fused to GFP (LDLR-NLS-GFP)

The NLS sequence KKFKR was inserted into DNA encoding the LDL receptor by PCR, replacing the natural sequence coding for RLKNI.

The primer set for the construction of DNA encoding LDL-NLS:

```
LDL-NLSF:                               (SEQ ID NO:83)
5' CTATGGAAGAACTGGAAAAAATTTAAAAGAAACAGCATCAAC 3'

LDL-NLSR:                               (SEQ ID NO:84)
5' CAAAGTTGATGCTGTTTCTTTTAAATTTTTTCCAGTTCTTCC 3'
```

Using the human DNA encoding LDL cDNA in pcDV1 as template, PCR with the primers LDLR-HIND and LDL-NLSR resulted in a product of 2450 bp (PCR#1). Using DNA encoding LDL as a template with primers LDLR-KPN and LDL-NLSF resulted in a product of 150 bp (PCR#2). A subsequent PCR carried out with primers LDLR-HIND and LDLR-KPN using the product of PCR#1 and PCR#2 as template resulted in a product of 2600 bp.

The resulting PCR contained the NLS sequence K K F K R mutation as follows:

```
Human LDL-R wildtype:                   (SEQ ID NO:85)
F L L W K N W R L K N I N S I N F D N P Human LDL-R:                            (SEQ ID NO:86)
F L L W K N W K K F K R N S I N F D N P
```

This PCR product contained no stop codon and was unidirectionally subcloned into vector PEGFP (Clontech) at HindIII and KpnI and inframe with the start codon of the GFP protein.

17. Construction of the Epidermal Growth Factor Receptor Fused to GFP (EGFR-GFP)

The full length human EGFR cDNA in Prkf vector was isolated by PCR with the two following primers:

```
HER-XHO:                                (SEQ ID NO:87)
5' GCTCTTCGGGCTCGAGCAGCGATGCGACCCTCCGGGACGG 3'

HER-KPN:                                (SEQ ID NO:88)
5' CTATCCTCCGTGGTACCGCTGCTCCAATAAATTCACTGC 3'
```

This PCR product (3600 bp) contained no stop codon and was unidirectionally subcloned into vector pEGFP (Clontech) at XhoI and KpnI and inframe with the start codon of the GFP protein.

18. Construction of the Human Serotonin Transporter with a NLS and Fused to GFP (SERT-NLS-GFP)

The NLS sequence KKFKR was inserted into DNA encoding the SERT by PCR, replacing the natural sequence coding for GTFKE.

The primer set for the amplification of the DNA encoding SERT-NLS.

```
SERT-NLSF:                             (SEQ ID NO:89)
5' GATCATCACTCCAAAGAAATTTAAAAGACGTATTATT 3'

SERT-NLSR:                             (SEQ ID NO:90)
5' TAATACGTCTTTTAAATTTCTTTGGAGTGATGATCAACCG 3'
```

Using the human SERT-cDNA in PcDNA3 as template, PCR with the primers SERT-HIND and SERT-NLSR resulted in a product of 1800 bp (PCR#1). Using DNA encoding SERT as a template with primers SERT-KPN and SERT-NLSF resulted in a product of 100 bp (PCR#2). A subsequent PCR carried out with primers SERT-HIND and SERT-KPN primers using the product of PCR#1 and PCR#2 as template resulted in a product of 1900 bp.

The resulting PCR product encoded the NLS sequence K K F K R mutation after TM12 of the SERT as follows:

```
Human SERT wildtype:                   (SEQ ID NO:91)
R L I I T P G T F K E R I I K S I T Human SERT:                            (SEQ ID NO:92)
R L I I T P K K F K R R I I K S I T
```

This PCR product contained no stop codon and was unidirectionally subcloned into vector pEGFP (Clontech) at HindIII and KpnI and inframe with the start codon of the GFP protein.

19. Construction of the Metabotropic glutamate-4-receptor Fused to GFP, with and without NLS (mGluR4-GFP and mGluR4-NLS-GFP)

The DNA encoding mGluR4 was isolated from a rat cDNA using the primer set

```
GLUR4-HIND:                            (SEQ ID NO:93)
5' GGGTCTCTAAGCTTGCCGCCATGTCCGGGAAGGG 3'

GLUR4-ECORI:                           (SEQ ID NO:94)
5' CCGCGGCCCGGAATTCGGATGGCATGGTTGGTG 3'
```

A restriction site HindIII was incorporated into primer GLUR4-HIND, and a restriction site EcoRI was incorporated into primer GLUR4-ECORI. The mGluR4-PCR product, which contained no stop codon, was unidirectionally subcloned into vector EGFP (Clontech) at HindIII and EcorI and inframe with the start codon of the GFP protein.

The NLS KKFKR was introduced into the DNA encoding the mGluR4 replacing the natural sequence KRKRS.

Primer set for the amplification of the DNA to introduce the NLS into the Rat mGluR4-EGFP

```
GLUR4-NLSF:                            (SEQ ID NO:95)
5' CGTGCCCAAGAAATTCAAGCGCCTCAAAGCCGTGGTC 3'

GLUR4-NLSR:                            (SEQ ID NO:96)
5' CGGCTTTGAGGCGCTTGAATTTCTTGGGCACGTTCTGC 3'
```

Using the rat DNA encoding GluR4 as template PCR with the primers GLUR4-HIND and GLUR4-NLSR resulted in a product of 2600 bp (PCR#1). Using DNA encoding GluR4 with primers GLUR4-ECORI and GLUR4-NLSF resulted in a product of 160 bp (PCR#2). A subsequent PCR carried out using the product of PCR#1 and PCR#2 as template, with primers: GLUR4-HIND and GLUR4-ECORI, resulted in a product of 2760 bp.

The resulting PCR contained the NLS sequence K K F K R mutation as follows:

```
Rat mGluR4 Wildtype:                   (SEQ ID NO:97)
F H P E Q N V P K R K R S L K A V V T A A T Rat mGluR4:                            (SEQ ID NO:98)
F H P E Q N V P K K F K R L K A V V T A A T
```

This PCR product was unidirectionally subcloned into vector pEGFP (Clontech) at HindIII and EcoRI and inframe with the start codon of the GFP protein.

20. Construction of the Human Insulin Receptor Fused to GFP (IR-GFP)

The full length IR cDNA in plasmid pRK5 was isolated with the two PCR primers:

```
HIR-HIND:                              (SEQ ID NO:99)
5' GGAGACCCCAAGCTTCCGCAGCCATGGGCACCGGGGGCC 3'

HIR-APA:                               (SEQ ID NO:100)
5' CCCCGCCACGGGCCCCGGAAGGATTGGACCGAGGCAAGG 3'
```

The PCR product (4.2 kb) contained no stop codon and was unidirectionally subcloned into vector pEGFP (Clontech) at HindIII and ApaI and fused to the GFP protein.

21. Construction of the Human Insulin Receptor with a NLS and Fused to GFP (IR-NLS-GFP)

The NLS sequence KKFKR was introduced into the human insulin receptor to replace the sequence LYASS.

Using the human insulin receptor cDNA in pRK5 vector as template, the first PCR #1 with HIR-HIND and HIR-NLSR primers generated a 2.9 kb product, the second PCR #2 with HIR-APA and HIR-NLSF primers generated a 1.3 kb product, and then using the products from PCR#1 and PCR #2 as templates, the third PCR #3 produced a fragment with HIR-HIND and HIR-APA primers (4.2 kb). This contained no stop codon and was unidirectionally subcloned into vector PEGFP at HindIII and ApaI and thus fused to the GFP protein.

Primers for HIR-NLS:

```
HIR-NLSF:                              (SEQ ID NO:101)
5' CCGCTGGGACCGAAAAAATTTAAGAGAAACCCTGAGTATCTC 3'

HIR-NLSR:                              (SEQ ID NO:102)
5' GATACTCAGGGTTTCTCTTAAATTTTTTCGGTCCCAGCGGCCC 3'
```

22. Construction of the Human Erythropoietin Receptor Fused to GFP (EPO-GFP).

Using PCR method and the cDNA in pc3.1 vector encoding the human Erythropoietin receptor (EPO) as template, the full length cDNA was isolated with the following primers:

```
T7:                                    (SEQ ID NO:103)
5' TAATACGACTCACTATAGGG 3'

EPO-KPN:                               (SEQ ID NO:104)
5' GACTGCAGCCTGGTGGTACCGCAGAGCAAGCCACATAGCTGGGG 3'
```

This PCR product (1.6 kb) contained no stop codon and was unidirectionally subcloned into vector pEGFP at HindIII and KpnI and fused to the GFP protein.

23. Construction of the Human Erythropoietin Receptor with a NLS and Fused to GFP (EPO-NLS-GFP).

The NLS sequence KKFKR was inserted into the DNA encoding the EPO receptor by PCR, replacing its natural sequence RRALK.

Using the human EPO-cDNA in pc3.1 as template, the first PCR #1 with T7 and EPO-NLSR primers generated a 900 bp product, the second PCR #2 with EPO-KPN and EPO-NLSF primers generated a 700 bp product, and then using the products from PCR#1 and PCR #2 as templates, the third PCR #3 with T7 and EPO-KPN primers produced a 1.6 kb fragment. This PCR product (1.6 kb) contained no stop codon and was unidirectionally subcloned into vector pEGFP at HindIII and KpnI and thus fused to the GFP protein.

Primer Sequences:

```
T7:                                  (SEQ ID NO:105)
5' TAATACGACTCACTATAGGG 3'

EPO-KPN:                             (SEQ ID NO:106)
5' GACTGCAGCCTGGTGGTACCGCAGAGCAAGCCACATAGCTGGGG 3'

EPO-NLSF:                            (SEQ ID NO:107)
5' GCTGCTCTCCCACAAAAAGTTTAAGCGGCAGAAGATCTGG 3'

EPO-NLSR:                            (SEQ ID NO:108)
5' CCAGATCTTCTGCCGCTTAAACTTTTTGTGGGAGAGCAGC 3'

Human EPO wildtype:                  (SEQ ID NO:109)
T V L A L L S H R R A L K Q K I W P G I P Human EPO NLS:                       (SEQ ID NO:110)
T V L A L L S H K K F K R Q K I W P G I P
```

24. Construction of the Human Epidermal Growth Factor Receptor Fused to GFP (EGFR-GFP)

Using the human epidermal growth factor receptor cDNA in Prk5 vector as template, the full length cDNA was isolated by PCR with the two following primers:

```
HER-XHO                              (SEQ ID NO:111)
(5' GCTCTTCGGGCTCGAGCAGCGATGCGACCCTCCGGGACGG 3')
and HER-KPN                              (SEQ ID NO:112)
(5' CTATCCTCCGTGGTACCGCTGCTCCAATAAATTCACTGC 3')
```

This PCR product (3.6 kb) contained no stop codon and was unidirectionally subcloned into vector pEGFP (Clontech) at XhoI and KpnI and fused to the GFP protein.

25. Construction of the Human Epidermal Growth Factor Receptor with an NLS and Fused to GFP (EGFR-NLS-GFP)

The NLS sequence K K F K R was inserted into the sequence of the human epidermal growth factor receptor by PCR method as follows. Using the human EGFR cDNA in Prk5 vector as template, the first PCR was carried out with HER-XHO and EGF-NLSR primers resulting in a 2.1 kb product. A second PCR was done using HER-KPN and EGF-NLSF primers resulting a 1.5 kb product, and then using PCR#1 and PCR#2 products as templates, the final PCR was done with HER-XHO and HER-KPN primers, which generated a 3.6 kp product (EGFR-NLS) which was subcloned into vector pEGFP (Clontech) at XhoI and KpnI and fused to GFP.

Primer Sequences:

```
EGF-NLSF:                            (SEQ ID NO:113)
5' CACATCGTTCGGAAGAAGTTTAAGCGGAGGCTGCTGC 3'

EGF-NLSR:                            (SEQ ID NO:114)
5' CCTGCAGCAGCCTCCGCTTAAACTTCTTCCGAACGATGTG 3'

Human EGFR wildtype:                 (SEQ ID NO:115)
R R R H I V R K R T L R R L L Q E R E Human EGFR-NLS:                      (SEQ ID NO:116)
R R R H I V R K K F K R R L L Q E R E
```

26. Construction of the Human D1 Dopamine Receptor Containing 2 NLSs and Fused to RFP (D1-NLS(Helix 8 and C-Tail)-RFP)

A second NLS sequence K K K R K was inserted into the carboxyl tail segment of the human D1-NLS-Helix 8 by PCR method as follows. Using the DNA encoding the human D1-NLS-Helix 8 in pDsRed vector as template, the first PCR was carried out with HD1-P1 and HD1-NLSCR primers resulting in a 1.2 kb product, and a second PCR was done using HD1-P2 and HD1-NLSCF primers resulting in a 100 bp product. Then using PCR#1 and PCR#2 products as templates, the final PCR was done with HD1-P1 and HD1-P2 primers which generated a 1.3 kp product (D1-NLS-Helix 8 and C-tail) which was subcloned into pDsRed vector at EcoRI and KpnI and fused to the DsRed protein.

Primer Sequences:

```
HD1-P1:                              (SEQ ID NO:117)
5' GAGGACTCTGAACACCGAATTCGCCGCCATGGACGGGACTG
GGCTGGTG 3'

HD1-P2:                              (SEQ ID NO:118)
5' GTGTGGCAGGATTCATCTGGGTACCGCGGTTGGGTGC
TGACCGTT 3'

HD1-NLSCF:                           (SEQ ID NO:119)
5' CCTCTGAGGACCTGAAAAAGAAGAGAAAGGCTGGCATCGCC 3'

HD1-NLSCR:                           (SEQ ID NO:120)
5' GGCGATGCCAGCCTTTCTCTTCTTTTTCAGGTCCTCAGAGG 3'

D1-wildtype:                         (SEQ ID NO:121)
N P I I Y A F N A D F R K A F S T L L . . .
S S E D L K K E E A A G I A D1-NLS (Helix 8 and C-tail):         (SEQ ID NO:122)
N P I I Y A F N A K K F K R F S T L L . . .
S S E D L K K K R K A G I A
```

27. Construction of the Mu opioid Receptor Fused to GFP (Mu-GFP)

Using the DNA encoding the Mu opioid receptor in pcDNA3 vector as template, PCR was carried out with the following two primers.

```
RATMU1:                              (SEQ ID NO:123)
5' CCTAGTCCGCAGCAGGCCGAATTCGCCACCATGGACAGCAGCACC 3'

RATMU-2:                             (SEQ ID NO:124)
5' GATGGTGTGAGACCGGTACCGCGGGCAATGGAGCAGTTTCTGCC 3'
```

Restriction site EcoRI was incorporated into primer RATMU-1. Restriction site KpnI was incorporated into primer RATMU-2

The PCR product (1.2 kb) which contained no stop codon, was then unidirectionally subcloned into vector pEGFP (Clontech) at EcoR1 and Kpn1 and thus fused to GFP.

28. Construction of the Mu opioid Receptor Containing a NLS and Fused to GFP (Mu-NLS-GFP)

The NLS sequence K K F K R (SEQ ID NO: 157) was inserted into the proximal carboxyl tail segment (helix 8) of the Mu opioid receptor by PCR as follows. Using the DNA encoding the Rat Mu in pcDNA3 as template, the first PCR was carried out with RATMU1 and MU-NLSR primers resulting a 1000 bp product, another second PCR was done using RATMU-2 and MU-NLSF primers resulting a 200 bp product. Using PCR#1 and PCR#2 products as templates the final PCR was done with RATMU1 and RATMU2 primers generated a 1200 bp product (Mu-NLS) which was subcloned into vector pEGFP at EcoR1 and Kpn1 and fused to GFP.

Primer Sequences:

```
RATMU-1:                                    (SEQ ID NO:125)
5' CCTAGTCCGCAGCAGGCCGAATTCGCCACCATGGACAGCAGCACC 3'

RATMU-2:                                    (SEQ ID NO:126)
5' GGATGGTGTGAGACCGGTACCGCGGGCAATGGAGCAGTTTCTGCC 3'

MU-NLSF:                                    (SEQ ID NO:127)
5' GCCTTCCTGGATAAAAAATTCAAGCGATGC 3'

MU-NLSR:                                    (SEQ ID NO:128)
5' GCATCGCTTGAATTTTTTATCCAGGAAGGCG 3'
```

Cell Culture and Transfection

COS-7 monkey kidney cells and HEK293T human embryonic kidney cells (American Type Culture Collection, Manassa, Va.) were maintained as monolayer cultures at 37° C. and 5% $CO_2$ in minimal essential medium supplemented with 10% fetal bovine serum and antibiotics. For cell membrane harvesting, 100 mm plates of cells were transiently transfected at 70-80% confluency using lipofectamine reagent (Life Technologies, Rockville, Md.). For confocal microscopy studies, 60 mm plates of cells were transiently transfected at 10-20% confluency using lipofectamine reagent. Six hours after transfection, the solution was removed and fresh media added and again replaced with fresh media 24 hours after transfection.

Transfection medium was prepared by mixing 120 microlitres medium without antibiotics and/or fetal bovine serum (FBS) and 15 microlitress lipofectamine in a 14 ml tube. 2 micrograms DNA construct encoding the desired fusion protein and 120 microlitres medium were mixed and added to the 14 ml tube, which was mixed gently and incubated at room temperature for 25 minutes. A further 4 ml of medium was added and mixed. If multiple transmembrane proteins are being transfected, the cDNAs are mixed and transfected together. Growth medium was removed from a plate of cells and replaced with the transfection mixture from the 14 ml tube. Cells were incubated with the transfection mixture for 5-6 hours, after which the mixture was removed and replaced with regular growth medium containing FBS and antibiotics. Cells were incubated with a change of regular growth medium on the second day.

Treatment with Test Compounds

Protocol for Determining Retardation of Translocation Off Cell Surface

Test compounds were prepared in a stock solution of 1 millimolar concentration and diluted in growth medium to achieve a final concentration ranging between 10 nanomolar and 10 micromolar when added to cell plates. Fresh compound-containing medium was added to cells at 6 hours, 22 hours, 30 hours and 42 hours after transfection.

Protocol for Determining Promotion of Translocation Off Cell Surface

Test compounds were prepared in a stock solution of 1 millimolar and diluted in growth medium at 37° C. to achieve a final concentration of 10 micromolar when added to cells. Cell cultures were examined microscopically to focus on a single cell and to detect the presence of surface expression of the detectable label protein. Growth medium was replaced with compound-containing medium and the cells were examined microscopically in real time 5, 10, 15, 20, 30 and 35 mins. after addition of compound for changes in distribution of the detectable moiety.

Microscopy

Cells were visualised using the LSM510 Zeiss confocal laser microscope. GFP was visualised following excitation with the argon laser at 488 nm excitation wavelength and the DsRed was visualised following excitation with the helium neon laser at 543 nm wavelength for excitation. The confocal images were captured on disk and evaluated. In each experiment, multiple fields of cells (n=6-8 with 30-90 cells each) were counted and evaluated for localisation of the signal on the cell surface, in the cytoplasm and in the nucleus.

Fluorocytometry

A 96 well plate was coated with poly-L-ornithine (1/10 in PBS) and incubated for one hour. 50,000 cells were added to each well and transfected with cDNA encoding the epitope-tagged receptor, using Lipofectamine (Invitrogen, U.S.A.). The medium (MEM) was changed every 12 hours and contained test drug at varying concentrations or vehicle. 48 hours later, cells were washed and fixed with 4% paraformaldehyde and incubated for 30 min on ice. Cells were then incubated with the primary antibody directed against the epitope and then with the secondary antibody conjugated to FITC (fluorescein isothiocyanate) and kept shielded from light. Excess antibody washed off and the signal detected by reading the plate in a Cytofluor 4000 (PerSpective Biosystems, U.S.A.). The FITC was activated using light at 488 nm for excitation and the signal read at its emission wavelength 530 nm.

Radioligand Binding

Cells were transfected with DNA encoding D1-NLS and treated with varying concentrations of antagonist drug or left untreated. After 48 hours, the cells were washed, harvested, lysed and homogenised by polytron. The membrane fraction was collected by centrifugation and then layered over 35% sucrose solution and centrifuged at 30,000 rpm at 4 degrees C. for 90 min to collect the heavy membrane fraction. The supernatant was again centrifuged at 35,000 rpm at 4 degrees C. for 60 min to collect the light membrane fraction. The membranes were subjected to radioligand binding assay using [$^3$H]-SCH23390 with (+)butaclamol 10 micromolar used to define specific binding. The incubation was at room temperature for 2 hours, followed by rapid filtration and quantitation by scintillation counting.

Isolation of Nuclei from Cultured Cells

Wash cells with PBS 3 times, using 10 ml and scrape gently off the culture dishes. Pool and spin the cells at 500 g for 5 min, at 4 degrees C. Resuspend pelleted cells in lysis buffer (Tris HCl 10 mM, pH 7.4, NaCl 10 mM, MgCl2 3 mM) and inhibitor cocktail (0.5% leupeptin, 1% soybean trypsin, 1% benzamidine) at a density of 50 million cells per ml. Homogenize with sterile glass Teflon pestle B (tight clearance 20-50 mm; Bellco Glass) using 100 up and down strokes.

Spin at 4 degrees C. for 700 g for 10 min, then sequentially centrifuge supernatant at 10 000 g, for 15 min at 4 C (to remove mitochondria) and 120 000 g for 60 min, 4 degrees C. (to remove plasma membrane).

The nuclear pellet is resuspended in lysis buffer (with inhibitors) and 0.1% of NP-40, kept on ice 5 min and then centrifuged at 700 g for 10 min at 4 degrees C. The supernatant is discarded and washing process repeated 3× with 15 ml lysis buffer. Nuclear pellet is resuspended in 2 ml lysis buffer and loaded on top of discontinuous sucrose gradient made by successive layering of 4.5 ml of 2.0 and 1.6 M sucrose containing MgCl2 1 mM and spun at 100 000 g for 60 min at 4 degrees C. The pellet at the bottom of the tube is collected and will contain pure nuclei.

Example 1

Dopamine D1 Receptor Fused to the Red Fluorescent Protein (D1-RFP) or Containing a NLS and Fused to the Red Fluorescent Protein (D1-NLS-RFP)

The sequence of the dopamine D1 receptor, which does not contain an NLS, was modified to replace the amino acids DFRKA at the base of TM7 domain with the NLS sequence KKFKR (which corresponds to the NLS of the human AT1 receptor), as described in the methods (see FIG. 1). DNA constructs were created encoding the D1 dopamine receptor fusion proteins D1-RFP and D1-NLS-RFP. COS cells were transfected with DNA encoding D1-NLS-RFP or D1-RFP (2 micrograms) and incubated for 24 and 48 hours. The cells were examined by confocal microscopy at 100× magnification. Cells were counted manually in 8 to 10 microscopic fields and the percentage labelling in different subcellular compartments was calculated.

At 24 and 48 hours, cells transfected with D1-RFP showed expression at the cell surface in the majority of cells, whereas cells transfected with D1-NLS-RFP showed little receptor expression at the cell surface, with nuclear localisation in 60% of the cells at 24 hours, and in 80% of the cells at 48 hours.

Example 2

Dopamine D1 Receptor Fusion Protein Containing a NLS (D1-NLS-RFP) Treated with Antagonist COS cells were transfected with a construct encoding D1-NLS-RFP and with wildtype D1 (2 micrograms) for 48 hours. At 6, 22, 30 and 42 hours after transfection, the cells were treated with the dopamine D1 receptor antagonist SCH23390 (final concentration 10 micromolar). Also at 6, 22, 30 and 42 hours after transfection, cells were treated with the antagonist (+)butaclamol (final concentration 10 μM). Control cells received no antagonist treatment.

At 48 hours, the majority of control cells had detectable D1-NLS-RFP in the nucleus. In contrast, the majority of antagonist-treated cells had fluorescence only on the cell surface, while 42% had fluorescence both on the surface and in the nucleus.

Example 3

Dopamine D1 Receptor (D1-GFP) Co-Expressed with D1 Receptor Containing a NLS (D1-NLS)

HEK cells were transfected with DNA constructs encoding D1-NLS (3 micrograms) and/or D1-GFP (1.5 micrograms), and incubated for 48 hours. The cells were also transfected with a plasmid encoding DsRed-NUC to verify the localisation of the nucleus (1 microgram).

Cells were also transfected with DNA encoding D1-GFP (2 micrograms), incubated for 48 hours and examined by confocal microscopy.

D1-GFP expressed alone revealed that 90% of the cells demonstrated cell surface labelling and 10% showed both nuclear and cell surface labelling. With any DNA encoding a GPCR transfection, up to 10% of cells may be observed with a nuclear localisation.

Cells expressing D1-GFP and D1-NLS showed 35% of cells with both nuclear and cell surface labelling and 70% with receptor-expression on cell surface only. This experiment indicated that D1-GFP co-trafficked with D1-NLS resulting from oligomerisation of the D1-NLS and D1-GFP.

Example 4

Dopamine D1 Receptor Containing a NLS (D1-NLS-GFP), was Treated with an Antagonist in a Dose Response Study HEK cells were transfected with DNA encoding D1-NLS-GFP (2 micrograms), and D1-WT (6 micrograms) for 48 hours. These cells were treated 6 hrs after transfection with SCH-23390 (10 micromolar), or (+)butaclamol (10 micromolar). The medium containing antagonist was changed at 6, 22, 30 and 42 hours after transfection. Control cells received no antagonist treatment.

Following SCH-23390 treatment for 48 hours, 58% of the cells had cell surface expression of D1-NLS-GFP, less than 10% of the cells had receptor expression in the nucleus and 32% of the cells had receptor expression on both the cell surface and in the nucleus.

Following (+)butaclamol treatment for 48 hours, 62% of the cells had cell surface expression of the D1-NLS-GFP receptor, 10% had receptor expression in the nucleus, and 28% of the cells had receptor expression on the cell surface and in the nucleus.

Control cells at 48 hours showed approximately 65% with D1-NLS-GFP receptor expression in the nucleus, and 35% with receptor expression in the cytoplasm. No receptor D1-NLS-GFP expression was found on the cell surface of control cells.

Incorporation of an NLS into the receptor sequence caused a very efficient removal of the D1-NLS-GFP receptor from the cell surface and localisation in the nucleus.

Similar studies were carried out at various doses of SCH-23390 or (+)butaclamol. Results are shown in Tables 2 and 3. 32% to 35% of control cells showed receptor in cytoplasm.

TABLE 2

| | % cells | | |
| --- | --- | --- | --- |
| SCH-23390 concn | receptor on surface | receptor on surface and in nucleus | receptor in nucleus |
| 10 μM | 58% | 32% | <10% |
| 5 μM | 46% | 42% | 12% |
| 1 μM | 39% | 46% | 15% |
| 0.5 μM | 36% | 44% | 20% |
| 0.2 μM | 32% | 49% | 19% |
| 0.0 μM | 0% | | 62%-70% |

TABLE 3

| (+)butaclamol concn. | receptor on surface | receptor on surface and in nucleus | receptor in nucleus |
|---|---|---|---|
| 10 µM | 62% | 28% | 10% |
| 5 µM | 47% | 43% | 10% |
| 1 µM | 41% | 43% | 16% |
| 0.5 µM | 40% | 41% | 19% |
| 0.2 µM | 39% | 21% | 40% |
| 0.0 µM | 0% | | 62%-70% |

% cells

Incorporation of an NLS into the receptor sequence caused a very efficient removal of the D1 dopamine receptor from the cell surface and localisation in the nucleus. Treatment with D1 selective antagonists prevented this receptor translocation in a dose-responsive manner.

Example 4a

Expression of the Dopamine D1 Receptor with an Inserted NLS (D1-NLS-GFP) and Treatment with Agonists HEK cells were transfected with a DNA construct encoding D1-NLS-GFP (1.5 micrograms), and incubated with the D1 agonist SKF-81297 (10 micromolar) for 48 hours. At 6, 22, 30 and 42 hours after transfection, the cells were treated with fresh medium containing SKF-81297 (final concentration 10 micromolar). The cells were examined by confocal microscopy.

HEK cells were transfected with a DNA construct encoding D1-NLS-GFP (1.5 micrograms of DNA), and incubated with the agonist pergolide (10 micromolar) for 48 hours. At 6, 22, 30 and 42 hours after transfection, the cells were treated with fresh medium containing SKF-81297 (final concentration 10 micromolar). The cells were examined by confocal microscopy.

Control HEK cells were transfected with a DNA construct encoding D1-NLS-GFP (1.5 micrograms of DNA) and left untreated.

In the untreated cells after 48 hrs, there was no receptor detected at the cell surface. With cells treated with SKF-81297, 59% of cells had receptor expression at the cell surface. With cells treated with perglolide there was receptor surface expression in 59% of the cells. Thus long-term treatment with agonists prevented the modified D1 receptor from trafficking to the nucleus.

Example 5

Dopamine D1 Receptor with an Incorporated NLS (D1-NLS-RFP) Co-Expressed with the Wild Type D1 Receptor COS cells were co-transfected with a DNA construct encoding D1-NLS-RFP (1 microgram) and a DNA sequence encoding the native dopamine D1 receptor (D1-WT, 7 microgram) and incubated for 24 or 48 hours.

At 24 hours, DL-NLS-RFP was detected only at the cell surface, whereas at 48 hours, 80% of cells had D1-NLS-RFP in the nucleus. The wild type receptor retarded the movement of the D1-NLS-RFP to the nucleus by homo-oligomerisation.

Example 6

D1 Dopamine Receptor with an Incorporated NLS (D1-NLS-RFP) Co-Expressed with DL-GFP COS cells were transfected with a construct encoding D1-NLS-RFP (4 micrograms) and the dopamine D1-GFP (4 micrograms), and incubated for 48 hours. The cells were examined by confocal microscopy.

D1-GFP was detected at the cell surface and a yellow fluoresence was detected in the nuclei, the latter indicating co-localisation of both D1-NLS-RFP and D1-GFP in the nucleus, confirming oligomerisation of D1-NLS-RFP and DL-GFP, leading to importation of D1-GFP into the nucleus.

Example 6a

Expression of the D1 Dopamine Receptor with an NLS Inserted in the Third Intracellular Cytoplasmic Loop (D1-IC3-NLS-GFP)

HEK cells were transfected with a DNA construct encoding D1-IC3-NLS-GFP (2 micrograms), and incubated for 48 hours. Nuclei were visualised with DsRED-NUC (2 micrograms). The cells were examined by confocal microscopy.

In cells transfected with D1-IC3-NLS-GFP, the receptor was detected in the nucleus of 85% of cells. Thus insertion of a NLS into the third intracellular loop enabled receptor trafficking to the nucleus.

Example 6b

Expression of the D1 Dopamine Receptor with an NLS Inserted in the First Intracellular Cytoplasmic Loop (D1-IC1-NLS-GFP)

HEK cells were transfected with a DNA construct encoding D1-IC1-NLS-GFP (2 micrograms), and incubated for 48 hours. Nuclei were visualised with DsRED-NUC (2 micrograms). The cells were examined by confocal microscopy.

In cells transfected with D1-IC1-NLS-GFP, the receptor was detected in the nucleus of 85% of cells. Thus insertion of a NLS into the first intracellular loop enabled receptor trafficking to the nucleus.

Example 6c

Effect of the Antagonist Butaclamol or SCH-23390 on the Trafficking of the D1 Dopamine Receptor with an NLS Inserted in the First Cytoplasmic Loop (D1-IC1-NLS-GFP)

HEK cells were transfected with a DNA construct encoding D1-IC1-NLS-GFP (2 micrograms), and treated with either butaclamol (final concentration 1 micromolar or SCH-23390 (1 micromolar), for 48 hours. Nuclei were visualised with DsRED-NUC (2 micrograms). The cells were examined by confocal microscopy.

With the butaclamol treated cells, 82% had receptor on the cell surface or in the cytoplasm. 18% of the cells had receptor in the nucleus. Thus treatment with butaclamol reduced D1-IC1-NLS-GFP trafficking to the nucleus.

With the SCH-23390 treated cells, 77% of the cells had receptor on the cells surface or in the cytoplasm. 23% of the cells had receptor in the nucleus. Thus treatment with SCH-23390 reduced receptor trafficking to the nucleus.

With the untreated cells 76% had receptor expression in the nucleus and cytoplasm.

Example 6d

Effect of the Antagonist SCH-23390 on the Trafficking of the D1 Dopamine Receptor with an NLS Inserted in the Third Cytoplasmic Loop (D1-IC3-NLS-GFP)

HEK cells were transfected with a DNA construct encoding D1-IC3-NLS-GFP (2 micrograms), and treated with four different concentrations of SCH-23390 (10 micromolar, 1 micromolar, 500 nanomolar and 100 nanomolar), for 48 hours. Nuclei were visualised with DsRED-NUC (2 micrograms). The cells were examined by confocal microscopy.

86% of the cells transfected with D1-IC3-NLS-GFP had the receptor in the nucleus, and 0% had receptor on the surface. With the SCH-23390 treated cells, 84% had receptor in the nucleus and 15% of the cells had receptor on the surface. The insertion of an NLS at this position in the GPCR will translocate the receptor to the nucleus efficiently but does not respond to the drug.

Example 6e

Expression of the D1 Dopamine Receptor with an NLS Inserted in the Second Intracellular Cytoplasmic Loop (D1-IC2-NLS-GFP)

HEK cells were transfected with a DNA construct encoding D1-IC2-NLS-GFP (2 micrograms), and incubated for 48 hours. Nuclei were visualised with DsRED-NUC (2 micrograms). The cells were examined by confocal microscopy.

In cells transfected with D1-IC2-NLS-GFP, the receptor was detected in the nucleus of 51% of cells.

Example 6f

Ability of the Dopamine D1 Receptor to Homodimerise, with Staggered Transfection HEK cells were transfected with a DNA construct encoding D1-RFP (2 micrograms) and after 24 hours incubation, the cells were transfected with a second DNA construct encoding D1-NLS-GFP (2 micrograms). Control cells were transfected with the D1-RFP (2 micrograms) construct alone. The cells were incubated for 48 hours following the second transfection and examined by confocal microscopy.

90% of the cells transfected with D1-RFP alone expressed receptor on the cell surface, and 6% of the cells expressed receptor in the nucleus. In contrast, 97% of the cells expressing both forms of the receptor expressed both receptors (red plus green equals yellow fluorescence) in the nucleus. Thus, the D1 receptor without the NLS interacted with the D1 receptor with the NLS in order to traffic to the nucleus.

Example 7

Dopamine D5 Receptor (D5-GFP)

A construct encoding the dopamine D5 receptor-GFP (D5-GFP) was prepared and used to transfect COS cells (4 micrograms).

Cells transfected with dopamine D5-GFP, at 48 hours, showed mainly a cytoplasmic localisation of receptor, with cell surface localisation in only a few cells and no instances of nuclear localisation.

Example 8

Dopamine D1 with an Incorporated NLS (D1-NLS) Co-Expressed with the D5 Dopamine Receptor (D5-GFP)

HEK cells were transfected with two DNA constructs, one encoding D1-NLS (7 micrograms) and the other encoding D5-GFP (1.5 micrograms), and incubated for 48 hours.

Approximately 70% of the cells transfected with D1-NLS and D5-GFP had cell surface expression of D5-GFP, 20% of the cells had both surface and cytoplasm expression of D5-GFP, and 10% had nuclear expression of D5-GFP. There was no nuclear translocation of the D5 dopamine receptor coexpressed with D1-NLS, indicating that the D1 and D5 receptors did not oligomerise.

Example 9

D1 Dopamine Receptor Containing Two NLS Motifs (D1-2NLS-RFP) and Treated with Antagonist By modifying the construct encoding D1-NLS-RFP, a DNA construct (D1-2NLS-RFP) was created to introduce a second NLS into the carboxyl tail of the dopamine D1 receptor by replacing the KKEEA sequence of the wild type D1 dopamine receptor with the NLS, KKKRK.

HEK cells were transfected with DNA encoding this construct (D1-2NLS-RFP), and treated at intervals with the antagonist SCH-23390 (10 µM) as previously described. At 6, 22, 30 and 42 hours after transfection, the culture medium containing antagonist was replaced. Control cells received no antagonist.

In both COS and HEK cells transfected with D1-2NLS-RFP, the receptor was located in the nucleus in 100% of cells after 24 hours, indicating enhanced nuclear translocation when a second NLS was present.

At 48 hours, 90% of cells not treated with antagonist showed fluorescence in the nucleus and 0% of cells had fluorescence on the cell surface. Antagonist-treated cells showed 51% of cells with cell surface label and 49% with nuclear label.

Incorporation of a second NLS resulted in a more efficient transport of the receptor to the nucleus, and this event was still retarded by antagonist treatment.

Example 10

D2 Dopamine Receptor (D2-GFP)

HEK cells were transfected with DNA constructs encoding D2-GFP (2 micrograms) and DsRed-NUC (1 microgram), and incubated for 48 hours. Cells were examined by confocal microscopy.

Approximately 90% of the cells expressing D2-GFP had cell surface expression, and 10% had nuclear or cytoplasm expression. The D2 dopamine receptor, having no endogenous NLS, is predominantly expressed on the cell surface.

Example 11a

Dopamine D1 Receptor with an Incorporated NLS (D1-NLS) and Dopamine D2 (D2-GFP)

HEK cells were transfected with DNA constructs encoding D1-NLS (7 micrograms), and D2-GFP (1.5 micrograms)

and incubated for 48 hours. The cells were also transfected with Ds-Red-NUC to verify the localisation of the nucleus (1 microgram). The cells were examined by confocal microscopy.

In cells transfected with D1-NLS and D2-GFP, 33% of the cells had D2-GFP expression in the nucleus, indicating transport of both D1-NLS and D2-GFP to the nucleus, due to oligomerisation between the D1 and D2 receptors. 67% of the cells had D2-GFP receptors on the cell surface only or on surface and cytoplasm.

Example 11b

Ability of D2 Dopamine Receptor D2 Short (D2S) to Dimerise with Dopamine Receptor D2 Long (D2L)

HEK cells were transfected with DNA constructs encoding D2S-GFP (2 micrograms) and D2L-NLS (2 micrograms) and were incubated for 48 hours. Nuclei were visualised with DsRED-NUC (2 micrograms). The cells were examined by confocal microscopy.

D2S-GFP receptor was visualised in the nuclei of 29% of cells. This indicated that D2S dimerised with D2L and was transported to the nucleus.

Example 11c

Ability of Dopamine Receptor D2S to Dimerise with Dopamine Receptor D2L

HEK cells were transfected with DNA constructs encoding D2S-RFP (2 micrograms) and D2L-NLS-GFP (2 micrograms) and incubated for 48 hours. The cells were examined by confocal microscopy.

40% of the cells had a yellow colour (red plus green overlay) in the nucleus, indicating that D2L-NLS dimerised with D2S-RFP and transported it to the nucleus.

Example 12

D2 Dopamine Receptor with an Incorporated NLS (D2-NLS-GFP) Treated with Antagonists HEK cells were transfected with DNA encoding D2-NLS-GFP and the cells were treated with the D2 dopamine receptor antagonists, (+)butaclamol (10 micromolar) or raclopride (10 micromolar). At 6, 22, 30 and 42 hours after transfection, the cells were treated with the antagonists. Cells were incubated 48 hrs after drug treatment and examined by confocal microscopy.

In the absence of antagonist, cells expressing D2-NLS-GFP showed nuclear label in 70% of cells, and cytoplasmic labelling in 20% and cytoplasmic and surface labelling in 10% of cells. With (+)butaclamol treatment, nuclear labelling appeared in only 5% of cells, 5% of cells had cytoplasmic label and 90% of the cells had cell surface labelling. With raclopride treatment, 5% of cells showed nuclear labelling, 15% of cells had cytoplasmic labelling and 80% of cells had cell surface labelling. Both antagonists of the D2 receptor prevented the translocation of the receptor off the cell surface and to the nucleus.

Example 13

Beta2-adrenergic Receptor-GFP (beta2-AR-GFP)

A DNA construct was created encoding a fusion protein comprising the human beta2-adrenergic receptor and GFP (beta2-AR-GFP). Cells were transfected with the DNA construct encoding beta2-AR-GFP (2 micrograms), and incubated for 24 hours and examined by confocal microscopy.

In cells expressing beta2-AR-GFP, 42% of cells had receptor expression in cytoplasm only, and 58% of the cells had receptor expression in the cytoplasm and on the cell surface. No nuclear localisation of the receptor was observed.

Example 14

Beta2-adrenergic Receptor with an Incorporated NLS (beta2-AR-NLS3-GFP)

A DNA construct was created encoding a fusion protein comprising the human beta2-AR-NLS3-GFP. HEK cells were transfected with DNA encoding beta2-AR-NLS3-GFP-3 (2 microgram), and Ds-Red-NUC (1 microgram) and the cells were incubated for 48 hours.

45% of the cells transfected with beta2-AR-NLS3-GFP had nuclear localisation of receptor and 55% of the cells had surface and cytoplasmic expression. Incorporation of a NLS into the beta2-AR induced receptor translocation to the nucleus.

Example 15

Beta2-adrenergic Receptor with an Incorporated NLS (beta2-AR-NLS3-GFP), Treated with Antagonist HEK cells were transfected with DNA encoding beta2-AR-NLS3-GFP (1 microgram), and Ds-Red-NUC (1 microgram) and incubated for 48 hours. Cells were treated at intervals with atenolol (10 micromolar), an adrenergic receptor antagonist. At 6, 22, 30 and 42 hours after transfection, the culture medium containing the antagonist was replaced.

Control cells received no antagonist. In control cells, 60% had receptor expression in the nucleus, 21% had receptor expression on the cell surface, 19% had receptor expression in the cytoplasm.

In antagonist atenolol-treated cells, 70% had receptor expression on the cell surface, 14% had receptor expression in the nucleus, and 16% had receptor expression in the cytoplasm. Treatment with the antagonist atenolol prevented beta2-AR-NLS3-GFP trafficking to the nucleus and retained the receptor on the cell surface.

Example 16

Beta2-adrenergic Receptor (beta2-AR-GFP) Coexpressed with Dopamine D1 Receptor with an Incorporated NLS (D1-NLS)

HEK cells were transfected with DNA constructs encoding the beta2-AR-GFP (1.5 microgram) and D1-NLS (3 microgram) for 48 hours.

Approximately 40% of cells showed beta2-AR-GFP receptor expression in the nucleus, demonstrating that the beta2-AR not containing an NLS had trafficked to the nucleus. This indicated that oligomerisation had occurred between the beta2-AR receptor and D1 dopamine receptor, containing the NLS. 45% of the cells showed beta2-AR-GFP in the cytoplasm and 15% in cytoplasm and on cell surface.

Example 17

Beta2-Adrenergic Receptor (beta2-AR-GFP) and Dopamine D1 Receptor with an Incorporated NLS (D1-NLS) Treated with Antagonist HEK cells were transfected with DNA constructs encoding beta2-AR-GFP (1.5 micrograms) and D1-NLS (3 micrograms) and incubated for 48 hours. These cells were treated with the adrenergic antagonist, propranolol (5 micromolar). At 6, 22, 30 and 42 hours after transfection the culture medium containing the antagonist was replaced. Control cells received no antagonist. The cells were examined by confocal microscopy.

25% of control cells showed beta2-AR-GFP nuclear expression and 75% of cells showed label in cytoplasm and on cell surface.

In propranolol-treated cells, beta2-AR-GFP nuclear expression was 10%, and 90% of the cells showed cytoplasmic and surface label. The formation of a heterooligomer with between beta2-AR-GFP and D1-NLS resulted in the trafficking of the beta2-AR-GFP to the nucleus. This trafficking was attenuated by the presence of the antagonist to the adrenergic receptor.

Example 18

Beta2-adrenergic Receptor with an Incorporated NLS (beta2-AR-NLS3-GFP)

HEK cells were transfected with a DNA construct containing an NLS encoding beta2-AR-NLS3-GFP (8 micrograms) for 48 hours. The cells were also transfected Ds-Red-NUC to verify the localisation of the nucleus (1 microgram).

80% of cells showed beta2-AR-NLS3-GFP receptor in the nucleus. The efficiency of the NLS was improved, resulting in a greater localisation of receptor in the nucleus.

Example 19

Serotonin 1B Receptor with an Incorporated NLS (5HT1B-NLS-GFP) and Treatment with Antagonist HEK cells were transfected with a DNA construct encoding the serotonin 5HT1B-NLS-GFP (2 micrograms). The cells were transfected with Ds-red-NUC to verify the localisation of the nucleus (1 microgram). Cells were treated with methysergide (10 micromolar), a serotonin receptor antagonist. At 6, 22, 30 and 42 hours after transfection, the culture medium containing antagonist was replaced. Control cells received no antagonist. The cells were examined by confocal microscopy.

Control cells, not treated with antagonist, showed 55% with receptor localised in the nucleus, and 20% with receptor localised on the cell surface. At 48 hours, methysergide-treated cells showed 25% of the cells had receptor in the nucleus and 62% of the cells had cell surface localisation.

The serotonin 5HT1B receptor was efficiently translocated from the cell surface to the nucleus by insertion of the NLS. Treatment with the serotonin antagonist methysergide prevented the translocation of the receptor.

Example 20

Cysteinyl Leukotriene Receptor-2 with an Incorporated NLS (CysLT2-NLS-GFP)

HEK cells were transfected for 48 hours with a DNA construct encoding CysLT2-NLS-GFP (8 micrograms). The cells were also transfected with Ds-RED-NUC to verify the localisation of the nucleus (1 microgram). The cells were examined by confocal microscopy.

83% of cells expressing Cys-LT2-NLS-GFP showed receptor expression in the nucleus and 0% of cells had receptor expression on the cell surface, indicating Cys-LT2-NLS-GFP receptor localisation in the nucleus.

Example 21

Cysteinyl Leukotriene Receptor-2 with an Incorporated NLS (Cys-LT2-NLS-GFP) Treated with Antagonist The DNA encoding Cys-LT2-NLS-GFP (3 micrograms) was used to transfect HEK cells. These cells were treated with the cysteinyl leukotriene receptor antagonist, montelukast (10 micromolar). At 6, 22, 30 and 42 hours after transfection the culture medium containing antagonist was replaced. Control cells received no antagonist. The cells were examined by confocal microscopy.

In the absence of antagonist, 70% of cells expressing Cys-LT2-NLS-GFP had localisation of receptor in the nucleus and 30% of cells showed a cytoplasmic localisation with 0% of cells showing receptor on the cell surface. For the antagonist-treated cells, only 10% showed nuclear localisation of the receptor, while 90% showed cell surface expression of receptor. Thus the cysteinyl leukotriene receptor antagonist montelukast prevented the transport of the Cys-LT2-NLS-GFP receptor off the cell surface and into the nucleus.

Example 22

Mu opioid Receptor with an Incorporated NLS (mu opioid-NLS-GFP)

HEK cells were transfected for 48 hours with a DNA construct encoding the mu opioid-NLS-GFP (2 micrograms). The cells were also transfected with Ds-Red-NUC (1 microgram) to verify the localisation of the nucleus. The cells were examined by confocal microscopy.

65% of the mu opioid-NLS-GFP transfected cells showed receptor expression in the nucleus. 15% of the cells showed cell surface localisation of receptor and 20% receptor of cells had cytoplasmic labelling. Thus the insertion of the NLS permitted the mu opioid receptor to traffic to the nucleus.

Example 23

Mu opioid Receptor with an Incorporated NLS (mu-NLS-GFP) Treated with Antagonists HEK cells were transfected with a DNA construct encoding the mu opioid-NLS-GFP (2 micrograms). The transfected cells were treated with the mu opioid antagonists, naloxone (10 micromolar) or naltrexone (10 micromolar). At 6, 22, 30 and 42 hours after transfection the culture medium containing the antagonist was replaced. Control cells received no antagonist. The cells were examined by confocal microscopy.

When untreated, 62% of cells had Mu-NLS-GFP in the nucleus and 20% of cells had receptor detectable on the cell surface. With naloxone treatment, 21% of cells had receptor expression in the nucleus and 66% of cells had receptor on the cell surface. With naltrexone treatment, 22% of cells had receptor expression in the nucleus and 58% of cells had receptor on the cell surface. Thus the mu opioid antagonists naloxone and naltrexone reduced receptor translocation off the cell surface and to the nucleus.

Example 24

Muscarinic M1 Receptor with an Incorporated NLS (M1-NLS-GFP) Treated with Antagonist HEK cells were transfected with DNA encoding M1-NLS-GFP (1 microgram), and Ds-Red-NUC (1 microgram) for 48 hours. These cells were treated with iprotropium bromide (10 micromolar). The medium containing antagonist was replaced at 6, 22, 30 and 42 hours after transfection. Control cells received no antagonist treatment. The cells were examined by confocal microscopy.

Following iprotropium bromide treatment, 72% of the cells had receptor expression on the cell surface, 17% had receptor expression in the cytoplasm only, 11% of the cells had receptor expression in the nucleus.

For control cells, 64% had receptor expression in the nucleus, 23% had receptor expression on the cell surface and 13% of the cells had receptor expression in cytoplasm.

Treatment with a muscarinic antagonist prevented the M1-NLS-GFP from translocating off the cell surface and trafficking to the nucleus.

Example 25

Histamine H1 Receptor with an Incorporated NLS (H1-NLS-GFP)

HEK cells were transfected with a DNA construct encoding the histamine H1-NLS-GFP receptor (2 micrograms), and a construct encoding Ds-Red-NUC (1 microgram) for and incubated for 48 hours.

Approximately 65% of the cells had receptor expression in the nucleus, and 35% of the cells had receptor expression on both surface and cytoplasm. Insertion of the NLS into the H1 histamine receptor resulted in translocation of the receptor off the surface and to the nucleus.

Example 26

Effect of the Antagonist Promethazine on the Trafficking of the H1 Histamine Receptor with an NLS Inserted (H1-NLS-GFP)

HEK cells were transfected with H1-NLS-GFP (2 micrograms) and DsRED-Nuc (2 micrograms) and incubated for 48 hours. The cells were treated with promethazine (10 micromolar) for 48 hours. Nucleii were visualised with DsRED-Nuc. The cells were examined by confocal microscopy.

With the promethazine treated cells 88% of the cells had receptor on the cell surface, 10% of the cells had receptor in the nucleus. With the untreated cells 85% had receptor expression in the nucleus and cytoplasm. Thus treatment with promethazine reduced H1-NLS-GFP trafficking to the nucleus.

Example 26

Angiotensin AT1 Receptor (AT1R)

A DNA construct (AT1R-RFP) was created encoding a fusion protein comprising the NLS-containing human angiotensin AT1 receptor and DsRed2 (RFP).

COS cells were transfected with the DNA construct AT1R-RFP (4 micrograms) and incubated for 48 hours at 37° C.

Cells were examined by confocal microscopy and the receptor was found to be located exclusively within the nuclei of the cells, indicating a basal agonist-independent translocation of the AT1R into the nucleus.

Example 27

Dopamine Receptor (D1-NLS-GFP) Treated with Agonist for a Short Term

HEK cells were transfected with the DNA constructs encoding D1-NLS-GFP (2 micrograms), and D1-WT (4 micrograms), and the cells incubated for 24 hours. The cells were treated with the dopamine D1 agonist, SKF 81297 (10 micromolar) for 35 mins. A single group of cells were visualised by confocal microscopy in real time.

An increased expression of the receptor in the nucleus was demonstrated, with a maximum increase occurring at 20 minutes, indicating short term agonist effect.

Example 28

Dopamine Transporter with a NLS, Fused to GFP and RFP (DAT-NLS-GFP and DAT-NLS-RFP)

HEK cells were transfected with a DNA construct encoding DAT-GFP (2 micrograms) for 48 hours. Nuclei were visualised with DsRED-nuc (2 micrograms) using confocal microscopy.

At 48 hours, DAT-GFP was detected on the cell surface or in the cytoplasm in 86% of the cells. In 14% of the cells, the transporter was in the nucleus.

HEK cells were transfected with a construct encoding DAT-NLS-RFP (2 micrograms) and visualised by confocal microscopy at 48 hours. DAT-NLS-RFP was detected in the nuclei in 85% of the cells. In 18% of the cells, the transporter was either at the surface or in the cytoplasm.

HEK cells were then transfected with DNA encoding DAT-NLS-GFP. (2 micrograms) and visualised by confocal microscopy at 48 hours. Nuclei were visualised with DsRED-nuc (2 micrograms). DAT-NLS-GFP was detected in the nucleus of 77% of cells.

Example 29

Co-Trafficking of DAT-GFP with DAT-NLS-RFP

HEK cells were transfected with DNA constructs encoding DAT-NLS-RFP (2 micrograms) and DAT-GFP (2 micrograms), and incubated for 48 hours. The cells were examined by confocal microscopy.

A yellow fluorescence was detected in the nuclei in 56% of the cells, indicating co-localisation of DAT-NLS-RFP and DAT-GFP in the nucleus, confirming oligomerisation of DAT-NLS-RFP and DAT-GFP.

Example 30

Effect of Cocaine on DAT-NLS-RFP Trafficking to the Nucleus

HEK cells were transfected with a DNA construct encoding DAT-NLS-RFP (2 micrograms) and incubated for 48 hours. At 6, 22, 30 and 42 hours after transfection, the cells were treated with cocaine or amphetamine (final concentration 10 micromolar), or left untreated. The cells were examined by confocal microscopy.

In the non-treated HEK cells, 77% of the cells had DAT-NLS-RFP expression in the nucleus.

Following cocaine treatment, 75% of the cells had cell surface or cytoplasmic expression of DAT-NLS-RFP, whereas 25% of the cells had transporter expression in the nucleus and cytoplasm. Treatment with cocaine reduced the trafficking of the DAT-NLS-RFP to the nucleus.

Following amphetamine treatment, 34% of the cells had cell surface/cytoplasm expression, and 66% of the cells had transporter expression in the nucleus/cytoplasm. Treatment with an amphetamine (which does not target DAT but targets the vesicular monoamine transporter, VMAT) had no inhibitory effect on the trafficking of the DAT-NLS-RFP to the nucleus.

Example 31

Expression of the Dopamine Transporter with a NLS (DAT-NLS-GFP) and Treatment with Antagonists HEK cells were transfected with a DNA construct encoding DAT-NLS-GFP (2 micrograms) and incubated for 48 hours. At 6, 22, 30 and 42 hours after transfection, the cells were treated with GBR-12909 (final concentration 1 micromolar). The cells were examined by confocal microscopy.

HEK cells were transfected with a construct encoding DAT-NLS-GFP (2 micrograms) and incubated for 48 hours. At 6, 22, 30 and 42 hours after transfection cells were treated with mazindol (final concentration 1 micromolar). The cells were examined by confocal microscopy.

Control HEK cells were transfected with DAT-NLS-GFP incubated for 48 hours and not treated with drug.

In the untreated HEK cells transfected with DAT-NLS-GFP, 77% of the cells had transporter expression in the nucleus and cytoplasm, 23% in the cytoplasm only, and 0% on the cell surface.

Following GBR-12909 treatment, 62% of the cells had transporter expression on the cell surface and in cytoplasm, and 38% of the cells had transporter expression in the nucleus and cytoplasm. Treatment with GBR-12909 reduced DAT-NLS-GFP translocation off the cell surface and trafficking to the nucleus.

Following mazindol treatment 61% of the cells had cell surface and cytoplasm expression of transporter, and 39% of the cells had transporter expression in the nucleus and cytoplasm. Treatment with mazindol reduced the DAT-NLS-GFP translocation of the cell surface and trafficking to the nucleus.

Example 32

Ability of Dopamine Transporter to Homooligomerise, Using Staggered Expression of DAT-GFP and DAT-NLS-RFP HEK cells were transfected with the DNA construct encoding DAT-GFP (2 micrograms) and 24 hrs later with the DNA construct encoding DAT-NLS-RFP (0.5, 1, and 2 micrograms) and incubated for 48 hours. Cells were also transfected with DAT-GFP alone as control. The cells were incubated 48 hours after the second transfection. Total incubation period was 72 hours.

85% of the cells transfected with DAT-GFP alone contained transporter in the cytoplasm, and 7% in the nucleus. In the staggered experiment (ratio 1:0.5), 97% of the cells had yellow (=red+green) fluorescence in the nucleus. In the staggered experiment (ratio 1:1), 94% of the cells had yellow fluorescence in the nucleus. In the staggered experiment (ratio 1:2), 94% of the cells had yellow fluorescence in the nucleus. Therefore the DAT-GFP interacted with and dimerised with DAT-NLS-RFP in order to traffic to the nucleus.

Example 33

Expression of the Metabotropic Glutamate-4-Receptor (mGluR4-GFP)

HEK cells were transfected with a DNA construct encoding mGluR4-GFP (2 micrograms) and incubated for 48 hours. Nuclei were visualised with DsRED-NUC (2 micrograms). The cells were examined by confocal microscopy.

89% of the receptors were expressed at the cell surface. Thus the mGluR4 receptor was largely located at the cell surface.

Example 34

Expression of the Metabotropic Glutamate-4 Receptor with an Inserted NLS (mGluR4-NLS-GFP)

HEK cells were transfected with a DNA construct encoding mGluR4-NLS-GFP (2 micrograms), and incubated for 48 hours. The cells were also transfected with Ds-RED-NUC (2 micrograms) to verify the localisation of the nucleus. The cells were examined by confocal microscopy.

60% of cells expressing mGluR4-NLS-GFP showed expression of receptor in the nucleus.

Thus the insertion of an NLS into the mGluR4 receptor increased the nuclear localisation of the receptor.

Example 35

Expression of the Muscarinic M1 Receptor with or without NLS Incorporation (M1-GFP and M1-NLS-GFP)

HEK cells were transfected with a DNA construct encoding the M1-GFP (2 micrograms) or with a construct encoding the M1-NLS-GFP (2 micrograms) and incubated for 48 hours. Nuclei were visualised with DsRED-NUC (2 micrograms). The cells were examined by confocal microscopy.

After transfection with M1-GFP, 67% of the cells had receptor expressed on the cell surface or in the cytoplasm.

Transfection with M1-NLS-GFP showed 92% of the cells with nuclear expression of the receptor, indicating that the NLS directed the receptor to the nucleus.

Example 36

Expression of the H1 Histamine Receptor (H1-GFP)

HEK cells were transfected with a DNA construct encoding H1-GFP (1.5 micrograms) and incubated for 48 hours. Nuclei were visualised with DsRED-NUC (2 micrograms). The cells were examined by confocal microscopy.

97% of the cells expressed receptor at the cell surface. Thus, the unmodified receptor did not traffic to the nucleus.

Example 37

Expression of the Cysteinyl Leukotriene Receptor with NLS Inserted (CysLT1-NLS-GFP)

HEK cells were transfected with a DNA construct encoding CysLT1-NLS-GFP (2 micrograms) and incubated for 48 hours. Nuclei were visualised with DsRED-NUC (2 micrograms). The cells were examined by confocal microscopy.

With the control untreated cells, 0% of the cells had receptor expression on the cell surface, and 100% of the cells had nuclear expression, indicating robust removal of the receptor off the cell surface.

Example 38

Expression of the Serotonin Transporter Fused to GFP (SERT-GFP)

HEK cells were transfected with a DNA construct encoding SERT-GFP (2 micrograms) and incubated for 48 hours. 91% of the cells expressed transporter on the cell surface and cytoplasm.

Example 39

Expression of the Serotonin Transporter with an Inserted NLS and Treatment with Fluoxetine (SERT-NLS-GFP)

HEK cells were transfected with DNA encoding SERT-NLS-GFP (2 micrograms of DNA) and treated with fluoxetine (final concentrations micromolar) for 48 hours. At 6, 22, 30 and 42 hours after transfection, the cells were treated with fluoxetine (final concentration 1 micromolar). The cells were examined by confocal microscopy.

In the untreated cells expressing SERT-NLS-GFP, 0% of the cells had transporter expression on the cell surface, 26% had transporter expression in the cytoplasm, and 60% of the cells had transporter expression in the nucleus and cytoplasm.

Following fluoxetine treatment, 68% of the cells had SERT-NLS-GFP transporter expression on the cell surface and cytoplasm, and 27% of the cells had transporter expression in the nucleus and cytoplasm. Thus treatment with fluoxetine inhibited the SERT-NLS-GFP from translocating off the cell surface and trafficking to the nucleus.

Example 40

Evaluation of the Ability of Two Different Cell Surface Membrane Proteins to Interact with Each Other (D2-GFP and DAT-NLS-RFP)

HEK cells were cotransfected with DNA constructs encoding the D2-GFP (2 micrograms) and DAT-NLS-RFP (2 micrograms) and incubated for 48 hours. Cells were also transfected separately with D2-GFP and DAT-NLS-RFP alone as controls. The cells were examined by confocal microscopy.

85% of the cells transfected with DAT-NLS-RFP contained transporter in the nucleus. 97% of the cells transfected with D2-GFP contained the receptor on the cell surface, and 4% of the cells contained receptor in the nucleus. 86% of the cotransfected cells contained yellow (red plus green) fluorescence in the nucleus, indicating the presence of both D2 and DAT proteins in the nucleus and confirming dimerisation of the co-expressed proteins.

Example 41

Evaluation of the Ability of a Membrane Protein and a Non-Membrane Protein, to Associate in a Complex and Interact with Each Other (D1-NLS and beta-arrestin1-GFP)

HEK cells were co-transfected with DNA constructs encoding D1-NLS (2 micrograms) and beta-arrestin1-GFP (2 micrograms) and incubated for 48 hours. Cells were also transfected with beta-arrestin1-GFP alone. The cells were checked by confocal microscopy.

100% of cells transfected with beta-arrestin1-GFP alone expressed fluorescent protein in the cytoplasm. Of these cells 15% also had fluorescence in the nucleus. 89% of cells co-transfected with both proteins expressed fluorescent protein in the nucleus and of these 16% had expression in the cytoplasm. Thus, the interaction between the GPCR and the non-membrane protein enabled the trafficking of the non-NLS containing beta-arrestin protein to the nucleus.

Example 42

Figure 2:
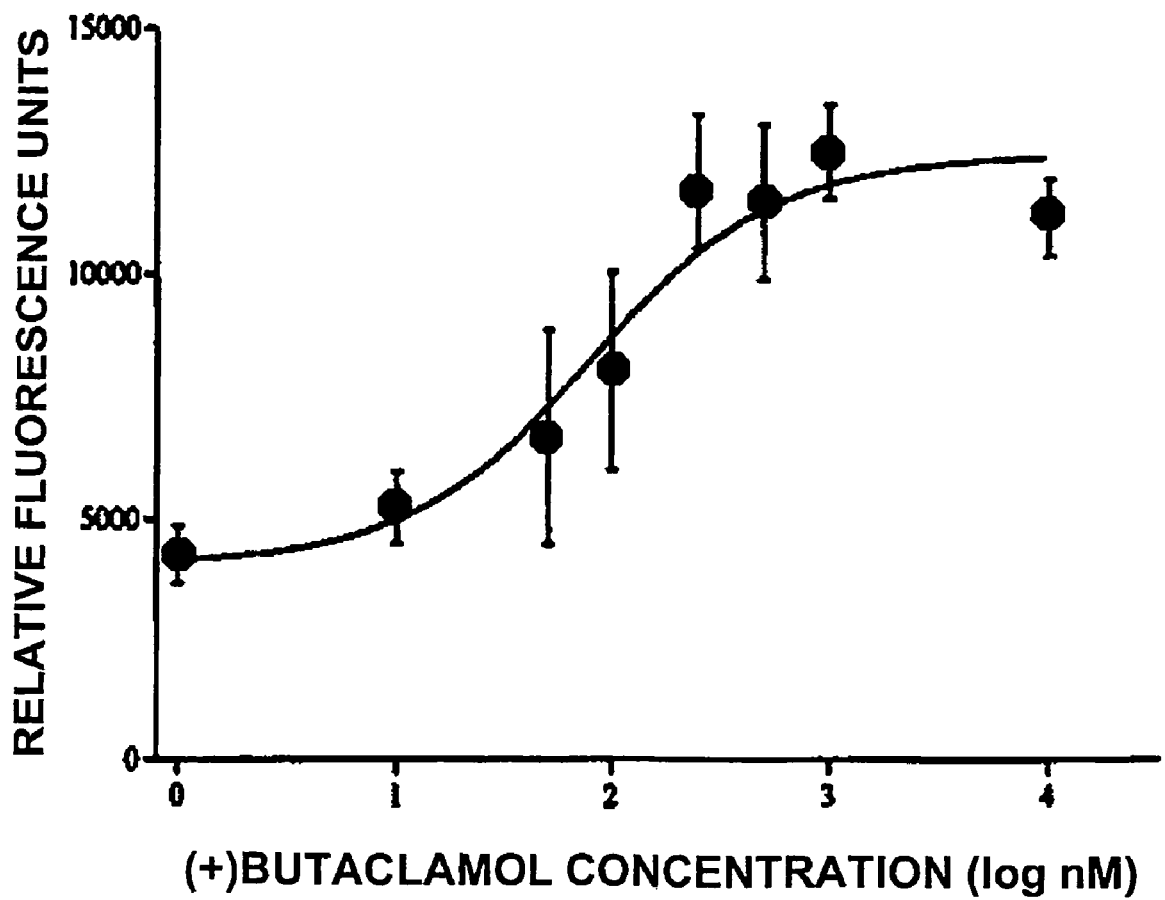
FIG. 2 shows fluorescence (Relative fluorescence units) at surface of HEK cells transfected with dopamine D1 receptor-NLS and treated with various concentrations of butaclamol.

Expression of the Dopamine D1 Receptor with an Inserted NLS (HA-D1-NLS) Treatment with Antagonist and Detection with Fluorometry Wells in a multi-well plate were coated with poly-L-ornithine and then plated with 50,000 cells per well. The cells were transfected with DNA encoding an HA epitope tagged D1-NLS receptor and treated with (+)butaclamol (10 nanomolar to 10 micromolar) over 48 hours. Following this, the cells were fixed with paraformaldehyde, and cell surface receptors were detected with a rat anti-HA antibody and then a goat anti-rat antibody conjugated to FITC. The fluorescent signal was detected by fluorometry (Cytofluor). The results are the average of five wells per experimental condition and are shown in FIG. 2. There was a dose-dependent effect of butaclamol to retain receptor on the cell surface, indicating that this antagonist reduced receptor trafficking from the cell surface. Thus fluorometry can be utilised to detect receptor retained at the cell surface.

Example 43

Figure 3:
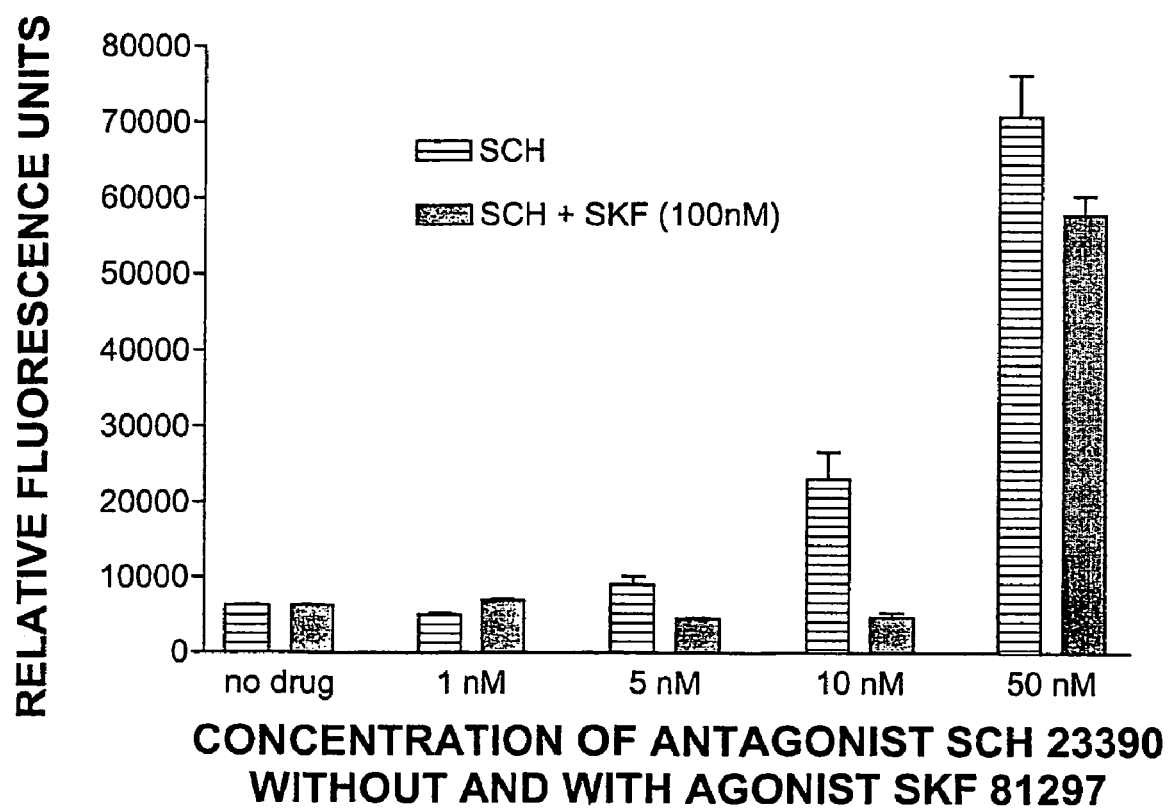
FIG. 3 shows cell surface fluorescence of HEK cells transfected with HA-dopamine D1 receptor-NLS and treated with various concentrations of SCH23390 alone or with SKF81297 (100 nM).

Expression of the Dopamine D1 Receptor with an Inserted NLS (HA-D1-NLS), and Blockade of Antagonist Dose-Response Effect by Agonist and Detection with Fluorometry Wells in a multi-well plate were coated with poly-L-ornithine and then plated with 50,000 cells per well. The cells were transfected with DNA encoding an HA epitope tagged D1-NLS receptor and treated with the antagonist SCH 23390 (1 nanomolar to 1 micromolar) with or without the agonist SKF 81297 (1 micromolar) over 48 hours. Following this, the cells were fixed with paraformaldehyde, and cell surface receptors were detected with a rat anti-HA antibody and then a goat anti-rat antibody conjugated to FITC. The fluorescent signal was detected by fluorometry (Cytofluor). The results are the average of five wells per experimental condition. There was a dose-dependent effect of SCH 23390 to retain receptor on the cell surface, indicating that this antagonist reduced receptor trafficking from the cell surface. The concomitant addition of agonist reduced the antagonist effect (FIG. 3). Thus agonist action can be detected by blockade of antagonist effect and fluorometry can be utilised to quantify the agonist effect.

Example 43b

Expression of the Dopamine D1 Receptor with an Inserted NLS (HA-D1-NLS), and Blockade of Antagonist Effect by Agonist Dose-Response and Detection with Fluorometry HEK cells were transfected with HA-D1-NLS in a multiwell plate were coated with poly-L-ornithine at a concentration of 50,000 cells per well. The cells were treated with the antagonist SCH 23390 (0.5 micromolar) for 48 hrs. The agonist SKF 81297 (100 nanomolar to 1 micromolar) together with SCH 23390 was added for the last hour of incubation. Following this, the cells were fixed with paraformaldehyde, and cell surface receptors were detected with a rat anti-HA antibody and then a goat anti-rat antibody conjugated to FITC. The fluorescent signal was detected by fluorometry (Cytofluor). The results are the average of five wells per experimental condition.

Figure 4:
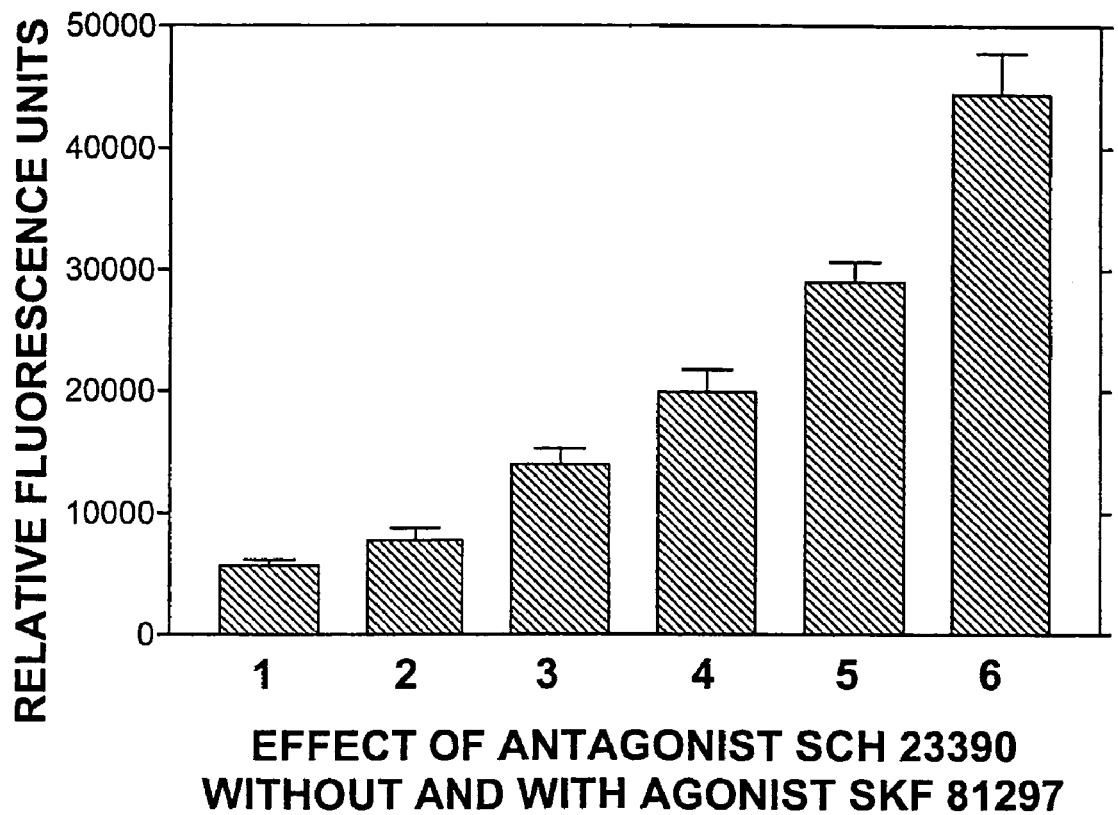
FIG. 4 shows cell surface fluorescence of HEK cells transfected with HA-dopamine D1 receptor-NLS and treated with 0.5 µM SCH23390 alone or together with various concentrations of SKF81297.

Treatment with SCH 23390 retained HA-D1-NLS on the cell surface (FIG. 4, Bar 1 vs. Bar 6). Short-term addition of the agonist resulted in a dose-dependent blockade of SCH 23390 effect. Removal of SCH 23390 from the cells for the last hour of incubation (and in the absence of agonist) resulted in a 33% loss of HA-D1-NLS receptors from the cell surface (FIG. 4, Bar 5 vs. Bar 6), whereas addition of agonist SKF 81297 100 nanomolar in the continued presence of SCH 23390 resulted in a 66% loss of receptors from the cell surface (FIG. 4, Bar 4 vs. Bar 6), up to a 78% loss of receptors with addition of SKF 81297 1 micromolar (FIG. 4, Bar 2 vs. Bar 6).

The effect of the antagonist SCH 23390 resulted in retention of receptor on the cell surface, indicating that this antagonist reduced receptor trafficking from the cell surface. The concomitant addition of agonist reduced the antagonist effect and accelerated the removal of the receptor from the cell surface in a dose-responsive manner. Thus interacting compounds can be detected by blockade of the effect of compounds that retain the NLS-containing receptor at the cell surface and fluorometry can be utilized to quantify the effect.

Example 44

Expression of the Dopamine D1 Receptor with an Inserted (D1-NLS), Treatment with (+)butaclamol 10 Micromolar and Detection with Radioligand Binding HEK cells were transfected with DNA encoding D1-NLS and treated with (+)butaclamol (10 micromolar) or left untreated. After 48 hours, the cells were washed, harvested, lysed and homogenised by polytron. The membrane fraction was collected by centrifugation and then layered over 35% sucrose solution and centrifuged, at 30,000 rpm at 4 degrees C. for 90 min to collect the heavy membrane fraction.

The membrane fractions were subjected to radioligand binding assay using [$^3$H]-SCH23390 with (+)butaclamol (10 micromolar) used to define specific binding. The incubation was at room temperature for 2 hours, followed by rapid filtration and quantitation by scintillation counting.

Figure 5:
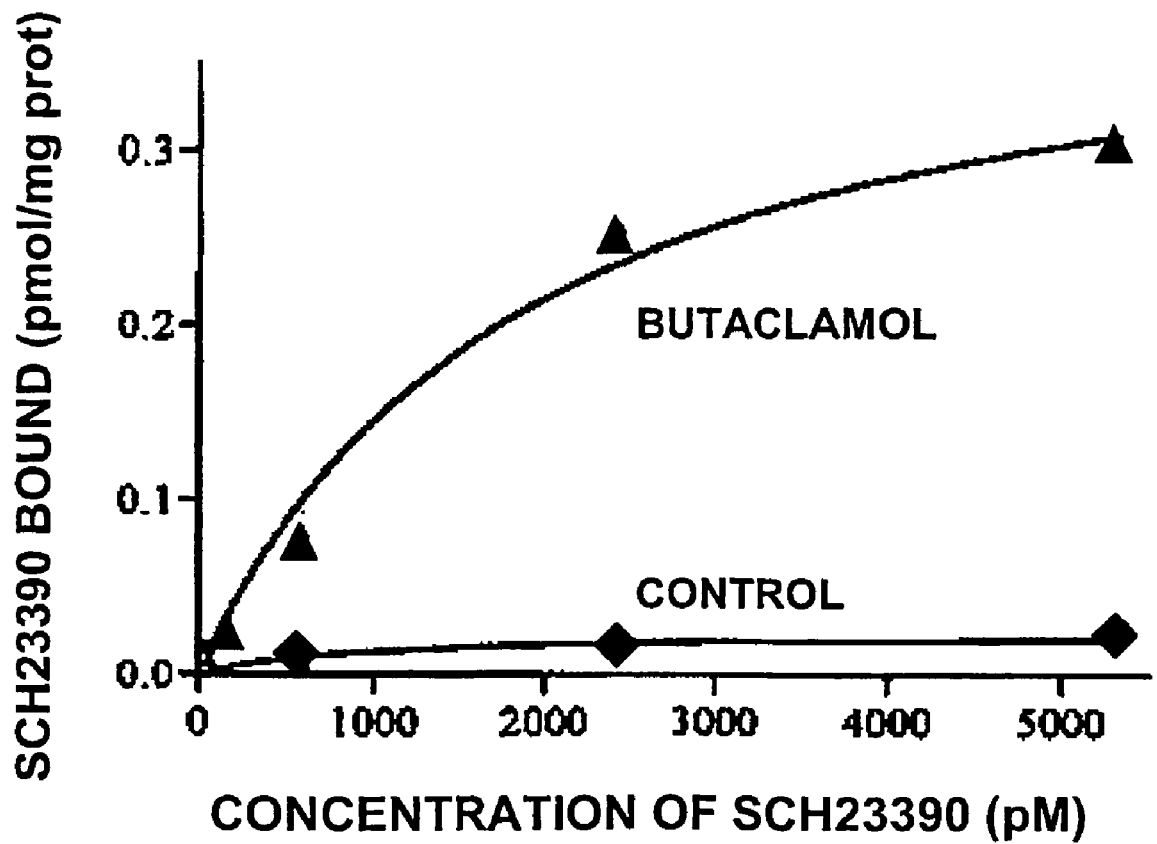
FIG. 5 shows the amount of $^3$H-SCH 23390 bound to the cell membrane fraction of HEK cells transfected with dopamine D1 receptor-NLS and treated with butaclamol (▲) or control untreated cells (■).

Antagonist treatment of D1-NLS prevented its translocation off the cell surface and to the nucleus and the receptor retained on the cell surface was quantified by radioligand binding assay (FIG. 5).

Example 45

Expression of the Dopamine D1 Receptor with an Inserted NLS (D1-NLS), Treatment with (+)butaclamol 500 Nanomolar and Detection with Radioligand Binding HEK cells were transfected with DNA encoding D1-NLS and treated with (+)butaclamol 500 nanomolar or left untreated. After 48 hours, the cells were washed, harvested, lysed and homogenised by polytron. The membrane fraction was collected by centrifugation and then layered over 35% sucrose solution and centrifuged at 30,000 rpm at 4 degrees C. for 90 min to collect the heavy membrane fraction.

The membranes were subjected to radioligand binding assay using [$^3$H]-SCH23390 with (+)butaclamol 10 micromolar used to define specific binding. The incubation was at room temperature for 2 hours, followed by rapid filtration and quantitation by scintillation counting. Results are shown in Tables 4 and 5.

TABLE 4

| Control plasma membrane fraction | | | | | |
|---|---|---|---|---|---|
| Sample 1 | Sample 2 | Mean | NSB | SB | pmol/mg prot |
| 2739 | 3596 | 3167 | 1077 | 2090 | 1.42 |

TABLE 5

| Butaclamol treated plasma membrane fraction | | | | | |
|---|---|---|---|---|---|
| Sample 1 | Sample 2 | Mean | NSB | SB | pmol/mg prot |
| 16419 | 15362 | 15890 | 471 | 15419 | 13.15 |

NSB: non-specific binding
SB: specific binding

Antagonist treatment with (+)butaclamol of D1-NLS prevented its translocation to the nucleus and the receptor retained on the cell surface was quantified by radioligand binding assay.

Example 46

Expression of the Dopamine D1 Receptor with an Inserted NLS (D1-NLS), Treatment with (+)butaclamol 100 Nanomolar and Detection with Radioligand Binding HEK cells were transfected with DNA encoding D1-NLS and treated with (+)butaclamol 100 nanomolar or left untreated. After 48 hours, the cells were washed, harvested, lysed and homogenised by polytron. The membrane fraction was collected by centrifugation and then layered over 35% sucrose solution and centrifuged at 30,000 rpm at 4 degrees C. for 90 min to collect the heavy membrane fraction.

The membranes were subjected to radioligand binding assay using [$^3$H]-SCH23390 with (+)butaclamol (10 micromolar) to define specific binding. The incubation was at room temperature for 2 hours, followed by rapid filtration and quantitation by scintillation counting.

Antagonist treatment with (+)butaclamol (100 nanomolar) prevented D1-NLS translocation to the nucleus and the receptor retained on the cell surface was quantified by radioligand binding assay. In the absence of butaclamol treatment, 0.03 pmol/mg protein of receptor was detected in the cell surface membranes, and with butaclamol treatment, 0.09 pmol/mg protein of receptor was detected in the cell surface membranes.

Example 47

Expression of the Epidermal Growth Factor Receptor (Tyrosine Kinase Receptor) EGFR-GFP and EGFR-NLS-GFP HEK cells were transfected with DNA encoding EGFR-NLS-GFP (2 micrograms). HEK cells were also transfected with DNA encoding EGFR-GFP (2 micrograms) and incubated for 24 hours.

EGFR-GFP was expressed on the cell surface in 73% of cells and 12% of cells had receptor in the nucleus. EGFR-NLS-GFP was expressed in the nucleus in 91% of cells and 0% of cells had receptor on the cell surface. The incorporation of a NLS into the sequence of the EGF receptor induced robust translocation off the cell surface and into the nucleus.

Example 48

Expression of the Low Density Lipoprotein Receptor (LDL-GFP)

HEK cells were transfected with DNA encoding the LDL-GFP (2 micrograms) and incubated for 24 hours. The receptor was expressed on the cell surface in 67% of cells and in the nucleus in 8% of cells.

The LDL receptor is expressed on the cell surface in the majority of cells with not many cells containing receptor in the nucleus.

Example 49

Expression of the LDL Receptor with a NLS (LDL-NLS-GFP)

HEK cells were transfected with DNA encoding LDL-NLS-GFP (2 micrograms), and DsRED-NUC (2 micrograms), and incubated for 48 hours. Cells were examined by confocal microscopy.

LDL-NLS-GFP was expressed in the nucleus in 22% of cells, and on the cell surface in 67%. The incorporation of a NLS into the LDL receptor induced receptor translocation into the nucleus.

Example 50

Expression of the Erythropoietin Receptor (Cytokine Receptor) EPO-GFP and EPO-NLS-GFP HEK cells were transfected with DNA encoding EPO-NLS-GFP (2 micrograms). HEK cells were transfected with EPO-GPF (2 micrograms). The cells were also transfected with DsRed-NUC (2 micrograms). The cells were incubated for 48 hours and were examined by confocal microscopy.

The EPO-NLS-GFP was located in the nucleus of 72% of cells and on the cell surface in 0% of cells. The EPO-GFP was located on the cell surface in 79%) of cells and 28% of cells had receptor expression in the nucleus. The incorporation of a NLS into the sequence of the EPO receptor induced translocation off the cell surface and into the nucleus.

Example 51

Expression of the Serotonin Transporter with a NLS (SERT-NLS-GFP) and Treatment with Sertraline HEK cells were transfected with DNA encoding SERT-NLS-GFP (2 micrograms of DNA) and treated with sertraline (final concentration 500 nanomolar) for 48 hours. At 6, 22, 30 and 42 hours after transfection, the cells were treated with sertraline. The cells were examined by confocal microscopy.

In the untreated cells expressing SERT-NLS-GFP, 0% of the cells had transporter expression on the cell surface and 75% of the cells had transporter expression in the nucleus and cytoplasm.

Following sertraline treatment, 69% of the cells had SERT-NLS-GFP transporter expression on the cell surface and cytoplasm, and 21% of the cells had transporter expression in the nucleus and cytoplasm. Thus treatment with sertraline inhibited the SERT-NLS-GFP from translocating off the cell surface and trafficking to the nucleus.

Example 52

Expression of D1 Dopamine Receptor with an Alternate NLS (D1-NLS2-GFP) and Treatment with Antagonists HEK cells were transfected with DNA encoding D1-NLS2-GFP (2 micrograms) and treated with (+)butaclamol or SCH 23390 (1 micromolar) for 48 hrs. Nuclei were visualised with DsRed-nuc (2 micrograms). Cells were examined by confocal microscopy.

With butaclamol treatment, 81% of cells had receptor on the cell surface or in cytoplasm and 19% of cells had receptor expression in the nucleus. With SCH 23390 treatment, 78% of cells had receptor on the cell surface or in cytoplasm and 22% of cells had receptor expression in the nucleus In the untreated cells, 89% of cells had receptor expression in the nucleus and cytoplasm.

Thus treatment with the dopamine D1 antagonists prevented D1-NLS2-GFP receptor translocation off the surface and trafficking to or toward the nucleus.

The present invention is not limited to the features of the embodiments described herein, but includes all variations and modifications within the scope of the claims.

REFERENCES

Bailey et al., (2001), Expert Opinion in Therapeutics, v. 11, p. 1861-1887;
Barak et al., (1997), J. Biol. Chem., v. 272, p. 27497-27500;
Chen et al., (2000), Am. J. Physiol. Renal Physiol., v. 279, F440-F448;
George et al., (2000), J. Biol. Chem., v. 275, p. 26128-26135;
George et al., (2002), Nature Reviews (2002), v. 1, p. 808-820;
Gorlich et al., (1996), Science, v. 271, p. 1513-1518;
Grotzinger, (2002), Biochim. Biophys. Acta, v. 1592, p. 215-223;

Hailey et al., (2002), Methods in Enzymology, v. 351, p. 3441;
Hanahan et al., (1996), Cell, v. 86, p. 353-364;
Howard et al., (2001), Trends in Pharmacol. Sci., v. 22, p. 132-140;
Jans et al, (2000), Bioessays v. 22:532-544;
Lee et al., (2002), Expert Opinion in Therapeutic Targets, v. 6, p. 185-202;
Lu et al., (1998), Endocrinol., v. 139, p. 365-375;
Masson et al., (1999), Pharmacol Reviews, 51:439-464;
Matz et al., (1999), Nature Biotech., v. 17, p. 969-973;
Nakae et al., (2001), Endo. Reviews., v. 22, p 818-835;
Nicholson et al., (2001), Eur. J. Cancer, v. 37, Suppl. 4, p. S9-S15;
Prasher et al., (1992), Gene, v. 111, p. 129;
Schlenstedt et al., (1996), FEBS Lett., v. 389, p. 75-79;
Shawver et al., (2002), Cancer Cell, v. 1, p. 117-123;
Smith, (2002), Nature v. 418, p. 453-459;
Strickland et al., (2002) Trends Endo. Metab., v. 13, p 66-74;
Watson et al, (2000), Bone v. 26, p. 221-225;
Weis et al., (1998), Trends in Biochem., v. 23, p. 185-189;
White et al., Nature, v. 396, p. 679-682 (1998);

TABLE 1

EXAMPLES OF NUCLEAR LOCALISATION SEQUENCES
(adapted from Jans et al. 2002)

| Protein | Nuclear Localisation Sequence | (SEQ ID NO) |
| --- | --- | --- |
| Human a1 T-ag | PKKKRKV | 129 |
| CBP80 | RRR-(11 aa)-KRRK | 130 |
| DNA helicase Q1 | KK-(15 aa)-KKRK | 131 |
| BRCA1 | KRKRRP, PKKNRLRRK | 132, 133 |
| Mitosin | KRQR-(20 aa)-KKSKK | 134 |
| Myc | PAAKRVKLD | 135 |
| NF-kB p50 | QRKRQK | 136 |
| NF-kB p65 | HRIEEKRKRTYETFKSI | 137 |
| HIV1422 | KKKYKLK | 138 |
| HIV1423 | KSKKKAQ | 139 |
| Human a2 T-ag | PKKKRKV | 129 |
| NF-kB p50 | QRKRQK | 136 |
| DNA helicase Q1 | KK-(15 aa)-KKRK | 131 |
| LEF-1 | KKKKRKREK | 140 |
| EBNA1 | LKRPRSPSS | 141 |
| HIV-1 IN | KRK-(22 aa)-KELQKQITK | 142 |
| HIV-1 MA | GKKKYKLKH | 143 |
| HIV1422 | KKKYKLK | 144 |
| HIV1423 | KSKKKAQ | 145 |
| RCP 4.1R | EED-(350 aa)-KKKRERLD | 146 |
| Human a3 T-ag | PKKKRKV | 129 |
| DNA helicase Q1 | CYFQKKAANMLQQSGSKNTGAKKRK | 147 |
| tTS | DILRR-(323 aa)-PKQKRK | 148 |
| Human a4 T-ag | PKKKRKV | 129 |
| Mouse a1 LEF-1 | KKKKRKREK | 140 |
| Mouse a2 T-agáCK2 site | SSDDEATADSQHSTPPKKKRKV | 149 |
| Impa-P1) T-ag | PKKKRKV | 129 |

TABLE 1-continued

EXAMPLES OF NUCLEAR LOCALISATION SEQUENCES
(adapted from Jans et al. 2002)

| Protein | Nuclear Localisation Sequence | (SEQ ID NO) |
| --- | --- | --- |
| N1N2 | RKKRK-(9 aa)-KAKKSK | 150 |
| RB | KR-(11 aa)-KKLR | 151 |
| Dorsal áPK˘A site | RRPS-(22 aa)-RRKRQK | 152 |
| CBP80 | RRR-(11 aa)-KRRK | 153 |
| DNA helicase Q1 | KK-(15 aa)-KKRK | 131 |
| LEF-1 | KKKKRKREK | 140 |
| Mouse a2 T-agáCK2 | SSDDEATADSQHSTPPKKKRKV | 149 |
| Impa-P1) T-ag | PKKKRKV | 129 |
| N1N2 | RKKRK-(9 aa)-KAKKSK | 150 |
| RB | KR-(11 aa)-KKLR | 151 |
| Dorsal áPK˘A | RRPS-(22 aa)-RRKRQK | 152 |
| CBP80 | RRR-(11 aa)-KRRK | 153 |
| DNA helicase Q1 | KK-(15 aa)-KKRK | 131 |
| LEF-1 | KKKKRKREK | 140 |
| Xenopus a1 T-ag | PKKKRKV | 129 |
| Nucleoplasmin | KR-(10 aa)-KKKL | 154 |
| Yeast a1 T-ag | PKKKRKV | 129 |
| (SRP1, Kap60) T-agáCK2 | SSDDEATADSQHSTPPKKKRKV | 149 |
| N1N2 | RKKRK-(9 aa)-KAKKSK | 150 |
| HIV-1 IN | KRK-(22 aa)-KELQKQITK | 142 |
| Plant a1 T-ag | PKKKRKV | 129 |
| T-agáCK2 | SSDDEATADSQHSTPPKKKRKV | 149 |
| Opaque-2 | RKRK-(7 aa)-RRSRYRK | 155 |
| R Protein (Maize) | MISEALRKA | 156 |
| N1N2 | RKKRK-(9 aa)-KAKKSK | 150 |

RAG-1, recombination activating protein 1;

RCP, red cell protein;

RB, Retinoblastoma protein;

STAT, signal transducer and activator of transcription (TF);

CBP80, Cap-binding protein;

LEF, Lymphocyte enhancer factor;

EBNA, Epstein-Barr virus nuclear antigen;

IN, HIV-1 integrase;

tTG, tissue transglutaminase;

ICP, Infected cell protein.

We claim:

1. A method for screening a candidate compound for its ability to interact with at least one transmembrane protein comprising:
    transfecting a eukaryotic cell with at least one nucleotide sequence encoding a protein comprising a transmembrane protein containing at least one nuclear localisation sequence (NLS) and a detectable moiety and permitting expression of the encoded protein in the cell;
    contacting the cell with a candidate compound; and
    determining the distribution of the expressed protein in the cell by detecting the distribution of the detectable moiety in the cell;
    wherein detection of an altered distribution of the detectable moiety in the cell relative to the distribution of the detectable moiety in a control cell not contacted with the candidate compound indicates that the compound interacts with the transmembrane protein; and
    wherein the wild type transmembrane protein lacks an NLS and the nucleotide sequence encoding the transmembrane protein is modified to encode an NLS.

2. The method of claim 1 wherein the detectable moiety is a detectable peptide comprising an antigenic portion of the amino acid sequence of the transmembrane protein and/or wherein the nucleotide sequence encodes a fusion protein comprising a transmembrane protein containing at least one NLS and a detectable moiety.

3. The method of claim 1 wherein the nucleotide sequence is modified to encode an NLS selected from Table 1 or wherein the nucleotide sequence is modified to encode an amino acid sequence selected from the group consisting of KKFKR (SEQ ID NO: 158), PKKKRKV (SEQ ID NO: 154) and AFSAKKFKR (SEQ ID NO: 159).

4. The method of claim 1 wherein the eukaryotic cell is a selected from the group consisting of a mammalian cell, selected from the group consisting of HEK, COS and CHO cells, a yeast cell, an insect cell, a nematode cell, a plant cell and a fungal cell.

5. The method of claim 2 wherein the detectable moiety is an antigenic peptide and the distribution of the antigenic peptide in the cell is determined by allowing it to bind to an antibody-based detection system comprising an antibody specific for the antigenic peptide selected from the group consisting of an antibody-based detection system comprising a first antibody specific for the antigenic peptide and a second antibody carrying a detectable label and specific for the first antibody and an antibody-based detection system comprising a first antibody specific for the antigenic peptide and carrying a detectable label, wherein the detectable label is selected from the group consisting of an optically detectable label, a luminescent and a fluorescent label.

6. The method of claim 2 wherein the detectable moiety is a polypeptide selected from the group consisting of green fluorescent protein, red fluorescent protein and modified variants thereof.

7. The method of claim 1 wherein the transmembrane protein is selected from the group consisting of a G protein coupled receptor (GPCR), a transporter, a cytokine receptor, a tyrosine kinase receptor and a low density lipoprotein (LDL) receptor.

8. The method of claim 7 wherein the transmembrane protein is a GPCR.

9. The method of claim 8 wherein the GPCR is selected from the group consisting of a dopamine D1 receptor, a dopamine D2 receptor, a dopamine D3 receptor, a dopamine D5 receptor, a histamine 1 receptor, a cysteinyl leukotriene receptor 1, a cysteinyl leukotriene receptor 2, an opioid receptor, a muscarinic receptor, a serotonin receptor, a beta2-adrenergic receptor and a metabotropic glutamate 4 receptor.

10. The method of claim 7 wherein the transmembrane protein is a transporter selected from the group consisting of a dopamine transporter and a serotonin transporter, a cytokine receptor selected from the group consisting of an erythropoietin receptor and an insulin receptor, a tyrosine kinase receptor selected from the group consisting of an epidermal growth factor receptor and an insulin receptor, and a low density lipoprotein receptor.

11. The method of claim 1 wherein the cell is transfected with a plurality of nucleotide sequences, each of said sequences encoding a protein comprising a different transmembrane protein containing at least one NLS and wherein each of said nucleotide sequences encodes a protein comprising a different detectable moiety or wherein at least one detectable moiety is common to at least two encoded proteins.

12. The method of claim 1 wherein the cell is contacted with a compound known to interact with the at least one transmembrane protein prior to contacting the cell with the candidate compound and
   wherein detection of an altered distribution of the detectable moiety in the cell relative to the distribution of the detectable moiety in a control cell contacted with the compound known to interact with the transmembrane protein but not contacted with the candidate compound indicates that the candidate compound interacts with the transmembrane protein.

13. The method of claim 1 wherein detection of an altered distribution of the detectable moiety in the cell comprises detection of a reduced level or an increased level of the detectable moiety associated with the cell membrane.

14. The method of claim 1 wherein detection of an altered distribution of the detectable moiety in the cell comprises detection of a reduced level or an increased level of the detectable moiety in the nucleus of the cell.

15. A method for screening a candidate compound for its ability to interact with at least one transmembrane protein comprising:
   transfecting a eukaryotic cell with at least one nucleotide sequence encoding an NLS-containing transmembrane protein and permitting expression of the encoded protein in the cell;
   contacting the cell with a candidate compound; and
   determining the level of NLS-containing transmembrane protein remaining at the cell membrane by isolating the cell membrane fraction of the cell, contacting the fraction with a labelled ligand of the transmembrane protein and determining the level of binding of the ligand to the fraction;
   wherein detection of an altered level of the transmembrane protein at the cell membrane relative to the level at the cell membrane in a control cell not contacted with the candidate compound indicates that the compound interacts with the transmembrane protein, and;
   wherein the wild type transmembrane protein lacks an NLS and the nucleotide sequence encoding the transmembrane protein is modified to encode an NLS.

16. The method of claim 15 wherein the labelled ligand is a radio-labelled ligand.

17. The method of claim 15 wherein the nucleotide sequence is modified to encode an NLS selected from Table 1 or wherein the nucleotide sequence is modified to encode an amino acid sequence selected from the group consisting of KKFKR, PKKKRKV and AFSAKKFKR.

18. The method of claim 15 wherein the eukaryotic cell is selected from the group consisting of a mammalian cell, selected from the group consisting of HEK, COS and CHO cells, a yeast cell, an insect cell, a nematode cell, a plant cell and a fungal cell.

19. The method of claim 15 wherein the transmembrane protein is selected from the group consisting of a G protein coupled receptor (GPCR), a transporter, a cytokine receptor, a tyrosine kinase receptor and a low density lipoprotein (LDL) receptor.

20. The method of claim 19 wherein the transmembrane protein is a GPCR.

21. The method of claim 20 wherein the GPCR is selected from the group consisting of a dopamine D1 receptor, a dopamine D2 receptor, a dopamine D3 receptor, a dopamine D5 receptor, a histamine 1 receptor, a cysteinyl leukotriene receptor 1, a cysteinyl leukotriene receptor 2, an opioid receptor, a muscarinic receptor, a serotonin receptor, a beta2-adrenergic receptor, and a metabotropic glutamate 4 receptor.

22. The method of claim 19 wherein the transmembrane protein is a transporter selected from the group consisting of a dopamine transporter and a serotonin transporter, a cytokine receptor selected from the group consisting of an erythropoietin receptor and an insulin receptor, a tyrosine kinase receptor selected from the group consisting of an epidermal growth factor receptor and an insulin receptor, and a low density lipoprotein receptor.

23. The method of claim 15 wherein the cell is transfected with a plurality of nucleotide sequences, each of said sequences encoding a protein comprising a different transmembrane protein containing at least one NLS and wherein each of said nucleotide sequences encodes a protein comprising a different detectable moiety or wherein at least one detectable moiety is common to at least two encoded proteins.

24. The method of claim 15 wherein detection of an altered distribution of the detectable moiety comprises detection of a reduced level or an increased level of the detectable moiety associated with the cell membrane.

* * * * *

UNITED STATES PATENT AND TRADEMARK OFFICE
CERTIFICATE OF CORRECTION

PATENT NO. : 7,309,576 B2
APPLICATION NO. : 10/509787
DATED : December 18, 2007
INVENTOR(S) : Brian F. O'Dowd and Susan R. George Page 1 of 1

It is certified that error appears in the above-identified patent and that said Letters Patent is hereby corrected as shown below:

In the specification

| COLUMN | LINE | ERROR |
|---|---|---|
| 25 | 26 | "5HT1B-Eland" should read --5HT1B-E1 and-- |
| 37 | 63 | "DL-NLS-RFP" should read --D1-NLS-RFP-- |
| 38 | 4 | "DL-GFP" should read --D1-GFP-- |
| 38 | 14 | "DL-GFP" should read --D1-GFP-- |
| 55 | 2 | "3441" should read --34-41-- |

Signed and Sealed this
Twenty-sixth Day of April, 2016

Michelle K. Lee
*Director of the United States Patent and Trademark Office*

SEQUENCE LISTING

<160> NUMBER OF SEQ ID NOS: 158

<210> SEQ ID NO 1
<211> LENGTH: 49
<212> TYPE: DNA
<213> ORGANISM: Artificial sequence
<220> FEATURE:
<223> OTHER INFORMATION: primer

<400> SEQUENCE: 1

```
gaggactctg aacaccgaat tcgccgccat ggacgggact gggctggtg            49

<210> SEQ ID NO 2
<211> LENGTH: 45
<212> TYPE: DNA
<213> ORGANISM: Artificial sequence
<220> FEATURE:
<223> OTHER INFORMATION: primer

<400> SEQUENCE: 2
gtgtggcagg attcatctgg gtaccgcggt tgggtgctga ccgtt               45

<210> SEQ ID NO 3
<211> LENGTH: 51
<212> TYPE: DNA
<213> ORGANISM: Artificial sequence
<220> FEATURE:
<223> OTHER INFORMATION: primer

<400> SEQUENCE: 3
cctaagaggg ttgaaaatct tttaaatttt ttagcattaa aggcataaat g         51

<210> SEQ ID NO 4
<211> LENGTH: 48
<212> TYPE: DNA
<213> ORGANISM: Artificial sequence
<220> FEATURE:
<223> OTHER INFORMATION: primer

<400> SEQUENCE: 4
gcctttaatg ctaaaaaatt taaaagattt tcaaccctct taggatgc             48

<210> SEQ ID NO 5
<211> LENGTH: 19
<212> TYPE: PRT
<213> ORGANISM: Artificial sequence
<220> FEATURE:
<223> OTHER INFORMATION: synthesized

<400> SEQUENCE: 5

Asn Pro Ile Ile Tyr Ala Phe Asn Ala Asp Phe Arg Lys Ala Phe Ser
1               5                   10                  15

Thr Leu Leu

<210> SEQ ID NO 6
<211> LENGTH: 19
<212> TYPE: PRT
<213> ORGANISM: Artificial sequence
<220> FEATURE:
<223> OTHER INFORMATION: synthesized

<400> SEQUENCE: 6

Asn Pro Ile Ile Tyr Ala Phe Asn Ala Lys Lys Phe Lys Arg Phe Ser
1               5                   10                  15

Thr Leu Leu

<210> SEQ ID NO 7
<211> LENGTH: 27
<212> TYPE: DNA
<213> ORGANISM: Artificial sequence
<220> FEATURE:
<223> OTHER INFORMATION: primer

<400> SEQUENCE: 7
```

```
taccottacg acgtgccgga ttacgcc                                                27
```

<210> SEQ ID NO 8
<211> LENGTH: 9
<212> TYPE: PRT
<213> ORGANISM: Artificial sequence
<220> FEATURE:
<223> OTHER INFORMATION: synthesized

<400> SEQUENCE: 8

Tyr Pro Tyr Asp Val Pro Asp Tyr Ala
1               5

<210> SEQ ID NO 9
<211> LENGTH: 84
<212> TYPE: DNA
<213> ORGANISM: Artificial sequence
<220> FEATURE:
<223> OTHER INFORMATION: primer

<400> SEQUENCE: 9

```
ggatccacta gtaacggccg ccagaccacc atgggatacc cgtacgacgt ccccgactac     60
gcaaggactc tgaacacctc tgcc                                            84
```

<210> SEQ ID NO 10
<211> LENGTH: 36
<212> TYPE: DNA
<213> ORGANISM: Artificial sequence
<220> FEATURE:
<223> OTHER INFORMATION: primer

<400> SEQUENCE: 10

```
ggccgccagc tgcgagttca ggttgggtgc tgaccg                               36
```

<210> SEQ ID NO 11
<211> LENGTH: 16
<212> TYPE: PRT
<213> ORGANISM: Artificial sequence
<220> FEATURE:
<223> OTHER INFORMATION: synthesized

<400> SEQUENCE: 11

Met Arg Thr Leu Asn Thr Ser Ala Met Asp Gly Thr Gly Leu Val Val
1               5                   10                  15

<210> SEQ ID NO 12
<211> LENGTH: 26
<212> TYPE: PRT
<213> ORGANISM: Artificial sequence
<220> FEATURE:
<223> OTHER INFORMATION: synthesized

<400> SEQUENCE: 12

Met Gly Tyr Pro Tyr Asp Val Pro Asp Tyr Ala Arg Thr Leu Asn Thr
1               5                   10                  15

Ser Ala Met Asp Gly Thr Gly Leu Val Val
            20                  25

<210> SEQ ID NO 13
<211> LENGTH: 36
<212> TYPE: DNA
<213> ORGANISM: Artificial sequence
<220> FEATURE:
<223> OTHER INFORMATION: primer

<400> SEQUENCE: 13
ggaaagttct tttaagaaga agttcaaaag agaaac                                36

<210> SEQ ID NO 14
<211> LENGTH: 36
<212> TYPE: DNA
<213> ORGANISM: Artificial sequence
<220> FEATURE:
<223> OTHER INFORMATION: primer

<400> SEQUENCE: 14
gtttctcttt tgaacttctt cttaaaagaa ctttcc                                36

<210> SEQ ID NO 15
<211> LENGTH: 17
<212> TYPE: PRT
<213> ORGANISM: Artificial sequence
<220> FEATURE:
<223> OTHER INFORMATION: synthesized

<400> SEQUENCE: 15

Gln Pro Glu Ser Ser Phe Lys Met Ser Phe Lys Arg Glu Thr Lys Val
1               5                   10                  15

Leu

<210> SEQ ID NO 16
<211> LENGTH: 17
<212> TYPE: PRT
<213> ORGANISM: Artificial sequence
<220> FEATURE:
<223> OTHER INFORMATION: synthesized

<400> SEQUENCE: 16

Gln Pro Glu Ser Ser Phe Lys Lys Lys Phe Lys Arg Glu Thr Lys Val
1               5                   10                  15

Leu

<210> SEQ ID NO 17
<211> LENGTH: 37
<212> TYPE: DNA
<213> ORGANISM: Artificial sequence
<220> FEATURE:
<223> OTHER INFORMATION: primer

<400> SEQUENCE: 17
ccggtatgag aaaaagttta aacgcaaggc agccttc                               37

<210> SEQ ID NO 18
<211> LENGTH: 39
<212> TYPE: DNA
<213> ORGANISM: Artificial sequence
<220> FEATURE:
<223> OTHER INFORMATION: primer

<400> SEQUENCE: 18
ggctgccttg cgtttaaact ttttctcata ccggaaagg                             39

<210> SEQ ID NO 19
<211> LENGTH: 18
<212> TYPE: PRT
<213> ORGANISM: Artificial sequence
<220> FEATURE:
<223> OTHER INFORMATION: synthesized

<400> SEQUENCE: 19

Asn Pro Phe Arg Tyr Glu Arg Lys Met Thr Pro Lys Ala Ala Phe Ile
1               5                   10                  15

Leu Ile

<210> SEQ ID NO 20
<211> LENGTH: 18
<212> TYPE: PRT
<213> ORGANISM: Artificial sequence
<220> FEATURE:
<223> OTHER INFORMATION: synthesized

<400> SEQUENCE: 20

Asn Pro Phe Arg Tyr Glu Lys Lys Phe Lys Arg Lys Ala Ala Phe Ile
1               5                   10                  15

Leu Ile

<210> SEQ ID NO 21
<211> LENGTH: 39
<212> TYPE: DNA
<213> ORGANISM: Artificial sequence
<220> FEATURE:
<223> OTHER INFORMATION: primer

<400> SEQUENCE: 21
gtgctgccgt taaaaagttc aaacgcctgc ggtccaagg                     39

<210> SEQ ID NO 22
<211> LENGTH: 40
<212> TYPE: DNA
<213> ORGANISM: Artificial sequence
<220> FEATURE:
<223> OTHER INFORMATION: primer

<400> SEQUENCE: 22
ggaccgcagg cgtttgaact ttttaacggc agcacagacc                    40

<210> SEQ ID NO 23
<211> LENGTH: 18
<212> TYPE: PRT
<213> ORGANISM: Artificial sequence
<220> FEATURE:
<223> OTHER INFORMATION: synthesized

<400> SEQUENCE: 23

Leu Val Cys Ala Ala Val Ile Arg Phe Arg His Leu Arg Ser Lys Val
1               5                   10                  15

Thr Asn

<210> SEQ ID NO 24
<211> LENGTH: 18
<212> TYPE: PRT
<213> ORGANISM: Artificial sequence
<220> FEATURE:
<223> OTHER INFORMATION: synthesized

<400> SEQUENCE: 24

Leu Val Cys Ala Ala Val Lys Lys Phe Lys Arg Leu Arg Ser Lys Val
1               5                   10                  15

Thr Asn

<210> SEQ ID NO 25
<211> LENGTH: 44
<212> TYPE: DNA
<213> ORGANISM: Artificial sequence

```
<220> FEATURE:
<223> OTHER INFORMATION: primer

<400> SEQUENCE: 25
gcctttaatc ctaaaaaaaa agaaaggtt tcaaccctct tagg                    44

<210> SEQ ID NO 26
<211> LENGTH: 44
<212> TYPE: DNA
<213> ORGANISM: Artificial sequence
<220> FEATURE:
<223> OTHER INFORMATION: primer

<400> SEQUENCE: 26
cctaagaggg ttgaaacctt tcttttttt ttaggattaa aggc                   44

<210> SEQ ID NO 27
<211> LENGTH: 19
<212> TYPE: PRT
<213> ORGANISM: Artificial sequence
<220> FEATURE:
<223> OTHER INFORMATION: synthesized

<400> SEQUENCE: 27

Asn Pro Ile Ile Tyr Ala Phe Asn Ala Asp Phe Arg Lys Ala Phe Ser
 1               5                  10                  15

Thr Leu Leu

<210> SEQ ID NO 28
<211> LENGTH: 19
<212> TYPE: PRT
<213> ORGANISM: Artificial sequence
<220> FEATURE:
<223> OTHER INFORMATION: synthesized

<400> SEQUENCE: 28

Asn Pro Ile Ile Tyr Ala Phe Asn Pro Lys Lys Lys Arg Lys Val Ser
 1               5                  10                  15

Thr Leu Leu

<210> SEQ ID NO 29
<211> LENGTH: 45
<212> TYPE: DNA
<213> ORGANISM: Artificial sequence
<220> FEATURE:
<223> OTHER INFORMATION: primer

<400> SEQUENCE: 29
ggccgtggct ccaccgaatt cgccgccatg gatccactga atctg                 45

<210> SEQ ID NO 30
<211> LENGTH: 43
<212> TYPE: DNA
<213> ORGANISM: Artificial sequence
<220> FEATURE:
<223> OTHER INFORMATION: primer

<400> SEQUENCE: 30
ctgtgcgggc aggcagggta ccgcgcagtg gaggatcttc agg                   43

<210> SEQ ID NO 31
<211> LENGTH: 44
<212> TYPE: DNA
<213> ORGANISM: Artificial sequence
<220> FEATURE:
```

-continued

<223> OTHER INFORMATION: primer

<400> SEQUENCE: 31
caccaccttc aacaaaaaat tcaaaagagc cttcctgaag atcc    44

<210> SEQ ID NO 32
<211> LENGTH: 44
<212> TYPE: DNA
<213> ORGANISM: Artificial sequence
<220> FEATURE:
<223> OTHER INFORMATION: primer

<400> SEQUENCE: 32
ggatcttcag gaaggctctt ttgaattttt tgttgaaggt ggtg    44

<210> SEQ ID NO 33
<211> LENGTH: 46
<212> TYPE: DNA
<213> ORGANISM: Artificial sequence
<220> FEATURE:
<223> OTHER INFORMATION: primer

<400> SEQUENCE: 33
ggcatcacgc acctcaagct tgccgccatg gcatctctga gtcagc    46

<210> SEQ ID NO 34
<211> LENGTH: 45
<212> TYPE: DNA
<213> ORGANISM: Artificial sequence
<220> FEATURE:
<223> OTHER INFORMATION: primer

<400> SEQUENCE: 34
gagtgttccc tcttctgcgg taccgcgcaa gacaggatct tgagg    45

<210> SEQ ID NO 35
<211> LENGTH: 17
<212> TYPE: DNA
<213> ORGANISM: Artificial sequence
<220> FEATURE:
<223> OTHER INFORMATION: primer

<400> SEQUENCE: 35
aatacgactc actatag    17

<210> SEQ ID NO 36
<211> LENGTH: 46
<212> TYPE: DNA
<213> ORGANISM: Artificial sequence
<220> FEATURE:
<223> OTHER INFORMATION: primer

<400> SEQUENCE: 36
cgccagtgtg atggataatg gtaccgcatg gaatccattc ggggtg    46

<210> SEQ ID NO 37
<211> LENGTH: 24
<212> TYPE: DNA
<213> ORGANISM: Artificial sequence
<220> FEATURE:
<223> OTHER INFORMATION: primer

<400> SEQUENCE: 37
gcgccaatga gcctccccaa ttcc    24

```
<210> SEQ ID NO 38
<211> LENGTH: 25
<212> TYPE: DNA
<213> ORGANISM: Artificial sequence
<220> FEATURE:
<223> OTHER INFORMATION: primer

<400> SEQUENCE: 38
gagcctccct taggagcgaa tatgc                                  25

<210> SEQ ID NO 39
<211> LENGTH: 36
<212> TYPE: DNA
<213> ORGANISM: Artificial sequence
<220> FEATURE:
<223> OTHER INFORMATION: primer

<400> SEQUENCE: 39
cgcctgcagg ccgccatgag cctccccaat tcctcc                      36

<210> SEQ ID NO 40
<211> LENGTH: 34
<212> TYPE: DNA
<213> ORGANISM: Artificial sequence
<220> FEATURE:
<223> OTHER INFORMATION: primer

<400> SEQUENCE: 40
ccggtggatc ccgggccccg gagcgaatat gcag                        34

<210> SEQ ID NO 41
<211> LENGTH: 63
<212> TYPE: DNA
<213> ORGANISM: Artificial sequence
<220> FEATURE:
<223> OTHER INFORMATION: primer

<400> SEQUENCE: 41
gggcccggga gcgaatatgc agaattctct tgaatgtcct cttgaatttt ttattgcaca    60
agg                                                          63

<210> SEQ ID NO 42
<211> LENGTH: 35
<212> TYPE: DNA
<213> ORGANISM: Artificial sequence
<220> FEATURE:
<223> OTHER INFORMATION: primer

<400> SEQUENCE: 42
aagaattcgc caccatggat gaaacaggaa atctg                       35

<210> SEQ ID NO 43
<211> LENGTH: 30
<212> TYPE: DNA
<213> ORGANISM: Artificial sequence
<220> FEATURE:
<223> OTHER INFORMATION: primer

<400> SEQUENCE: 43
gggtaccgct actttacata tttcttctcc                             30

<210> SEQ ID NO 44
<211> LENGTH: 38
<212> TYPE: DNA
<213> ORGANISM: Artificial sequence
<220> FEATURE:
```

-continued

<223> OTHER INFORMATION: primer

<400> SEQUENCE: 44
ttcttttctg ggaaaaaatt taagagaagg ctgtctac                    38

<210> SEQ ID NO 45
<211> LENGTH: 37
<212> TYPE: DNA
<213> ORGANISM: Artificial sequence
<220> FEATURE:
<223> OTHER INFORMATION: primer

<400> SEQUENCE: 45
tgtagacagc cttctcttaa atttttccc agaaaag                     37

<210> SEQ ID NO 46
<211> LENGTH: 48
<212> TYPE: DNA
<213> ORGANISM: Artificial sequence
<220> FEATURE:
<223> OTHER INFORMATION: primer

<400> SEQUENCE: 46 cttttgtgt ctgtttctga attcgccacc atggagagaa aatttatg          48

<210> SEQ ID NO 47
<211> LENGTH: 46
<212> TYPE: DNA
<213> ORGANISM: Artificial sequence
<220> FEATURE:
<223> OTHER INFORMATION: primer

<400> SEQUENCE: 47
gaacaggtct catctaagag gtaccgctac tcttgtttcc tttctc           46

<210> SEQ ID NO 48
<211> LENGTH: 37
<212> TYPE: DNA
<213> ORGANISM: Artificial sequence
<220> FEATURE:
<223> OTHER INFORMATION: primer

<400> SEQUENCE: 48
gctgggaaaa aatttaaaag aagactaaag tctgcac                     37

<210> SEQ ID NO 49
<211> LENGTH: 38
<212> TYPE: DNA
<213> ORGANISM: Artificial sequence
<220> FEATURE:
<223> OTHER INFORMATION: primer

<400> SEQUENCE: 49
gtcttctttt aaatttttc ccagcaaagt aatagagc                     38

<210> SEQ ID NO 50
<211> LENGTH: 26
<212> TYPE: DNA
<213> ORGANISM: Artificial sequence
<220> FEATURE:
<223> OTHER INFORMATION: primer

<400> SEQUENCE: 50
ccccacctag ccaccatgaa cacttc                                 26

<210> SEQ ID NO 51
<211> LENGTH: 25
<212> TYPE: DNA
<213> ORGANISM: Artificial sequence
<220> FEATURE:
<223> OTHER INFORMATION: primer

<400> SEQUENCE: 51
ggggactatc agcattggcg ggagg                                   25

<210> SEQ ID NO 52
<211> LENGTH: 32
<212> TYPE: DNA
<213> ORGANISM: Artificial sequence
<220> FEATURE:
<223> OTHER INFORMATION: primer

<400> SEQUENCE: 52
ccccacctgc agccaccatg aacacttcag cc                           32

<210> SEQ ID NO 53
<211> LENGTH: 33
<212> TYPE: DNA
<213> ORGANISM: Artificial sequence
<220> FEATURE:
<223> OTHER INFORMATION: primer

<400> SEQUENCE: 53
ggggaggatc cgcgcattgg cgggagggag tgc                          33

<210> SEQ ID NO 54
<211> LENGTH: 38
<212> TYPE: DNA
<213> ORGANISM: Artificial sequence
<220> FEATURE:
<223> OTHER INFORMATION: primer

<400> SEQUENCE: 54
cgcactctgc aacaaaaaat tcaaacgcac ctttcgcc                     38

<210> SEQ ID NO 55
<211> LENGTH: 38
<212> TYPE: DNA
<213> ORGANISM: Artificial sequence
<220> FEATURE:
<223> OTHER INFORMATION: primer

<400> SEQUENCE: 55
ggcgaaaggt gcgtttgaat tttttgttgc agagtgcg                     38

<210> SEQ ID NO 56
<211> LENGTH: 34
<212> TYPE: DNA
<213> ORGANISM: Artificial sequence
<220> FEATURE:
<223> OTHER INFORMATION: primer

<400> SEQUENCE: 56
ggggcgaatt cgccgccatg gaggaaccgg gtgc                         34

<210> SEQ ID NO 57
<211> LENGTH: 34
<212> TYPE: DNA
<213> ORGANISM: Artificial sequence
<220> FEATURE:
<223> OTHER INFORMATION: primer

```
<400> SEQUENCE: 57
gcaaacggta ccgcacttgt gcacttaaaa cgta                          34

<210> SEQ ID NO 58
<211> LENGTH: 39
<212> TYPE: DNA
<213> ORGANISM: Artificial sequence
<220> FEATURE:
<223> OTHER INFORMATION: primer

<400> SEQUENCE: 58
atgtccaata aaaatttaa aagagcattc cataaactg                      39

<210> SEQ ID NO 59
<211> LENGTH: 38
<212> TYPE: DNA
<213> ORGANISM: Artificial sequence
<220> FEATURE:
<223> OTHER INFORMATION: primer

<400> SEQUENCE: 59
ggaatgctct tttaaatttt ttattggaca tggtatag                      38

<210> SEQ ID NO 60
<211> LENGTH: 17
<212> TYPE: DNA
<213> ORGANISM: Artificial sequence
<220> FEATURE:
<223> OTHER INFORMATION: primer

<400> SEQUENCE: 60
aatacgactc actatag                                             17

<210> SEQ ID NO 61
<211> LENGTH: 49
<212> TYPE: DNA
<213> ORGANISM: Artificial sequence
<220> FEATURE:
<223> OTHER INFORMATION: primer

<400> SEQUENCE: 61
gccgccagtg tgatggatac tggtaccgct agcagtgagt catttgtac          49

<210> SEQ ID NO 62
<211> LENGTH: 39
<212> TYPE: DNA
<213> ORGANISM: Artificial sequence
<220> FEATURE:
<223> OTHER INFORMATION: primer

<400> SEQUENCE: 62 cccttatct acgcctttag cgcaaagaag ttcaagcgc                      39

<210> SEQ ID NO 63
<211> LENGTH: 39
<212> TYPE: DNA
<213> ORGANISM: Artificial sequence
<220> FEATURE:
<223> OTHER INFORMATION: primer

<400> SEQUENCE: 63
gcgcttgaac ttctttgcgc taaaggcgta gataagggg                     39

<210> SEQ ID NO 64
<211> LENGTH: 38
```

<212> TYPE: DNA
<213> ORGANISM: Artificial sequence
<220> FEATURE:
<223> OTHER INFORMATION: primer

<400> SEQUENCE: 64
ctgccggagc aaaaaattca aaagagcctt ccaggagc        38

<210> SEQ ID NO 65
<211> LENGTH: 38
<212> TYPE: DNA
<213> ORGANISM: Artificial sequence
<220> FEATURE:
<223> OTHER INFORMATION: primer

<400> SEQUENCE: 65
cctggaaggc tcttttgaat tttttgctcc ggcagtag        38

<210> SEQ ID NO 66
<211> LENGTH: 19
<212> TYPE: PRT
<213> ORGANISM: Artificial sequence
<220> FEATURE:
<223> OTHER INFORMATION: synthesized

<400> SEQUENCE: 66

Asn Pro Leu Ile Tyr Cys Arg Ser Pro Asp Phe Ile Arg Ala Phe Gln
1               5                   10                  15

Glu Leu Leu

<210> SEQ ID NO 67
<211> LENGTH: 19
<212> TYPE: PRT
<213> ORGANISM: Artificial sequence
<220> FEATURE:
<223> OTHER INFORMATION: synthesized

<400> SEQUENCE: 67

Asn Pro Leu Ile Tyr Cys Arg Ser Lys Lys Phe Lys Arg Ala Phe Gln
1               5                   10                  15

Glu Leu Leu

<210> SEQ ID NO 68
<211> LENGTH: 38
<212> TYPE: DNA
<213> ORGANISM: Artificial sequence
<220> FEATURE:
<223> OTHER INFORMATION: primer

<400> SEQUENCE: 68
cgtctctgct ccctggtacc gccaccttga gccagtgg        38

<210> SEQ ID NO 69
<211> LENGTH: 20
<212> TYPE: DNA
<213> ORGANISM: Artificial sequence
<220> FEATURE:
<223> OTHER INFORMATION: primer

<400> SEQUENCE: 69
taatacgact cactataggg                            20

<210> SEQ ID NO 70
<211> LENGTH: 38
<212> TYPE: DNA

```
<213> ORGANISM: Artificial sequence
<220> FEATURE:
<223> OTHER INFORMATION: primer

<400> SEQUENCE: 70
cgtctctgct ccctggtacc gccaccttga gccagtgg                                    38

<210> SEQ ID NO 71
<211> LENGTH: 37
<212> TYPE: DNA
<213> ORGANISM: Artificial sequence
<220> FEATURE:
<223> OTHER INFORMATION: primer

<400> SEQUENCE: 71
ctatgcggcc aaaaagttca aaagactgcc tgggtcc                                     37

<210> SEQ ID NO 72
<211> LENGTH: 38
<212> TYPE: DNA
<213> ORGANISM: Artificial sequence
<220> FEATURE:
<223> OTHER INFORMATION: primer

<400> SEQUENCE: 72
caggcagtct tttgaacttt ttggccgcat agatgggc                                    38

<210> SEQ ID NO 73
<211> LENGTH: 24
<212> TYPE: PRT
<213> ORGANISM: Artificial sequence
<220> FEATURE:
<223> OTHER INFORMATION: synthesized

<400> SEQUENCE: 73

Ser Ser Met Ala Met Val Pro Ile Tyr Ala Ala Tyr Lys Phe Cys Ser
1               5                   10                  15

Leu Pro Gly Ser Phe Arg Glu Lys
            20

<210> SEQ ID NO 74
<211> LENGTH: 24
<212> TYPE: PRT
<213> ORGANISM: Artificial sequence
<220> FEATURE:
<223> OTHER INFORMATION: synthesized

<400> SEQUENCE: 74

Ser Ser Met Ala Met Val Pro Ile Tyr Ala Ala Lys Lys Phe Lys Arg
1               5                   10                  15

Leu Pro Gly Ser Phe Arg Glu Lys
            20

<210> SEQ ID NO 75
<211> LENGTH: 37
<212> TYPE: DNA
<213> ORGANISM: Artificial sequence
<220> FEATURE:
<223> OTHER INFORMATION: primer

<400> SEQUENCE: 75
ctatgcggcc aaaaagttca aaagactgcc tgggtcc                                     37

<210> SEQ ID NO 76
<211> LENGTH: 38
```

<212> TYPE: DNA
<213> ORGANISM: Artificial sequence
<220> FEATURE:
<223> OTHER INFORMATION: primer

<400> SEQUENCE: 76
caggcagtct tttgaacttt ttggccgcat agatgggc                            38

<210> SEQ ID NO 77
<211> LENGTH: 24
<212> TYPE: PRT
<213> ORGANISM: Artificial sequence
<220> FEATURE:
<223> OTHER INFORMATION: synthesized

<400> SEQUENCE: 77

Ser Ser Met Ala Met Val Pro Ile Tyr Ala Ala Tyr Lys Phe Cys Ser
1               5                   10                  15

Leu Pro Gly Ser Phe Arg Glu Lys
            20

<210> SEQ ID NO 78
<211> LENGTH: 24
<212> TYPE: PRT
<213> ORGANISM: Artificial sequence
<220> FEATURE:
<223> OTHER INFORMATION: synthesized

<400> SEQUENCE: 78

Ser Ser Met Ala Met Val Pro Ile Tyr Ala Ala Lys Lys Phe Lys Arg
1               5                   10                  15

Leu Pro Gly Ser Phe Arg Glu Lys
            20

<210> SEQ ID NO 79
<211> LENGTH: 40
<212> TYPE: DNA
<213> ORGANISM: Artificial sequence
<220> FEATURE:
<223> OTHER INFORMATION: primer

<400> SEQUENCE: 79
gtcatttact aagcttgcca ccatggagac gacgcccttg                          40

<210> SEQ ID NO 80
<211> LENGTH: 37
<212> TYPE: DNA
<213> ORGANISM: Artificial sequence
<220> FEATURE:
<223> OTHER INFORMATION: primer

<400> SEQUENCE: 80
cctctcggtg agtggtaccg ccacagcatt caagcgg                             37

<210> SEQ ID NO 81
<211> LENGTH: 39
<212> TYPE: DNA
<213> ORGANISM: Artificial sequence
<220> FEATURE:
<223> OTHER INFORMATION: primer

<400> SEQUENCE: 81
ggacactgcc tggcaaagct tgcgagcatg gggccctgg                           39

<210> SEQ ID NO 82

```
<211> LENGTH: 40
<212> TYPE: DNA
<213> ORGANISM: Artificial sequence
<220> FEATURE:
<223> OTHER INFORMATION: primer

<400> SEQUENCE: 82
ggcgggactc caggcaggta ccgccgccac gtcatcctcc                              40

<210> SEQ ID NO 83
<211> LENGTH: 42
<212> TYPE: DNA
<213> ORGANISM: Artificial sequence
<220> FEATURE:
<223> OTHER INFORMATION: primer

<400> SEQUENCE: 83
ctatggaaga actggaaaaa atttaaaaga aacagcatca ac                          42

<210> SEQ ID NO 84
<211> LENGTH: 42
<212> TYPE: DNA
<213> ORGANISM: Artificial sequence
<220> FEATURE:
<223> OTHER INFORMATION: primer

<400> SEQUENCE: 84
caaagttgat gctgtttctt ttaaattttt tccagttctt cc                          42

<210> SEQ ID NO 85
<211> LENGTH: 20
<212> TYPE: PRT
<213> ORGANISM: Artificial sequence
<220> FEATURE:
<223> OTHER INFORMATION: synthesized

<400> SEQUENCE: 85

Phe Leu Leu Trp Lys Asn Trp Arg Leu Lys Asn Ile Asn Ser Ile Asn
1               5                   10                  15

Phe Asp Asn Pro
            20

<210> SEQ ID NO 86
<211> LENGTH: 20
<212> TYPE: PRT
<213> ORGANISM: Artificial sequence
<220> FEATURE:
<223> OTHER INFORMATION: synthesized

<400> SEQUENCE: 86

Phe Leu Leu Trp Lys Asn Trp Lys Lys Phe Lys Arg Asn Ser Ile Asn
1               5                   10                  15

Phe Asp Asn Pro
            20

<210> SEQ ID NO 87
<211> LENGTH: 40
<212> TYPE: DNA
<213> ORGANISM: Artificial sequence
<220> FEATURE:
<223> OTHER INFORMATION: primer

<400> SEQUENCE: 87
gctcttcggg ctcgagcagc gatgcgaccc tccgggacgg                              40
```

<210> SEQ ID NO 88
<211> LENGTH: 39
<212> TYPE: DNA
<213> ORGANISM: Artificial sequence
<220> FEATURE:
<223> OTHER INFORMATION: primer

<400> SEQUENCE: 88
ctatcctccg tggtaccgct gctccaataa attcactgc                    39

<210> SEQ ID NO 89
<211> LENGTH: 37
<212> TYPE: DNA
<213> ORGANISM: Artificial sequence
<220> FEATURE:
<223> OTHER INFORMATION: primer

<400> SEQUENCE: 89
gatcatcact ccaaagaaat ttaaaagacg tattatt                       37

<210> SEQ ID NO 90
<211> LENGTH: 40
<212> TYPE: DNA
<213> ORGANISM: Artificial sequence
<220> FEATURE:
<223> OTHER INFORMATION: primer

<400> SEQUENCE: 90
taatacgtct tttaaatttc tttggagtga tgatcaaccg                    40

<210> SEQ ID NO 91
<211> LENGTH: 18
<212> TYPE: PRT
<213> ORGANISM: Artificial sequence
<220> FEATURE:
<223> OTHER INFORMATION: synthesized

<400> SEQUENCE: 91

Arg Leu Ile Ile Thr Pro Gly Thr Phe Lys Glu Arg Ile Ile Lys Ser
1               5                   10                  15

Ile Thr

<210> SEQ ID NO 92
<211> LENGTH: 18
<212> TYPE: PRT
<213> ORGANISM: Artificial sequence
<220> FEATURE:
<223> OTHER INFORMATION: synthesized

<400> SEQUENCE: 92

Arg Leu Ile Ile Thr Pro Lys Lys Phe Lys Arg Arg Ile Ile Lys Ser
1               5                   10                  15

Ile Thr

<210> SEQ ID NO 93
<211> LENGTH: 34
<212> TYPE: DNA
<213> ORGANISM: Artificial sequence
<220> FEATURE:
<223> OTHER INFORMATION: primer

<400> SEQUENCE: 93
gggtctctaa gcttgccgcc atgtccggga aggg                         34

<210> SEQ ID NO 94

<211> LENGTH: 33
<212> TYPE: DNA
<213> ORGANISM: Artificial sequence
<220> FEATURE:
<223> OTHER INFORMATION: primer

<400> SEQUENCE: 94
ccgcggcccg gaattcggat ggcatggttg gtg                          33

<210> SEQ ID NO 95
<211> LENGTH: 37
<212> TYPE: DNA
<213> ORGANISM: Artificial sequence
<220> FEATURE:
<223> OTHER INFORMATION: primer

<400> SEQUENCE: 95
cgtgcccaag aaattcaagc gcctcaaagc cgtggtc                     37

<210> SEQ ID NO 96
<211> LENGTH: 38
<212> TYPE: DNA
<213> ORGANISM: Artificial sequence
<220> FEATURE:
<223> OTHER INFORMATION: primer

<400> SEQUENCE: 96
cggctttgag gcgcttgaat tcttgggca cgttctgc                     38

<210> SEQ ID NO 97
<211> LENGTH: 22
<212> TYPE: PRT
<213> ORGANISM: Artificial sequence
<220> FEATURE:
<223> OTHER INFORMATION: synthesized

<400> SEQUENCE: 97

Phe His Pro Glu Gln Asn Val Pro Lys Arg Lys Arg Ser Leu Lys Ala
1               5                   10                  15

Val Val Thr Ala Ala Thr
            20

<210> SEQ ID NO 98
<211> LENGTH: 22
<212> TYPE: PRT
<213> ORGANISM: Artificial sequence
<220> FEATURE:
<223> OTHER INFORMATION: synthesized

<400> SEQUENCE: 98

Phe His Pro Glu Gln Asn Val Pro Lys Lys Phe Lys Arg Leu Lys Ala
1               5                   10                  15

Val Val Thr Ala Ala Thr
            20

<210> SEQ ID NO 99
<211> LENGTH: 39
<212> TYPE: DNA
<213> ORGANISM: Artificial sequence
<220> FEATURE:
<223> OTHER INFORMATION: primer

<400> SEQUENCE: 99
ggagacccca agcttccgca gccatgggca ccgggggcc                   39

<210> SEQ ID NO 100
<211> LENGTH: 39
<212> TYPE: DNA
<213> ORGANISM: Artificial sequence
<220> FEATURE:
<223> OTHER INFORMATION: primer

<400> SEQUENCE: 100
ccccgccacg ggccccggaa ggattggacc gaggcaagg            39

<210> SEQ ID NO 101
<211> LENGTH: 42
<212> TYPE: DNA
<213> ORGANISM: Artificial sequence
<220> FEATURE:
<223> OTHER INFORMATION: primer

<400> SEQUENCE: 101
ccgctgggac cgaaaaaatt taagagaaac cctgagtatc tc        42

<210> SEQ ID NO 102
<211> LENGTH: 43
<212> TYPE: DNA
<213> ORGANISM: Artificial sequence
<220> FEATURE:
<223> OTHER INFORMATION: primer

<400> SEQUENCE: 102
gatactcagg gtttctctta aattttttcg gtcccagcgg ccc       43

<210> SEQ ID NO 103
<211> LENGTH: 20
<212> TYPE: DNA
<213> ORGANISM: Artificial sequence
<220> FEATURE:
<223> OTHER INFORMATION: primer

<400> SEQUENCE: 103
taatacgact cactataggg                                 20

<210> SEQ ID NO 104
<211> LENGTH: 44
<212> TYPE: DNA
<213> ORGANISM: Artificial sequence
<220> FEATURE:
<223> OTHER INFORMATION: primer

<400> SEQUENCE: 104
gactgcagcc tggtggtacc gcagagcaag ccacatagct gggg      44

<210> SEQ ID NO 105
<211> LENGTH: 20
<212> TYPE: DNA
<213> ORGANISM: Artificial sequence
<220> FEATURE:
<223> OTHER INFORMATION: primer

<400> SEQUENCE: 105
taatacgact cactataggg                                 20

<210> SEQ ID NO 106
<211> LENGTH: 44
<212> TYPE: DNA
<213> ORGANISM: Artificial sequence
<220> FEATURE:
<223> OTHER INFORMATION: primer

```
<400> SEQUENCE: 106
gactgcagcc tggtggtacc gcagagcaag ccacatagct gggg                          44

<210> SEQ ID NO 107
<211> LENGTH: 40
<212> TYPE: DNA
<213> ORGANISM: Artificial sequence
<220> FEATURE:
<223> OTHER INFORMATION: primer

<400> SEQUENCE: 107
gctgctctcc cacaaaaagt ttaagcggca gaagatctgg                               40

<210> SEQ ID NO 108
<211> LENGTH: 40
<212> TYPE: DNA
<213> ORGANISM: Artificial sequence
<220> FEATURE:
<223> OTHER INFORMATION: primer

<400> SEQUENCE: 108
ccagatcttc tgccgcttaa acttttttgtg ggagagcagc                              40

<210> SEQ ID NO 109
<211> LENGTH: 21
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (14)..(14)
<223> OTHER INFORMATION: Xaa equals Orn

<400> SEQUENCE: 109

Thr Val Leu Ala Leu Leu Ser His Arg Arg Ala Leu Lys Xaa Lys Ile
1               5                   10                  15

Trp Pro Gly Ile Pro
            20

<210> SEQ ID NO 110
<211> LENGTH: 21
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (14)..(14)
<223> OTHER INFORMATION: Xaa equals Orn

<400> SEQUENCE: 110

Thr Val Leu Ala Leu Leu Ser His Lys Lys Phe Lys Arg Xaa Lys Ile
1               5                   10                  15

Trp Pro Gly Ile Pro
            20

<210> SEQ ID NO 111
<211> LENGTH: 40
<212> TYPE: DNA
<213> ORGANISM: Artificial sequence
<220> FEATURE:
<223> OTHER INFORMATION: primer

<400> SEQUENCE: 111
gctcttcggg ctcgagcagc gatgcgaccc tccgggacgg                               40
```

<210> SEQ ID NO 112
<211> LENGTH: 39
<212> TYPE: DNA
<213> ORGANISM: Artificial sequence
<220> FEATURE:
<223> OTHER INFORMATION: primer

<400> SEQUENCE: 112
ctatcctccg tggtaccgct gctccaataa attcactgc                    39

<210> SEQ ID NO 113
<211> LENGTH: 37
<212> TYPE: DNA
<213> ORGANISM: Artificial sequence
<220> FEATURE:
<223> OTHER INFORMATION: primer

<400> SEQUENCE: 113
cacatcgttc ggaagaagtt taagcggagg ctgctgc                      37

<210> SEQ ID NO 114
<211> LENGTH: 40
<212> TYPE: DNA
<213> ORGANISM: Artificial sequence
<220> FEATURE:
<223> OTHER INFORMATION: primer

<400> SEQUENCE: 114
cctgcagcag cctccgctta aacttcttcc gaacgatgtg                   40

<210> SEQ ID NO 115
<211> LENGTH: 19
<212> TYPE: PRT
<213> ORGANISM: Artificial sequence
<220> FEATURE:
<223> OTHER INFORMATION: synthesized

<400> SEQUENCE: 115

Arg Arg Arg His Ile Val Arg Lys Arg Thr Leu Arg Arg Leu Leu Gln
1               5                  10                  15

Glu Arg Glu

<210> SEQ ID NO 116
<211> LENGTH: 19
<212> TYPE: PRT
<213> ORGANISM: Artificial sequence
<220> FEATURE:
<223> OTHER INFORMATION: synthesized

<400> SEQUENCE: 116

Arg Arg Arg His Ile Val Arg Lys Lys Phe Lys Arg Arg Leu Leu Gln
1               5                  10                  15

Glu Arg Glu

<210> SEQ ID NO 117
<211> LENGTH: 49
<212> TYPE: DNA
<213> ORGANISM: Artificial sequence
<220> FEATURE:
<223> OTHER INFORMATION: primer

<400> SEQUENCE: 117
gaggactctg aacaccgaat tcgccgccat ggacgggact gggctggtg         49

<210> SEQ ID NO 118
<211> LENGTH: 45
<212> TYPE: DNA
<213> ORGANISM: Artificial sequence
<220> FEATURE:
<223> OTHER INFORMATION: primer

<400> SEQUENCE: 118
gtgtggcagg attcatctgg gtaccgcggt tgggtgctga ccgtt           45

<210> SEQ ID NO 119
<211> LENGTH: 41
<212> TYPE: DNA
<213> ORGANISM: Artificial sequence
<220> FEATURE:
<223> OTHER INFORMATION: primer

<400> SEQUENCE: 119
cctctgagga cctgaaaaag aagagaaagg ctggcatcgc c               41

<210> SEQ ID NO 120
<211> LENGTH: 41
<212> TYPE: DNA
<213> ORGANISM: Artificial sequence
<220> FEATURE:
<223> OTHER INFORMATION: primer

<400> SEQUENCE: 120
ggcgatgcca gcctttctct cttttttcag gtcctcagag g               41

<210> SEQ ID NO 121
<211> LENGTH: 33
<212> TYPE: PRT
<213> ORGANISM: Artificial sequence
<220> FEATURE:
<223> OTHER INFORMATION: synthesized

<400> SEQUENCE: 121

Asn Pro Ile Ile Tyr Ala Phe Asn Ala Asp Phe Arg Lys Ala Phe Ser
1               5                  10                  15

Thr Leu Leu Ser Ser Glu Asp Leu Lys Lys Glu Glu Ala Ala Gly Ile
            20                  25                  30

Ala

<210> SEQ ID NO 122
<211> LENGTH: 33
<212> TYPE: PRT
<213> ORGANISM: Artificial sequence
<220> FEATURE:
<223> OTHER INFORMATION: synthesized

<400> SEQUENCE: 122

Asn Pro Ile Ile Tyr Ala Phe Asn Ala Lys Lys Phe Lys Arg Phe Ser
1               5                  10                  15

Thr Leu Leu Ser Ser Glu Asp Leu Lys Lys Lys Arg Lys Ala Gly Ile
            20                  25                  30

Ala

<210> SEQ ID NO 123
<211> LENGTH: 45
<212> TYPE: DNA
<213> ORGANISM: Artificial sequence
<220> FEATURE:
<223> OTHER INFORMATION: primer

<400> SEQUENCE: 123
cctagtccgc agcaggccga attcgccacc atggacagca gcacc    45

<210> SEQ ID NO 124
<211> LENGTH: 44
<212> TYPE: DNA
<213> ORGANISM: Artificial sequence
<220> FEATURE:
<223> OTHER INFORMATION: primer

<400> SEQUENCE: 124
gatggtgtga gaccggtacc gcgggcaatg gagcagtttc tgcc    44

<210> SEQ ID NO 125
<211> LENGTH: 45
<212> TYPE: DNA
<213> ORGANISM: Artificial sequence
<220> FEATURE:
<223> OTHER INFORMATION: primer

<400> SEQUENCE: 125
cctagtccgc agcaggccga attcgccacc atggacagca gcacc    45

<210> SEQ ID NO 126
<211> LENGTH: 45
<212> TYPE: DNA
<213> ORGANISM: Artificial sequence
<220> FEATURE:
<223> OTHER INFORMATION: primer

<400> SEQUENCE: 126
ggatggtgtg agaccggtac cgcgggcaat ggagcagttt ctgcc    45

<210> SEQ ID NO 127
<211> LENGTH: 30
<212> TYPE: DNA
<213> ORGANISM: Artificial sequence
<220> FEATURE:
<223> OTHER INFORMATION: primer

<400> SEQUENCE: 127
gccttcctgg ataaaaaatt caagcgatgc    30

<210> SEQ ID NO 128
<211> LENGTH: 31
<212> TYPE: DNA
<213> ORGANISM: Artificial sequence
<220> FEATURE:
<223> OTHER INFORMATION: primer

<400> SEQUENCE: 128
gcatcgcttg aattttttat ccaggaaggc g    31

<210> SEQ ID NO 129
<211> LENGTH: 7
<212> TYPE: PRT
<213> ORGANISM: Artificial sequence
<220> FEATURE:
<223> OTHER INFORMATION: synthesized

<400> SEQUENCE: 129

Pro Lys Lys Lys Arg Lys Val
1               5

```
<210> SEQ ID NO 130
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (4)..(14)
<223> OTHER INFORMATION: Xaa equals a sequence of any 11 amino acids

<400> SEQUENCE: 130

Arg Arg Arg Xaa Lys Arg Arg Lys
1               5

<210> SEQ ID NO 131
<211> LENGTH: 7
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (3)..(17)
<223> OTHER INFORMATION: Xaa equals a sequence of any 15 amino acids

<400> SEQUENCE: 131

Lys Lys Xaa Lys Lys Arg Lys
1               5

<210> SEQ ID NO 132
<211> LENGTH: 6
<212> TYPE: PRT
<213> ORGANISM: Artificial sequence
<220> FEATURE:
<223> OTHER INFORMATION: synthesized

<400> SEQUENCE: 132

Lys Arg Lys Arg Arg Pro
1               5

<210> SEQ ID NO 133
<211> LENGTH: 9
<212> TYPE: PRT
<213> ORGANISM: Artificial sequence
<220> FEATURE:
<223> OTHER INFORMATION: synthesized

<400> SEQUENCE: 133

Pro Lys Lys Asn Arg Leu Arg Arg Lys
1               5

<210> SEQ ID NO 134
<211> LENGTH: 10
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (5)..(24)
<223> OTHER INFORMATION: Xaa equals a sequence of any 20 amino acids

<400> SEQUENCE: 134

Lys Arg Gln Arg Xaa Lys Lys Ser Lys Lys
1               5                   10

<210> SEQ ID NO 135
<211> LENGTH: 9
```

```
<212> TYPE: PRT
<213> ORGANISM: Artificial sequence
<220> FEATURE:
<223> OTHER INFORMATION: synthesized

<400> SEQUENCE: 135

Pro Ala Ala Lys Arg Val Lys Leu Asp
1               5

<210> SEQ ID NO 136
<211> LENGTH: 6
<212> TYPE: PRT
<213> ORGANISM: Artificial sequence
<220> FEATURE:
<223> OTHER INFORMATION: synthesized

<400> SEQUENCE: 136

Gln Arg Lys Arg Gln Lys
1               5

<210> SEQ ID NO 137
<211> LENGTH: 17
<212> TYPE: PRT
<213> ORGANISM: Artificial sequence
<220> FEATURE:
<223> OTHER INFORMATION: synthesized

<400> SEQUENCE: 137

His Arg Ile Glu Glu Lys Arg Lys Arg Thr Tyr Glu Thr Phe Lys Ser
1               5                   10                  15

Ile

<210> SEQ ID NO 138
<211> LENGTH: 7
<212> TYPE: PRT
<213> ORGANISM: Artificial sequence
<220> FEATURE:
<223> OTHER INFORMATION: synthesized

<400> SEQUENCE: 138

Lys Lys Lys Tyr Lys Leu Lys
1               5

<210> SEQ ID NO 139
<211> LENGTH: 7
<212> TYPE: PRT
<213> ORGANISM: Artificial sequence
<220> FEATURE:
<223> OTHER INFORMATION: synthesized

<400> SEQUENCE: 139

Lys Ser Lys Lys Lys Ala Gln
1               5

<210> SEQ ID NO 140
<211> LENGTH: 9
<212> TYPE: PRT
<213> ORGANISM: Artificial sequence
<220> FEATURE:
<223> OTHER INFORMATION: synthesized

<400> SEQUENCE: 140

Lys Lys Lys Lys Arg Lys Arg Glu Lys
1               5

<210> SEQ ID NO 141
```

```
<211> LENGTH: 9
<212> TYPE: PRT
<213> ORGANISM: Artificial sequence
<220> FEATURE:
<223> OTHER INFORMATION: synthesized

<400> SEQUENCE: 141

Leu Lys Arg Pro Arg Ser Pro Ser Ser
1               5

<210> SEQ ID NO 142
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (4)..(25)
<223> OTHER INFORMATION: Xaa equals a sequence of any 22 amino acids

<400> SEQUENCE: 142

Lys Arg Lys Xaa Lys Glu Leu Gln Lys Gln Ile Thr Lys
1               5                   10

<210> SEQ ID NO 143
<211> LENGTH: 9
<212> TYPE: PRT
<213> ORGANISM: Artificial sequence
<220> FEATURE:
<223> OTHER INFORMATION: synthesized

<400> SEQUENCE: 143

Gly Lys Lys Lys Tyr Lys Leu Lys His
1               5

<210> SEQ ID NO 144
<211> LENGTH: 7
<212> TYPE: PRT
<213> ORGANISM: Artificial sequence
<220> FEATURE:
<223> OTHER INFORMATION: synthesized

<400> SEQUENCE: 144

Lys Lys Lys Tyr Lys Leu Lys
1               5

<210> SEQ ID NO 145
<211> LENGTH: 7
<212> TYPE: PRT
<213> ORGANISM: Artificial sequence
<220> FEATURE:
<223> OTHER INFORMATION: synthesized

<400> SEQUENCE: 145

Lys Ser Lys Lys Lys Ala Gln
1               5

<210> SEQ ID NO 146
<211> LENGTH: 12
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (4)..(353)
<223> OTHER INFORMATION: Xaa equals a sequence of any 350 amino acids
```

```
<400> SEQUENCE: 146

Glu Glu Asp Xaa Lys Lys Lys Arg Glu Arg Leu Asp
1               5                   10

<210> SEQ ID NO 147
<211> LENGTH: 25
<212> TYPE: PRT
<213> ORGANISM: Artificial sequence
<220> FEATURE:
<223> OTHER INFORMATION: synthesized

<400> SEQUENCE: 147

Cys Tyr Phe Gln Lys Lys Ala Ala Asn Met Leu Gln Gln Ser Gly Ser
1               5                   10                  15

Lys Asn Thr Gly Ala Lys Lys Arg Lys
            20                  25

<210> SEQ ID NO 148
<211> LENGTH: 12
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (6)..(328)
<223> OTHER INFORMATION: Xaa equals a sequence of any 323 amino acids

<400> SEQUENCE: 148

Asp Ile Leu Arg Arg Xaa Pro Lys Gln Lys Arg Lys
1               5                   10

<210> SEQ ID NO 149
<211> LENGTH: 22
<212> TYPE: PRT
<213> ORGANISM: Artificial sequence
<220> FEATURE:
<223> OTHER INFORMATION: synthesized

<400> SEQUENCE: 149

Ser Ser Asp Asp Glu Ala Thr Ala Asp Ser Gln His Ser Thr Pro Pro
1               5                   10                  15

Lys Lys Lys Arg Lys Val
            20

<210> SEQ ID NO 150
<211> LENGTH: 12
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (6)..(14)
<223> OTHER INFORMATION: Xaa equals a sequence of any 9 amino acids

<400> SEQUENCE: 150

Arg Lys Lys Arg Lys Xaa Lys Ala Lys Lys Ser Lys
1               5                   10

<210> SEQ ID NO 151
<211> LENGTH: 7
<212> TYPE: PRT
<213> ORGANISM: Artificial sequence
<220> FEATURE:
<223> OTHER INFORMATION: synthesized
<220> FEATURE:
```

```
<221> NAME/KEY: MISC_FEATURE
<222> LOCATION: (3)..(13)
<223> OTHER INFORMATION: Xaa equals a sequence of any 11 amino acids

<400> SEQUENCE: 151

Lys Arg Xaa Lys Lys Leu Arg
1               5

<210> SEQ ID NO 152
<211> LENGTH: 11
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (5)..(27)
<223> OTHER INFORMATION: Xaa equals a sequence of any 22 amino acids
<220> FEATURE:
<221> NAME/KEY: MISC_FEATURE
<222> LOCATION: (5)..(26)
<223> OTHER INFORMATION: Xaa equals any amino acid

<400> SEQUENCE: 152

Arg Arg Pro Ser Xaa Arg Arg Lys Arg Gln Lys
1               5                   10

<210> SEQ ID NO 153
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (4)..(14)
<223> OTHER INFORMATION: Xaa equals a sequence of any 11 amino acids

<400> SEQUENCE: 153

Arg Arg Arg Xaa Lys Arg Arg Lys
1               5

<210> SEQ ID NO 154
<211> LENGTH: 7
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (3)..(12)
<223> OTHER INFORMATION: Xaa equals a sequence of any 10 amino acids

<400> SEQUENCE: 154

Lys Arg Xaa Lys Lys Lys Leu
1               5

<210> SEQ ID NO 155
<211> LENGTH: 12
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (5)..(11)
<223> OTHER INFORMATION: Xaa equals a sequence of any 7 amino acids

<400> SEQUENCE: 155

Arg Lys Arg Lys Xaa Arg Arg Ser Arg Tyr Arg Lys
```

-continued

```
<210> SEQ ID NO 156
<211> LENGTH: 9
<212> TYPE: PRT
<213> ORGANISM: Artificial sequence
<220> FEATURE:
<223> OTHER INFORMATION: synthesized

<400> SEQUENCE: 156

Met Ile Ser Glu Ala Leu Arg Lys Ala
1               5

<210> SEQ ID NO 157
<211> LENGTH: 5
<212> TYPE: PRT
<213> ORGANISM: Artificial sequence
<220> FEATURE:
<223> OTHER INFORMATION: synthesized

<400> SEQUENCE: 157

Lys Lys Phe Lys Arg
1               5

<210> SEQ ID NO 158
<211> LENGTH: 9
<212> TYPE: PRT
<213> ORGANISM: Artificial sequence
<220> FEATURE:
<223> OTHER INFORMATION: synthesized

<400> SEQUENCE: 158

Ala Phe Ser Ala Lys Lys Phe Lys Arg
1               5
```